United States Patent
Shen et al.

(10) Patent No.: US 10,099,920 B2
(45) Date of Patent: Oct. 16, 2018

(54) SCALABLE NUCLEIC ACID-BASED NANOFABRICATION

(71) Applicant: President and Fellows of Harvard College, Cambridge, MA (US)

(72) Inventors: Jie Shen, Worcester, MA (US); Wei Sun, Brookline, MA (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/312,854

(22) PCT Filed: May 22, 2015

(86) PCT No.: PCT/US2015/032198
§ 371 (c)(1),
(2) Date: Nov. 21, 2016

(87) PCT Pub. No.: WO2015/187390
PCT Pub. Date: Dec. 10, 2015

(65) Prior Publication Data
US 2017/0190573 A1    Jul. 6, 2017

Related U.S. Application Data

(60) Provisional application No. 62/157,595, filed on May 6, 2015, provisional application No. 62/079,877, filed
(Continued)

(51) Int. Cl.
*B82B 3/00* (2006.01)
*B82Y 5/00* (2011.01)
(Continued)

(52) U.S. Cl.
CPC .............. *B82B 3/0047* (2013.01); *B82Y 5/00* (2013.01); *B82Y 30/00* (2013.01); *B82Y 40/00* (2013.01); *B01J 2219/00659* (2013.01)

(58) Field of Classification Search
None
See application file for complete search history.

(56) References Cited

U.S. PATENT DOCUMENTS

| | | |
|---|---|---|
| 5,386,020 A | 1/1995 | Seeman et al. |
| 6,255,469 B1 | 7/2001 | Seeman et al. |

(Continued)

FOREIGN PATENT DOCUMENTS

| | | |
|---|---|---|
| CN | 1390253 A | 1/2003 |
| JP | 2004-510780 A | 4/2004 |

(Continued)

OTHER PUBLICATIONS

Surwade et al (Molecular Lithography through DNA-Mediated Etching and Masking of SiO2; J. Am. Chem. Soc. 2011, 133, 11868-11871).*

(Continued)

*Primary Examiner* — Shamim Ahmed
(74) *Attorney, Agent, or Firm* — Wolf, Greenfield & Sacks, P.C.

(57) ABSTRACT

The present disclosure relates to the alignment of moieties (e.g., nanoparticles and/or nanowires) into prescribed architectures on two- and/or three-dimensional substrates (e.g., nucleic acid nanostructures/crystals). The present disclosure also relates to a nucleic acid (e.g., DNA) lithography method that includes, in some embodiments, adsorbing a bare nucleic acid nanostructure onto a surface of a substrate, and etching the surface of the substrate containing the bare nucleic acid nanostructure, thereby producing a patterned substrate.

38 Claims, 23 Drawing Sheets

Related U.S. Application Data on Nov. 14, 2014, provisional application No. 62/002,117, filed on May 22, 2014.

(51) Int. Cl.
  *B82Y 40/00* (2011.01)
  *H01L 21/302* (2006.01)
  *B82Y 30/00* (2011.01)

(56) References Cited

U.S. PATENT DOCUMENTS

| | | |
|---|---|---|
| 6,444,650 B1 | 9/2002 | Cech et al. |
| 6,444,661 B1 | 9/2002 | Barton et al. |
| 7,745,594 B2 | 6/2010 | Seelig et al. |
| 7,842,793 B2 | 11/2010 | Rothemund |
| 8,877,438 B2 | 11/2014 | Yin |
| 9,796,749 B2 | 10/2017 | Yin |
| 2003/0219790 A1 | 11/2003 | Seeman et al. |
| 2006/0078910 A1 | 4/2006 | Seeman et al. |
| 2007/0117109 A1 | 5/2007 | Rothemund |
| 2007/0238096 A1 | 10/2007 | Reich et al. |
| 2008/0221315 A1 | 9/2008 | Garibotti et al. |
| 2009/0227774 A1 | 9/2009 | Turberfield et al. |
| 2010/0216978 A1 | 8/2010 | Shih |
| 2010/0291485 A1 | 11/2010 | Lapsys et al. |
| 2012/0022244 A1 | 1/2012 | Yin et al. |
| 2012/0251583 A1 | 10/2012 | Rothemund |
| 2013/0065777 A1 | 3/2013 | Altug et al. |
| 2013/0316358 A1 | 11/2013 | Navon et al. |
| 2014/0213778 A1 | 7/2014 | Yin et al. |
| 2015/0218204 A1 | 8/2015 | Yin et al. |
| 2015/0329584 A1 | 11/2015 | Peng et al. |
| 2017/0015698 A1 | 1/2017 | Iinuma et al. |
| 2018/0044372 A1 | 2/2018 | Han et al. |

FOREIGN PATENT DOCUMENTS

| | | |
|---|---|---|
| JP | 2008-504846 A | 2/2008 |
| WO | WO 01/36624 A1 | 5/2001 |
| WO | WO 2005/024018 A1 | 3/2005 |
| WO | WO 2006/017432 A2 | 2/2006 |
| WO | WO 2007/012807 A2 | 2/2007 |
| WO | WO 2009/093558 A1 | 7/2009 |
| WO | WO 2012/058638 A2 | 5/2012 |
| WO | WO 2013/022694 A1 | 2/2013 |
| WO | WO 2013/088098 A2 | 6/2013 |
| WO | WO 2014/018675 A1 | 1/2014 |
| WO | WO 2014/074597 A1 | 5/2014 |
| WO | WO 2015/138231 A1 | 9/2015 |
| WO | WO 2016/144755 A1 | 9/2016 |

OTHER PUBLICATIONS

Acuna et al., Fluorescence enhancement at docking sites of DNA-directed self-assembled nanoantennas. Science. Oct. 26, 2012;338(6106):506-10. doi:10.1126/science.1228638.
Aldaye et al., Assembling materials with DNA as the guide. Science. Sep. 26, 2008;321(5897):1795-9. doi: 10.1126/science.1154533.
Aldaye et al., Modular access to structurally switchable 3D discrete DNA assemblies. J Am Chem Soc. Nov. 7, 2007;129(44):13376-7. Epub Oct. 16, 2007.
Aldaye et al., Sequential self-assembly of a DNA hexagon as a template for the organization of gold nanoparticles. Angew Chem Int Ed Engl. Mar. 27, 2006;45(14):2204-9.
Alexander et al., On Types of Knotted Curves. Annals of Mathematics 1926-1927, 28(1/4): 562-586.
Alexander, Topical Invariants of Knots and Links. Transations of the American Mathematical Society 1928, 30(2): 275-306.
Andersen et al., Self-assembly of a nanoscale DNA box with a controllable lid. Nature. May 7, 2009;459(7243):73-6. doi:10.1038/nature07971.
Anthony, MIT and Harvard engineers create graphene electronics with DNA based lithography. Extremetech.com. Apr. 10, 2013. http://www.extremetech.com/computing/153046-mit-and-harvard-engineers-create-graphene-electronics-with-dna-based-lithography.
Barish et al., An information-bearing seed for nucleating algorithmic self-assembly. Proc Natl Acad Sci U S A. Apr. 14, 2009;106(15):6054-9. doi: 10.1073/pnas.0808736106. Epub Mar. 24, 2009.
Bath et al., DNA nanomachines. Nat Nanotechnol. May 2007;2(5):275-84. doi:10.1038/nnano.2007.104.
Berardi et al., Mitochondrial uncoupling protein 2 structure determined by NMR molecular fragment searching. Nature. Jul. 24, 2011;476(7358):109-13. doi: 10.1038/nature10257.
Bertrand et al., Flexibility of the B-DNA backbone: effects of local and neighbouring sequences on pyrimidine-purine steps. Nucleic Acids Res. Mar. 1, 1998;26(5):1261-7.
Bhatia et al., Icosahedral DNA nanocapsules by modular assembly. Angew Chem Int Ed Engl. 2009;48(23):4134-7.doi:10.1002/anie.200806000.
Cataldo et al., DNA degradation with ozone. Int J Biol Macromol. May 30, 2006;38(3-5):248-54. Epub Apr. 17, 2006.
Chen et al., DNA-directed assembly of single-wall carbon nanotubes. J Am Chem Soc. Jul. 18, 2007;129(28):8696-7. Epub Jun. 23, 2007.
Chen et al., Invadable self-assembly: combining robustness with efficiency. Proceeding SODA '04 Proceedings of the fifteenth annual ACM-SIAM symposium on Discrete algorithms. 2004:890-9.
Chen et al., Synthesis from DNA of a molecule with the connectivity of a cube. Nature. Apr. 18, 1991;350(6319):631-3.
Choi et al., Programmable in situ amplification for multiplexed imaging of mRNA expression. Nat Biotechnol. Nov. 2010;28(11):1208-12. doi: 10.1038/nbt.1692. Epub Oct. 31, 2010.
Chworos et al., Building programmable jigsaw puzzles with RNA. Science. Dec. 17, 2004;306(5704):2068-72.
Delebecque et al., Organization of intracellular reactions with rationally designed RNA assemblies. Science. Jul. 22, 2011;333(6041):470-4. doi: 10.1126/science.1206938. Epub Jun. 23, 2011.
Dietz et al., Folding DNA into twisted and curved nanoscale shapes. Science. Aug. 7, 2009;325(5941):725-30. doi: 10.1126/science.1174251.
Dimitrakakis et al., Top-down patterning of zeolitic imidazolate framework composite thin films by deep X-ray lithography. Chem Commun (Camb). Aug. 4, 2012;48(60):7483-5. doi: 10.1039/c2cc33292b. Epub Jun. 22, 2012.
Douglas et al., A logic-gated nanorobot for targeted transport of molecular payloads. Science. Feb. 17, 2012;335(6070):831-4. doi:10.1126/science.1214081.
Douglas et al., DNA-nanotube-induced alignment of membrane proteins for NMR structure determination. Proc Natl Acad Sci U S A. Apr. 17, 2007;104(16):6644-8. Epub Apr. 2, 2007.
Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.
Douglas et al., Self-assembly of DNA into nanoscale three-dimensional shapes. Nature. May 21, 2009;459(7245):414-8.doi: 10.1038/nature08016.
Erben et al., A self-assembled DNA bipyramid. J Am Chem Soc. Jun. 6, 2007;129(22):6992-3. Epub May 15, 2007.
Feldkamp et al., Rational design of DNA nanoarchitectures. Angew Chem Int Ed Engl. Mar. 13, 2006;45(12):1856-76.
Fratini et al., Reversible bending and helix geometry in a B-DNA dodecamer: CGCGAATTBrCGCG. J Biol Chem. Dec. 25, 1982;257(24):14686-707.
Fu et al., DNA double-crossover molecules. Biochemistry. Apr. 6, 1993;32(13):3211-20.
Fu et al., Interenzyme substrate diffusion for an enzyme cascade organized on spatially addressable DNA nanostructures. J Am Chem Soc. Mar. 28, 2012;134(12):5516-9. doi:10.1021/ja300897h. Epub Mar. 16, 2012.
Geary et al., A single-stranded architecture for cotranscriptional folding of RNA nanostructures. Science. Aug. 15, 2014;345(6198):799-804. doi: 10.1126/science.1253920.

(56) References Cited

OTHER PUBLICATIONS

Goodman et al., Rapid chiral assembly of rigid DNA building blocks for molecular nanofabrication. Science. Dec. 9, 2005;310(5754):1661-5.
Goodman et al., Reconfigurable, braced, three-dimensional DNA nanostructures. Nat Nanotechnol. Feb. 2008;3(2):93-6. doi: 10.1038/nnano.2008.3. Epub Feb. 3, 2008.
Han et al., DNA gridiron nanostructures based on four-arm junctions. Science. Mar. 22, 2013;339(6126):1412-5. doi: 10.1126/science.1232252.
Han et al., DNA origami with complex curvatures in three-dimensional space. Science. Apr. 15, 2011;332(6027):342-6. doi:10.1126/science.1202998.
Han et al., Folding and cutting DNA into reconfigurable topological nanostructures. Nat Nanotechnol. Oct. 2010;5(10):712-7. doi:10.1038/nnano.2010.193. Epub Oct. 3, 2010.
Han et al., Unidirectional scaffold-strand arrangement in DNA origami. Angew Chem Int Ed Engl. Aug. 19, 2013;52(34):9031-4. doi: 10.1002/anie.201302177. Epub Jul. 14, 2013.
Hansma et al., DNA binding to mica correlates with cationic radius:assay by atomic force microscopy. Biophys J. Apr. 1996;70(4):1933-9.
He et al., Hierarchical self-assembly of DNA into symmetric supramolecular polyhedra. Nature. Mar. 13, 2008;452(7184):198-201. doi: 10.1038/nature06597.
Hell, Far-field optical nanoscopy. Science. May 25, 2007;316(5828):1153-8.
Horiya et al., RNA LEGO: magnesium-dependent formation of specific RNA assemblies through kissing interactions. Chem Biol. Jul. 2003;10(7):645-54.
Huang et al., Three-dimensional super-resolution imaging by stochastic optical reconstruction microscopy. Science. Feb. 8, 2008;319(5864):810-3. doi: 10.1126/science.1153529. Epub Jan. 3, 2008.
Iinuma et al., Polyhedra self-assembled from DNA tripods and characterized with 3D DNA-PAINT. Science. Apr. 4, 2014;344(6179):65-9. doi: 10.1126/science.1250944. Epub Mar. 13, 2014.
Jin et al., Metallized DNA nanolithography for encoding and transferring spatial information for graphene patterning. Nat Commun. 2013;4:1663. doi: 10.1038/ncomms2690.
Jones et al., Nanomaterials. Programmable materials and the nature of the DNA bond. Science. Feb. 20, 2015;347(6224):1260901. doi:10.1126/science.1260901.
Jungmann et al., DNA origami-based nanoribbons: assembly, length distribution, and twist. Nanotechnology. Jul. 8, 2011;22(27):275301. doi: 10.1088/0957-4484/22/27/275301. Epub May 20, 2011.
Jungmann et al., Multiplexed 3D cellular super-resolution imaging with DNA-PAINT and Exchange-Paint. Nat Methods. Mar. 2014;11(3):313-8. doi: 10.1038/nmeth.2835. Epub Feb. 2, 2014.
Jungmann et al., Single-molecule kinetics and super-resolution microscopy by fluorescence imaging of transient binding on DNA origami. Nano Lett. Nov. 10, 2010;10(11):4756-61. doi:10.1021/nl103427w.
Kao et al., Tracking of single fluorescent particles in three dimensions: use of cylindrical optics to encode particle position. Biophys J. Sep. 1994;67(3):1291-300.
Ke et al., A study of DNA tube formation mechanisms using 4-, 8-, and 12-helix DNA nanostructures. J Am Chem Soc. Apr. 5, 2006;128(13):4414-21.
Ke et al., DNA brick crystals with prescribed depths. Nat Chem. Nov. 2014;6(11):994-1002. doi: 10.1038/nchem.2083. Epub Oct. 19, 2014.
Ke et al., Multilayer DNA origami packed on a square lattice. J Am Chem Soc. Nov. 4, 2009;131(43):15903-8. doi:10.1021/ja906381y.
Ke et al., Multilayer DNA origami packed on hexagonal and hybrid lattices. J Am Chem Soc. Jan. 25, 2012;134(3):1770-4. doi:10.1021/ja209719k. Epub Jan. 13, 2012.
Ke et al., Scaffolded DNA origami of a DNA tetrahedron molecular container. Nano Lett. Jun. 2009;9(6):2445-7. doi:10.1021/nl901165f.
Ke et al., Three-dimensional structures self-assembled from DNA bricks. Science. Nov. 30, 2012;338(6111):1177-83. doi: 10.1126/science.1227268.
Ke, Designer three-dimensional DNA architectures. Curr Opin Struct Biol. Aug. 2014;27:122-8. doi: 10.1016/j.sbi.2014.07.010. Epub Aug. 11, 2014.
Killops et al., Robust, efficient, and orthogonal synthesis of dendrimers via thiol-ene "click" chemistry. J Am Chem Soc. Apr. 16, 2008;130(15):5062-4. doi: 10.1021/ja8006325. Epub Mar. 20, 2008.
Kuzuya et al., DNA origami: fold, stick, and beyond. Nanoscale. Mar. 2010;2(3):310-22. doi: 10.1039/b9nr00246d. Epub Nov. 24, 2009.
Kuzuya et al., Six-helix and eight-helix DNA nanotubes assembled from half-tubes. Nano Lett. Jun. 2007;7(6):1757-63. Epub May 15, 2007.
Kuzyk et al., DNA-based self-assembly of chiral plasmonic nanostructures with tailored optical response. Nature. Mar. 14, 2012;483(7389):311-4. doi:10.1038/nature10889.
Langecker et al., Synthetic lipid membrane channels formed by designed DNA nanostructures. Science. Nov. 16, 2012;338(6109):932-6. doi: 10.1126/science.1225624.
Le et al., DNA-Templated Self-Assembly of Metallic Nanocomponent Arrays on a Surface. Nano Lett. 2004;4(12):2343-7.
Lee et al., Rate and molecular spectrum of spontaneous mutations in the bacterium *Escherichia coli* as determined by whole-genome sequencing. Proc Natl Acad Sci U S A. Oct. 9, 2012;109(41):E2774-83. doi: 10.1073/pnas.1210309109. Epub Sep. 18, 2012.
Leontis et al., Self-assembled RNA nanostructures. Science. Aug. 15, 2014;345(6198):732-3. doi:10.1126/science.1257989.
Li et al., A replicable tetrahedral nanostructure self-assembled from a single DNA strand. J Am Chem Soc. Sep. 16, 2009;131(36):13093-8. doi: 10.1021/ja903768f.
Li et al., Nucleic acid-based nanoengineering: novel structures for biomedical applications. Interface Focus. Oct. 6, 2011;1(5):702-24. doi: 10.1098/rsfs.2011.0040. Epub Jun. 28, 2011.
Li et al., Single-chain antibodies against DNA aptamers for use as adapter molecules on DNA tile arrays in nanoscale materials organization. Org Biomol Chem. Sep. 21, 2006;4(18):3420-6. Epub Jul. 28, 2006.
Liedl et al., Self-assembly of three-dimensional prestressed tensegrity structures from DNA. Nat Nanotechnol. Jul. 2010;5(7):520-4. doi: 10.1038/nnano.2010.107. Epub Jun. 20, 2010.
Lin et al., DNA tile based self-assembly: building complex nanoarchitectures. Chemphyschem. Aug. 11, 2006;7(8):1641-7.
Lin et al., In vivo cloning of artificial DNA nanostructures. Proc Natl Acad Sci U S A. Nov. 18, 2008;105(46):17626-31. doi: 10.1073/pnas.0805416105. Epub Oct. 16, 2008.
Lin et al., Mirror image DNA nanostructures for chiral supramolecular assemblies. Nano Lett. Jan. 2009;9(1):433-6. doi:10.1021/nl803328v.
Lin et al., Submicrometre geometrically encoded fluorescent barcodes self-assembled from DNA. Nat Chem. 2012;4:832-9.
Linko et al., The enabled state of DNA nanotechnology. Curr Opin Biotechnol. Aug. 2013;24(4):555-61. doi: 10.1016/j.copbio.2013.02.001. Epub Apr. 6, 2013.
Liu et al., Approaching the limit: can one DNA oligonucleotide assemble into large nanostructures? Angew Chem Int Ed Engl. Mar. 13, 2006;45(12):1942-5.
Liu et al., Crystalline two-dimensional DNA-origami arrays. Angew Chem Int Ed Engl. Jan. 3, 2011;50(1):278-81. doi:10.1002/anie.201005911.
Liu et al., DNA nanotubes self-assembled from triple-crossover tiles as templates for conductive nanowires. Proc Natl Acad Sci U S A. Jan. 20, 2004;101(3):717-22. Epub Jan. 6, 2004.
Liu et al., Tensegrity: construction of rigid DNA triangles with flexible four-arm DNA junctions. J Am Chem Soc. Mar. 3, 2004;126(8):2324-5.
Liu et al., Three-dimensional plasmon rulers. Science. Jun. 17, 2011;332(6036):1407-10. doi:10.1126/science.1199958.

(56) References Cited

OTHER PUBLICATIONS

Ma et al., Biotemplated nanostructures: directed assembly of electronic and optical materials using nanoscale complementarily. Journal of Materials Chemistry. 2008;18(9):954-64.
Mansfield, Are there knots in proteins? Nat Struct Biol. Apr. 1994;1(4):213-4.
Mao et al, Designed Two-Dimensional DNA Holliday Junction Arrays Visualized by Atomic Force Microscopy. J. Am. Chem. Soc., 1999,121 (23), pp. 5437-5443.
Marchi et al, Toward larger DNA origami. Nano Lett. Oct. 8, 2014;14(10):5740-7. doi: 10.1021/nl502626s. Epub Sep. 8, 2014.
Mathieu et al., Six-helix bundles designed from DNA. Nano Lett. Apr. 2005;5(4):661-5.
Matsui et al., Focused ion beam applications to solid state devices. Nanotechnology 1996, 7(3):247.
Melosh et al., Ultrahigh-density nanowire lattices and circuits. Science. Apr. 4, 2003;300(5616):112-5. Epub Mar. 13, 2003.
Mitchell et al., Self-assembly of chiral DNA nanotubes. J Am Chem Soc. Dec. 22, 2004;126(50):16342-3.
Monson et al., DNA-Templated Constructed of Copper Nanowires. Nano Letters. 2003;3(2):359-63. Epub Feb. 14, 2003.
Nie et al., Self-assembly of DNA nanoprisms with only two component strands. Chem Commun (Camb). Apr. 7, 2013;49(27):2807-9. doi:10.1039/c3cc39177a.
O'Neill et al., Sturdier DNA nanotubes via ligation. Nano Lett. Jul. 2006;6(7):1379-83.
Park et al., Finite-size, fully addressable DNA tile lattices formed by hierarchical assembly procedures. Angew Chem Int Ed Engl. Jan. 23, 2006;45(5):735-9. Erratum in: Angew Chem Int Ed Engl. Oct. 13, 2006;45(40):6607.
Park et al., Programmable DNA self-assemblies for nanoscale organization of ligands and proteins. Nano Lett. Apr. 2005;5(4):729-33.
Park et al., Three-helix bundle DNA tiles self-assemble into 2D lattice or 1D templates for silver nanowires. Nano Lett. Apr. 2005;5(4):693-6.
Petty et al., DNA-templated Ag nanocluster formation. J Am Chem Soc. Apr. 28, 2004;126(16):5207-12.
Pieles et al., Psoralen covalently linked to oligodeoxyribonucleotides: synthesis, sequence specific recognition of DNA and photo-cross-linking to pyrimidine residues of DNA. Nucleic Acids Res. Jan. 11, 1989;17(1):285-99.
Piner et al,. "Dip-Pen" nanolithography. Science. Jan. 29, 1999;283(5402):661-3.
Pinheiro et al., Challenges and opportunities for structural DNA nanotechnology. Nat Nanotechnol. Nov. 6, 2011;6(12):763-72. doi:10.1038/nnano.2011.187.
Qi et al., A three-dimensional optical photonic crystal with designed point defects. Nature. Jun. 3, 2004;429(6991):538-42.
Qian et al., Scaling up digital circuit computation with DNA strand displacement cascades. Science. Jun. 3, 2011;332(6034):1196-201. doi:10.1126/science.1200520.
Rajendran et al., Photo-cross-linking-assisted thermal stability of DNA origami structures and its application for higher-temperature self-assembly. J Am Chem Soc. Sep. 21, 2011;133(37):1448891. doi:10.1021/ja204546h. Epub Aug. 29, 2011.
Rajesh et al,. Carbon Nanotubes Generated from Template Carbonization of Polyphenyl Acetylene as the Support for Electrooxidation of Methanol. J. Phys. Chem. B, 2003, 107 (12), pp. 2701-2708.
Randolph et al., Focused, Nanoscale Electron-Beam-Induced Deposition and Etching. Critical Reviews in Solid State and Material Sciences, 2006, 31(3):55-89.
Ravanat et al., Direct and indirect effects of UV radiation on DNA and its components. J Photochem Photobiol B. Oct. 2001;63(1-3):88-102.
Reif et al., Compact error-resilient computational DNA tiling assemblies. Proceeding DNA'04 Proceedings of the 10th international conference on DNA computing. 2004:293-307.
Reif et al., Complexity of graph self-assembly in accretive systems and self-destructible systems. Journal Theoretical Computer Science. 2011;412(17):1592-605.
Rothemund et al., Algorithmic Self-Assembly of DNA Sierpinski Triangles. PLoS Biology. 2004. 2004;2(12):e424. doi:10.1371/journal.pbio.0020424.
Rothemund et al., Design and characterization of programmable DNA nanotubes. J Am Chem Soc. Dec. 22, 2004;126(50):16344-52. Erratum in: J Am Chem Soc. Feb. 20, 2013;135(7):2864.
Rothemund et al., the program-size complexity of self-assembled squares. Extended Abstract. Proceeding STOC '00 Proceedings of the thirty-second annual ACM symposium on Theory of computing. ACM 2000:459-68.
Rothemund, Folding DNA to create nanoscale shapes and patterns. Nature. Mar. 16, 2006;440(7082):297-302.
Sahu et al., A self-assembly model of time-dependent glue strength. DNA'05 Proceedings of the 11th international conference on DNA Computing. 2005:290-304.
Scheible et al., A Compact DNA Cube with Side Length 10 nm. Small. Oct. 21, 2015;11(39):5200-5. doi: 10.1002/smll.201501370. Epub Aug. 21, 2015.
Schmied et al., DNA origami nanopillars as standards for three-dimensional superresolution microscopy. Nano Lett. Feb. 13, 2013;13(2):781-5. doi: 10.1021/nl304492y. Epub Feb. 5, 2013.
Schulman et al., Synthesis of crystals with a programmable kinetic barrier to nucleation. Proc Natl Acad Sci USA. Sep. 25, 2007;104(39):15236-41. Epub Sep. 19, 2007.
Schweller et al., Multiplexed in situ immunofluorescence using dynamic DNA complexes. Angew Chem Int Ed Engl. Sep. 10, 2012;51(37):9292-6. doi: 10.1002/anie.201204304. Epub Aug. 15, 2012.
Seelig et al., Enzyme-free nucleic acid logic circuits. Science. Dec. 8, 2006;314(5805):1585-8.
Seeman et al., Nucleic acid nanostructures: Bottom-up control of geometry on the nanoscale. Rep. Prog. Phys, 2005, 68: 237-70.
Seeman et al., The design and engineering of nucleic acid nanoscale assemblies. Curr Opin Struct Biol. Aug. 1996;6(4):519-26.
Seeman, De novo design of sequences for nucleic acid structural engineering. J Biomol Struct Dyn. Dec. 1990;8(3):573-81.
Seeman, DNA in a material world. Nature. Jan. 23, 2003;421(6921):427-31.
Seeman, Nanomaterials based on DNA. Annu Rev Biochem. 2010;79:65-87. doi:10.1146/annurev-biochem-060308-102244.
Seeman, Nucleic acid junctions and lattices. J Theor Biol. Nov. 21, 1982;99(2):237-47.
Sekulic et al., A direct linkage between the phosphoinositide 3-kinase-AKT signaling pathway and the mammalian target of rapamycin in mitogen-stimulated and transformed cells. Cancer Res. Jul. 1, 2000;60(13):3504-13.
Sharma et al., Control of self-assembly of DNA tubules through integration of gold nanoparticles. Science. Jan. 2, 2009;323(5910):112-6. doi: 10.1126/science.1165831.
Sharma et al., DNA-tile-directed self-assembly of quantum dots into two-dimensional nanopatterns. Angew Chem Int Ed Engl. 2008;47(28):5157-9. doi:10.1002/anie.200801485.
Sharma et al., Toward reliable gold nanoparticle patterning on self-assembled DNA nanoscaffold. J Am Chem Soc. Jun. 25, 2008;130(25):7820-1. doi: 10.1021/ja802853r. Epub May 30, 2008.
Sharonov et al., Wide-field subdiffraction imaging by accumulated binding of diffusing probes. Proc Natl Acad Sci U S A. Dec 12, 2006;103(50):18911-6. Epub Dec. 1, 2006.
Sherman et al., A Precisely Controlled DNA Biped Walking Device. Nano Letters. 2004;4(7):1203-7.
Shih et al., A 1.7-kilobase single-stranded DNA that folds into a nanoscale octahedron. Nature. Feb. 12, 2004;427(6975):618-21.
Shih et al., Knitting complex weaves with DNA origami. Curr Opin Struct Biol. Jun. 2010;20(3):276-82. doi: 10.1016/j.sbi.2010.03.009. Epub Apr. 22, 2010.
Shtengel et al., Interferometric fluorescent super-resolution microscopy resolves 3D cellular ultrastructure. Proc Natl Acad Sci U S A. Mar. 3, 2009;106(9):3125-30. doi:10.1073/pnas.0813131106. Epub Feb. 6, 2009.

(56) References Cited

OTHER PUBLICATIONS

Smith et al., A structurally variable hinged tetrahedron framework from DNA origami. J Nucleic Acids. 2011;2011:360954. doi: 10.4061/2011/360954. Epub Sep. 18, 2011.
Surwade et al., Molecular lithography through DNA-mediated etching and masking of SiO2. J Am Chem Soc. Aug. 10, 2011;133(31):11868-71. doi: 10.1021/ja2038886. Epub Jul. 19, 2011.
Surwade et al., Nanoscale growth and patterning of inorganic oxides using DNA nanostructure templates. J Am Chem Soc. May 8, 2013;135(18):6778-81. doi: 10.1021/ja401785h. Epub Apr. 25, 2013.
Takusagawa et al., A Real Knot in Protein. J. Am. Chem. Soc., 1996, 118 (37), pp. 8945-8946.
Tang et al., Evolution of block copolymer lithography to highly ordered square arrays. Science. Oct. 17, 2008;322(5900):429-32. doi: 10.1126/science.1162950. Epub Sep. 25, 2008.
Tavakkoli et al., Templating three-dimensional self-assembled structures in bilayer block copolymer films. Science. Jun. 8, 2012;336(6086):1294-8. doi: 10.1126/science.1218437.
Taylor, A deeply knotted protein structure and how it might fold. Nature. Aug. 24, 2000;406(6798):916-9.
Tørring et al., DNA origami: a quantum leap for self-assembly of complex structures. Chem Soc Rev. Dec. 2011;40(12):5636-46. doi: 10.1039/c1cs15057j. Epub May 19, 2011.
Venkataraman et al., Selective cell death mediated by small conditional RNAs. Proc Natl Acad Sci U S A. Sep. 28, 2010;107(39):16777-82. doi: 10.1073/pnas.1006377107. Epub Sep. 7, 2010. Retraction in: Dirks RM, Ueda CT, Pierce NA. Proc Natl Acad Sci U S A. Jan. 2, 2013;110(1):384.
Wagner et al., A light-sensing knot revealed by the structure of the chromophore-binding domain of phytochrome. Nature. Nov. 17, 2005;438(7066):325-31.
Wei et al., Complex shapes self-assembled from single-stranded DNA tiles. Nature. May 30, 2012;485(7400):623-6. doi: 10.1038/nature11075.
Wei et al., Uniquimer: Software of De Novo DNA Sequence Generation for DNA Self-Assembly—An Introduction and the Related Applications in DNA Self-Assembly. J Comput Theor Nanosci. 2007;4(1):133-41.
Williams et al,. Tiamat: A Three-Dimensional Editing Tool for Complex DNA Structures. DNA Computing 2009, 90-101.
Winfree et al., Design and self-assembly of two-dimensional DNA crystals. Nature. Aug. 6, 1998;394(6693):539-44.
Winfree, Algorithmic Self-Assembly of DNA. Doctoral Thesis. California Institute of Technology. Mar. 1998.
Winters et al., Surface science aspects of etching reactions. Surface Science Reports. 1992, 14(4-6): 162-269.
Woo et al., Programmable molecular recognition based on the geometry of DNA nanostructures. Nat Chem. Jul. 10, 2011;3(8):620-7. doi: 10.1038/nchem.1070. Erratum in: Nat Chem. Oct. 2011;3(10):829. Nat Chem. 2011;3(8):following 627.
Wu et al., High aspect ratio silicon etch: A review. Journal of Applied Physics, 2010, 108(5): 051101-051101-20.
Xiao et al., Selfassembly of Metallic Nanoparticle Arrays by DNA Scaffolding. Journal of Nanoparticle Research. Aug. 1, 2002;4:313-7.
Yan et al., A robust DNA mechanical device controlled by hybridization topology. Nature. Jan. 3, 2002;415(6867):62-5.
Yan et al., Directed nucleation assembly of DNA tile complexes for barcode-patterned lattices. Proc Natl Acad Sci U S A. Jul. 8, 2003;100(14):8103-8. Epub Jun. 23, 2003.
Yan et al., DNA-templated self-assembly of protein arrays and highly conductive nanowires. Science. Sep. 26, 2003;301(5641):1882-4.
Yang et al., Artificially expanded genetic information system: a new base pair with an alternative hydrogen bonding pattern. Nucleic Acids Res. 2006;34(21):6095-101. Epub Oct. 29, 2006.
Yang et al., DNA Origami with Double-Stranded DNA as a Unified Scaffold. ACS Nano, 2012, 6(9): 8209-8215.
Yang et al., Metal-nucleic acid cages. Nat Chem. Aug. 2009;1(5):390-6. doi: 10.1038/nchem.290.
Yevdokimov et al., Nanoconstructions based on double-stranded nucleic acids. Int J Biol Macromol. Jul. 2005;36(1-2):103-15.
Yin et al., A unidirectional DNA walker that moves autonomously along a track. Angew Chem Int Ed Engl. Sep. 20, 2004;43(37):4906-11.
Yin et al., Designs of autonomous unidirectional walking DNA devices. Proceeding DNA'04 Proceedings of the 10th international conference on DNA computing. 2004:410-25.
Yin et al., Programming biomolecular self-assembly pathways. Nature. Jan. 17, 2008;451(7176):318-22. doi: 10.1038/nature06451.
Yin et al., Programming DNA tube circumferences. Science. Aug. 8, 2008;321(5890):824-6.
Yin et al., Theoretical and practical advances in genome halving. Bioinformatics. Apr. 1, 2005;21(7):869-79. Epub Oct. 28, 2004.
Yurke et al., A DNA-fuelled molecular machine made of DNA. Nature. Aug. 10, 2000;406(6796):605-8.
Zhang et al., Conformational flexibility facilitates self-assembly of complex DNA nanostructures. Proc Natl Acad Sci U S A. Aug. 5, 2008;105(31):10665-9. doi:10.1073/pnas.0803841105. Epub Jul. 30, 2008.
Zhang et al., Construction of a DNA-Truncated Octahedron. J Am Chem Soc 1994;116(5):1661-9.
Zhang et al., Structural DNA nanotechnology: state of the art and future perspective. J Am Chem Soc. Aug. 13, 2014;136(32):11198-211. doi:10.1021/ja505101a. Epub Jul. 28, 2014.
Zhang et al., Symmetry controls the face geometry of DNA polyhedra. J Am Chem Soc. Feb. 4, 2009;131(4):1413-5. doi:10.1021/ja809666h.
Zhao et al., Organizing DNA origami tiles into larger structures using preformed scaffold frames. Nano Lett. Jul. 13, 2011;11(7):2997-3002. doi:10.1021/nl201603a. Epub Jun. 23, 2011.
Zheng et al., From molecular to macroscopic via the rational design of a self-assembled 3D DNA crystal. Nature. Sep. 3, 2009;461(7260):74-7. doi:10.1038/nature08274.
Zimmermann et al., Self-assembly of a DNA dodecahedron from 20 trisoligonucleotides with C(3h) linkers. Angew Chem Int Ed Engl. 2008;47(19):3626-30. doi: 10.1002/anie.200702682.
Hung et al., Large-area spatially ordered arrays of gold nanoparticles directed by lithographically confined DNA origami. Nat Nanotechnol. Dec. 2009;5(2):121-6.
Lee et al., SiO$_2$ mask erosion and sidewall composition during CH$_4$/H$_2$ reactive ion etching of InGaAsP/InP. Appl Phys Lett. Dec. 1993;63(23):3170-2.
Ploetz et al., Selective functionalization of patterned glass surfaces. J Mater Chem B. Jan. 2014;2(17):2606-15.

\* cited by examiner

Chiral 3D conformation

Printing to silicon wafer

SCALABLE NUCLEIC ACID-BASED NANOFABRICATION

RELATED APPLICATIONS

This application is a national stage filing under 35 U.S.C. § 371 of international application number PCT/US2015/032198, filed May 22, 2015, which was published under PCT Article 21 (21 in English and claims the benefit under 35 U.S.C. § 119(e) of U.S. provisional application No. 62/157,595, filed May 6, 2015, U.S. provisional application No. 62/079,877, filed Nov. 14, 2014, and U.S. provisional application No. 62/002,117, filed May 22, 2014, each of which is incorporated by reference herein in its entirety.

FEDERALLY SPONSORED RESEARCH

This invention was made with government support under Contract Nos. N00014-11-1-0914, N00014-10-1-0827 and N00014-13-1-0593 awarded by U.S. Department of Defense Office of Naval Research, under W911NF-12-1-0238 awarded by the U.S. Army Research Office, and under CMMI-1333215 awarded by National Science Foundation. The government has certain rights in the invention.

BACKGROUND OF THE INVENTION

Modern electronics and optics require the large-scale integration of small building blocks, such as nanoparticles and nanowires, into specific two-/three-dimensional (2D/3D) architectures. For example, 3D optical communication pathways have been implemented by tuning inter-particle spacing among nanoscale-size components such that only coupled nanoparticles can exchange information to build up high-speed all-optical computation.

Deoxyribonucleic acid (DNA) molecules that readily fold into arbitrary shapes can be used for the fabrication of such 2D-3D architectures (e.g., nanoscale devices), through both DNA-directed self-assembly and nanopatterning processes. Recently, a pattern transfer process, known as DNA lithography, has been used to pattern inorganic substrates using DNA templates as masks. In general, a DNA mask is adsorbed on a substrate, and then the substrate is etched, resulting in a substrate patterned in the shape of the DNA mask. The chemical stability of DNA, however, is limited. To protect the DNA masks from the harsh chemical reaction conditions of etching, the masks are protected with a coating, such as, for example, a metal coating or an oxide coating.

SUMMARY OF THE INVENTION

Provided herein, in some aspects, is a platform that uses substrates such as pre-formed (also referred to as pre-assembled) 2D and/or 3D nucleic acid (e.g., DNA) nano-structures/crystals (e.g., nano- or micro-structures) as global templates for high-resolution fabrication, including programmable nano-manufacturing, of complex 2D and/or 3D architectures from small moieties, such as nanoparticles (e.g., gold nanoparticles) and/or 1D nanowires (e.g., carbon nanotubes or Si nanowires) and/or biomolecules (e.g., proteins and aptamers) at a spatial resolution of at least 1 nm (e.g., 1, 2, 3, 4 or 5 nm, or more). The platform provided herein permits rational integration of, for example, more than 1,000 moieties (homogeneous or heterogeneous populations) into complex prescribed 2D and/or 3D architectures and fundamental one-dimensional (1D) polymeric nanowires and parallel arrays at the aforementioned spatial resolution. The disclosure also provides methods and devices with precision for patterning of at least 0.1 nm across scales from nanometer to wafer scale.

Such nano-manufacturing framework can be used both under lithographic conditions, such as deposition and reactive ion etching, and solution assembly conditions. In addition, the framework provided herein permits rational integration of, for example, more than 50 moieties (including homogeneous or heterogeneous populations) into complex prescribed architectures.

Various aspects of this disclosure relate to (1) epitaxial-grown DNA template; (2) non-covalent deposition of nucleic acid (e.g., DNA) nanostructure (acting as a template) on a substrate such as a wafer; (3) assembly of one or a plurality of nano-moieties on a nucleic acid (e.g., DNA) nanostructure (acting as a template); (4) 3D nucleic acid (e.g., DNA) lithography of a substrate; (5) printing of one or a plurality of nano-moieties functionalized on the nucleic acid nanostructure (acting as a template) to a substrate; and (6) 3D confined deposition using a nucleic acid nanostructure (acting as a template).

The present framework differs from existing top-down lithography photolithography/E-beam lithography approaches because of its high-resolution positioning down to 1 nm, and the one-step patterning capability for complex 3D features. Heterogeneous moieties can also be patterned simultaneously. Compared with block copolymer lithography, the nucleic acid-based (e.g., DNA-based) framework provided herein can be used to create complex irregular asymmetric patterns through self-assembly, with minimal feature defects from thermodynamics. The methods and devices formed using such methods as provided herein allow for complicated global architecture, including symmetric and asymmetric forms. Using single-layered DNA structures, such as DNA tiles and 2D origami, it is also possible to achieve complex patterns in nano-manufacturing.

The platform provided herein also permits the construction of complex nano-component-based devices with profound engineering and technological implications. In photonics, for example, coupled nanoparticles direct the light propagation along specific pathways to exchange information or focus energy. In electronics, as another example, particularly for high-density information storage, coupled nanoparticles store multiple information bits at each specific lateral position. With electronics, particularly with high-density information storage medium, well-aligned isolated nanoparticle arrays enable the single-bit addressability down to a 1 nm scale, and more than 1,000 times storage capacity, relative to the current limit. Further, scalable production of crossbar architecture constructed using the platform, as provided herein, enables industry-level production of transistor arrays from nanoribbons or nanowires, which achieves electronic circuits beyond the limit of, for example, current top-down lithography.

Some aspects of the present disclosure provide substrates having a spatial resolution of 50 nm or less and containing at prescribed locations nucleic acid handles hybridized to complementary nucleic acid anti-handles that are coupled to moieties.

Some aspects of the present disclosure provide devices comprising a substrate having a spatial resolution 50 nm or less and containing at prescribed locations nucleic acid handles hybridized to complementary nucleic acid anti-handles that are coupled to moieties.

Some aspects of the present disclosure provide substrates having a spatial resolution of less than 50 nm and containing at prescribed locations a moiety, wherein the moiety is indirectly coupled to or confined to the substrate through a nucleic acid hybridization interaction, a protein-protein interaction, a hydrophobic interaction, an electrostatic interaction, π-π stacking, spatial confinement or electrophoresis.

Some aspects of the present disclosure provide devices comprising a substrate having a spatial resolution of less than 50 nm and containing at prescribed locations a moiety, wherein the moiety is indirectly coupled to or confined to the substrate through a nucleic acid hybridization interaction, a protein-protein interaction, a hydrophobic interaction, an electrostatic interaction, π-π stacking, spatial confinement or electrophoresis.

Some aspects of the present disclosure provide substrates having a spatial resolution of less than 50 nm and at least one channel, wherein moieties are spatially confined to the at least one channel, and the at least one channel is no wider than twice the diameter (or twice the average diameter) of the moieties. In some embodiments, the at least one channel is no wider than the diameter (or the average diameter) of the moieties.

Some aspects of the present disclosure provide devices comprising a substrate having a spatial resolution of less than 50 nm and at least one channel, wherein moieties are spatially confined to the at least one channel, and the diameter of the at least one channel is no wider than twice the diameter (or average diameter) of the moieties. In some embodiments, the at least one channel is no wider than the diameter (or the average diameter) of the moieties.

Some aspects of the present disclosure provide methods of producing a device, comprising depositing a nucleic acid crystal on a surface of a substrate, and coupling to the nucleic acid crystal at prescribed locations nucleic acid handles complementary to nucleic acid anti-handles that are coupled to moieties.

The present disclosure also provides, in some aspects, a high-resolution nucleic acid (e.g., DNA) lithography platform for use in fabricating diverse substrates (e.g., inorganic and organic substrates) into arbitrary, complex two- and three-dimensional objects. Unlike current nucleic acid lithography techniques, the methods provided herein use "bare" nucleic acid nanostructures, without any surface coating (e.g., without a metal or oxide coating), as masks to achieve prescribed two- and three-dimensional patterns with, for example, 1 nanometer (nm) to 1 μm feature resolution.

In some embodiments, a bare nucleic acid nanostructure is assembled from single-stranded nucleic acid (e.g., single-stranded DNA). In some embodiments, a bare nucleic acid nanostructure is assembled from synthetic single-stranded oligonucleotides (e.g., synthetic single-stranded DNA oligonucleotides). A bare nucleic acid nanostructure may also be assembled from single-stranded oligonucleotides (e.g., single-stranded DNA oligonucleotides) isolated from naturally-occurring nucleic acid (e.g., DNA). It should be understood, however, that any bare nucleic acid (e.g., DNA) nanostructure assembled from isolated nucleic acid (e.g., DNA) is considered an artificial structure, as the nucleic acid (e.g., DNA) nanostructures contemplated herein include nucleic acid that is not naturally occurring. It should also be understood that components of nucleic acid nanostructures of the present disclosure may, in some instances, include a combination of non-naturally-occurring and naturally-occurring nucleic acid.

In some embodiments, a bare nucleic acid (e.g., DNA) nanostructure is assembled from at least 50 synthetic single-stranded heterogeneous oligonucleotides.

In some embodiments, a bare nucleic acid (e.g., DNA) nanostructure is assembled from a single-stranded nucleic acid (e.g., DNA) with a length of at least 1 kilobase.

In some embodiments, methods of the present disclosure do not include a metal, a metal oxide or an oxide growth step(s). A growth step (e.g., metal growth step(s)) refers to a shape-conserving step(s) by which particles (e.g., metal particles such as, for example, Au particles) are deposited/adsorbed onto the surface of a nucleic acid nanostructure, the resulting structure (e.g., metal structure) inheriting its shape from the nucleic acid template (see, e.g., Surwade S. P. et al. *J. Am. Chem. Soc.* 133: 11868, 2011; and Jin Z. et al. *Nature Communications,* 4: 1663, 2013 incorporated by reference herein). When using a metal growth step(s), such resulting structures may be referred to as "metallized" structures (e.g., metallized DNA).

In some embodiments, an adsorption step comprises adsorbing onto the surface of the substrate a solution that comprises a bare nucleic acid (e.g., DNA) nanostructure.

In some embodiments, a bare nucleic acid nanostructure is functionalized with metal nanoparticles, metal clusters, oxides, chalcogenides, nanowires, polymers and/or biomolecules. In some embodiments, a bare DNA nanostructure is functionalized with gold nanoparticles. It should be understood that "functionalizing" a bare nucleic acid nanostructure is distinguished from "metallizing" a bare nucleic acid nanostructure. The materials (e.g., metal nanoparticles) used to functionalize a bare nucleic acid nanostructure do no serve to protect the bare DNA nanostructure from dry etching conditions. As shown in FIGS. 8 and 9, a three-dimensional DNA nanostructure is functionalized with a gold film (FIG. 8) or gold nanoparticles (FIG. 9A-B) such that during the etching process, the gold particles are transferred to the patterned substrate—the resulting patterned substrate is now considered "functionalized."

Some aspects of the present disclosure provide patterned substrates produced by any of the methods provided herein.

Some aspects of the present disclosure provide devices that comprise any of the patterned substrates provided herein. For example, a device of the present disclosure may be an electronic device, a plasmonic device, a photonic device, a photovoltaic device or a hybrid device.

In some embodiments, substrates produced using the DNA lithography methods as provided herein are used as global templates for high-resolution fabrication of complex 2D and/or 3D architectures from small moieties, such as nanoparticles (e.g., gold nanoparticles) and/or 1D nanowires (e.g., carbon nanotubes) at a spatial resolution of at least 1 nm (e.g., 1, 2, 3, 4 or 5 nm, or more).

BRIEF DESCRIPTION OF THE DRAWINGS

The accompanying drawings are not intended to be drawn to scale. For purposes of clarity, not every component may be labeled in every drawing.

FIG. 1A shows a design schematic for aligning gold nanoparticles onto DNA crystals. Single-stranded DNA tiles (16 to 48 nucleotides long) were incubated under staged isothermal conditions to create DNA crystals with prescribed 3D DNA handle patterns. The cuboid represents a unit cell of a DNA crystal. The strand-like structures represent DNA handles. Gold nanoparticles (spheres) modified with single-stranded anti-handles were then added to form the designed nanoparticle architecture. FIG. 1B shows a schematic drawing of 2D-3D nanoparticle architectures created on DNA crystals. The top left schematic shows parallel arrays of 8-nm gold nanoparticle chains. The top right schematic shows parallel arrays of alternative 8-nm and 13-nm gold nanoparticle chains. The bottom left schematic shows two-layer 3D architecture with arrays of 13-nm gold nanoparticles chains beneath and arrays of 8-nm gold nanoparticles chains on the top. The bottom right schematic shows three-layer 3D architecture with arrays of 13-nm gold nanoparticles chains beneath, one chain of 13-nm gold particles in the middle, and one chain of 40-nm fluorescence nanobeads (or nanoparticles) on the top. Light gray spheres represent gold nanoparticle (small for 8 nm; large for 13 nm) assembled on top of a DNA crystal. Small dark gray spheres represent 13-nm gold nanoparticles decorated beneath a DNA crystal. Large dark gray spheres represent 40-nm fluorescent nanobeads. The scale bar is 100 nm.

DETAILED DESCRIPTION OF THE INVENTION

Modern electronics and optics require the large-scale integration of small building blocks into specific 2D and/or 3D architectures. However, the resolution for small nanoparticles below 10 nm is challenging using traditional top-down and bottom-up approaches. As provided herein, using, for example, a pre-formed nano-scale or micro-scale 3D DNA nanostructure/crystal as a global template, complex 2D/3D architectures are fabricated from small moieties (e.g., nanoparticles and/or carbon nanotube) at a spatial resolution of, for example, 2 nm to 2 μm. High-resolution alignment using the methods as provided herein ensures strong coupling among moieties at prescribed locations/directions. Additionally, robust assembly of moieties onto DNA nanostructures/crystals and other substrates improves the reproducibility of self-assembled 3D architectures through isolation from local interactions of information about global architecture. This feature minimizes local perturbation. Defects at each single position, either absence or duplication, will not cascade into down-streaming assemblies due to the absence of direct particle-particle local interactions.

Figure 3A:
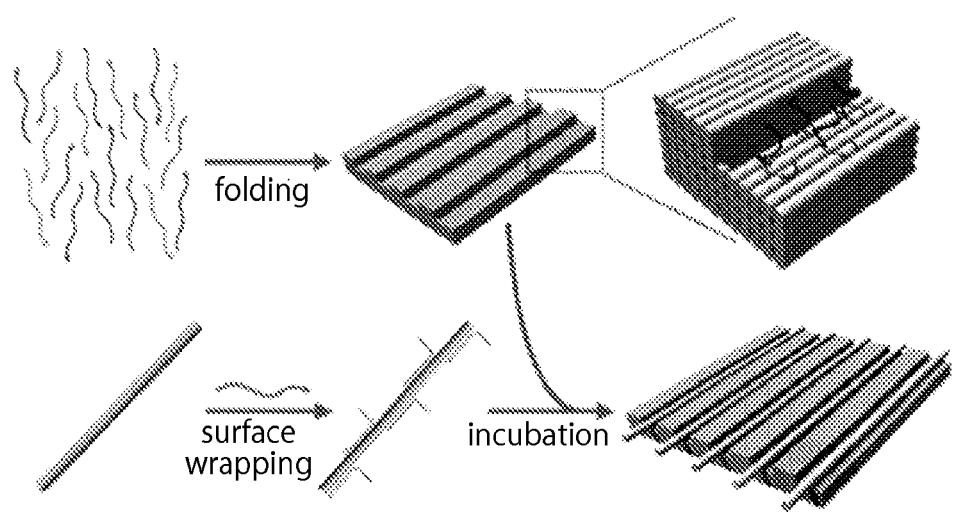
FIG. 3A shows a design scheme for carbon nanotubes (CNTs) patterned within DNA trenches.
Figure 3B:
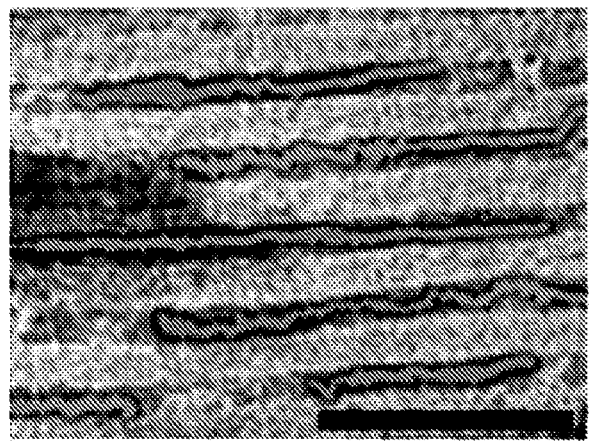
FIG. 3B shows a transmission electron microscopy (TEM) image for CNTs patterned within DNA trenches. In the transmission electron microscopy (TEM) image, CNTs on DNA crystal have been artificially colored to increase contrast. Scale bar is 100 nm.
Figure 3C:
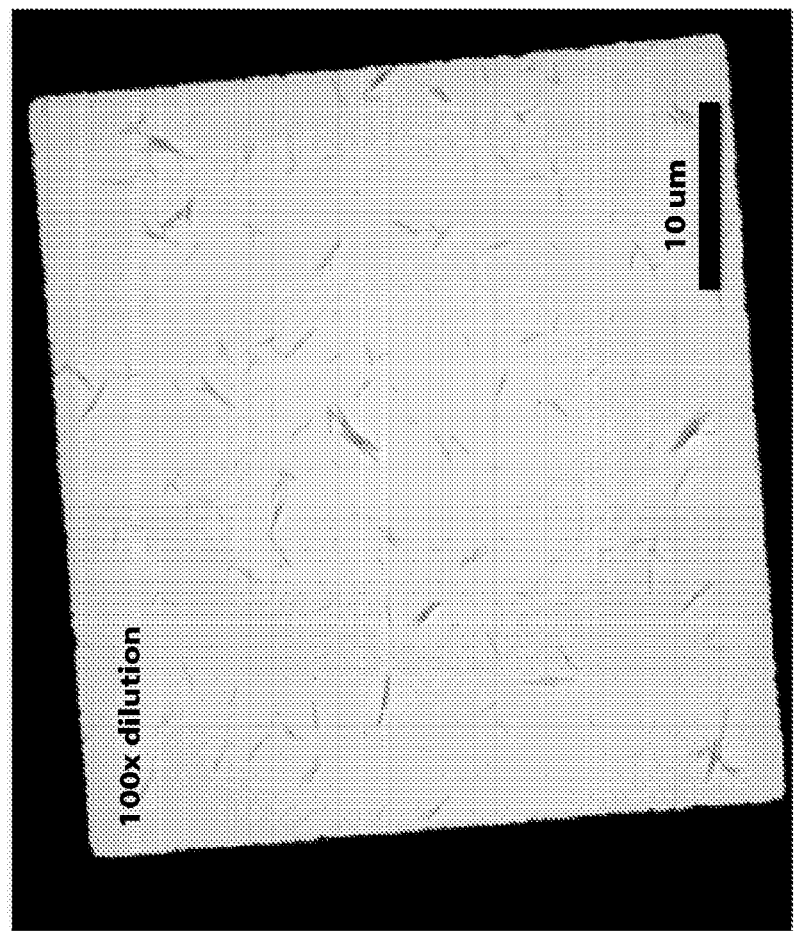
FIG. 3C shows an example of CNT alignment with 24 nm pitch (center-to-center spacing between two adjacent CNTs) dimension. Top left shows a TEM image of multiple CNTs patterned within DNA trenches. The light gray line is a CNT (marked with an arrow indicating CNT). The gray bundles are DNA ridges that confine CNT patterning. The scale bar is 100 nm. Bottom left is the zoom-in view of the selected region in the top left panel. The light gray line is a CNT (marked with an arrow indicating CNT). Gray bundles are DNA ridges that confine CNT patterning. Right panel is the zoom-out TEM image for the CNT-decorated DNA crystal sample. The peripheral black regions are the copper lines on the TEM sample grid. The gray regions on the white background are the CNT-decorated DNA crystal. The scale bar is 10 um.
Figure 3C:
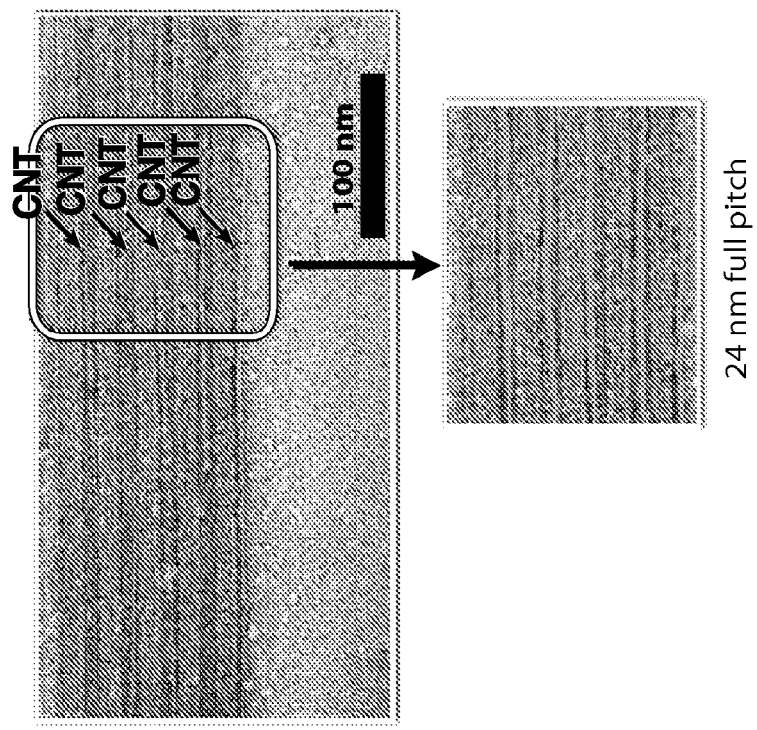
Figure 3D:
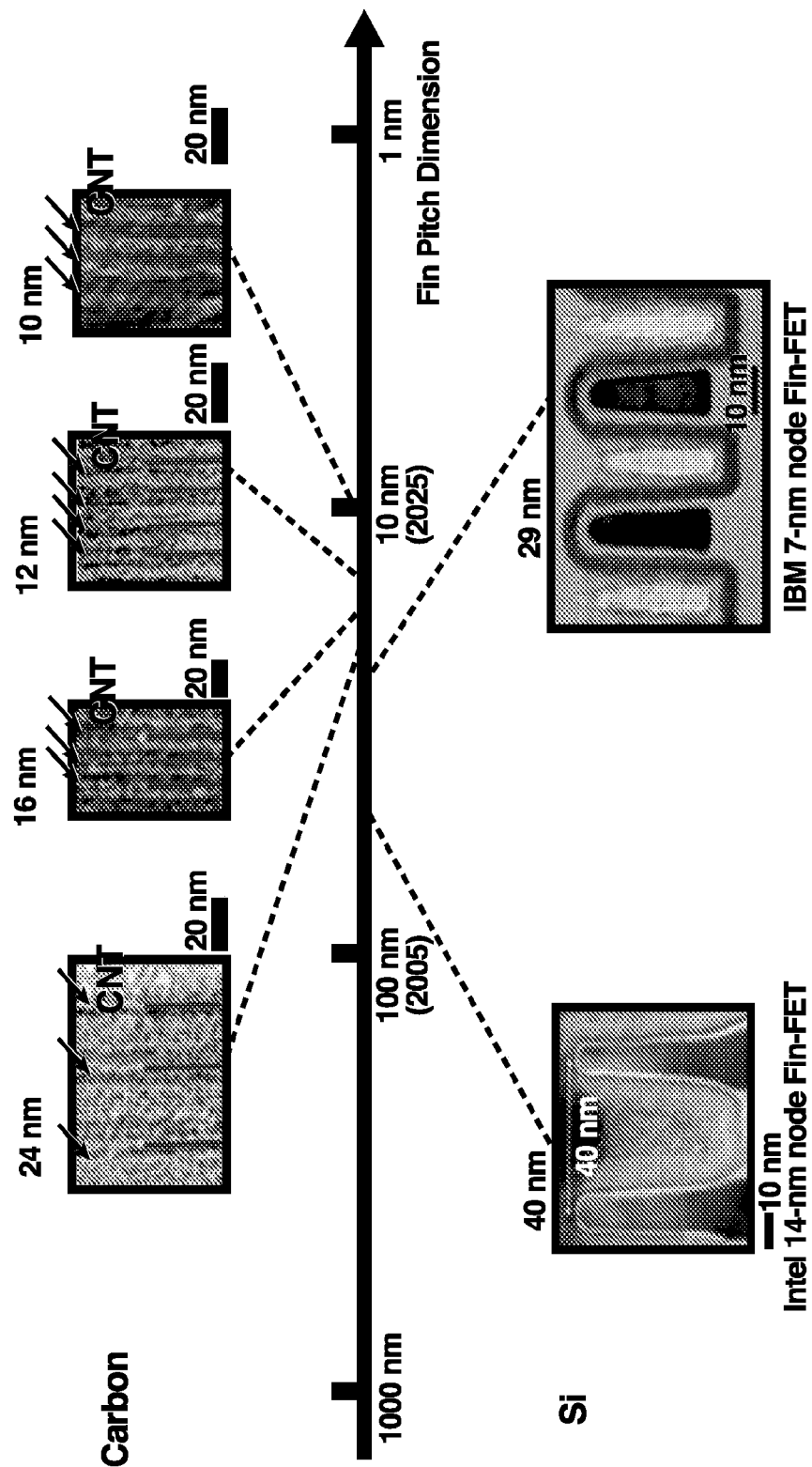
FIG. 3D shows the scaling of CNT arrays on a DNA crystal template. The scale bar is pitch dimension in field-effect transistors (i.e., the spacing between two adjacent lines in a transistor). Panels on top of the scale bar are the TEM images for CNT arrays, patterned on DNA crystals templates, with different prescribed pitches. By using a DNA crystal with different periodicity, CNT arrays are manufactured with tunable pitches from 24 nm to 10 nm. Within each TEM image, the marked lines are CNTs, while the white bundles are DNA templates. The scale bar is 20 nm. Below the scale bar are SEM images for current Si-based field-effect transistors. At the left is Intel's 14-nm node transistor. The dark regions are Si trenches, while the light gray region is the oxide coating and gating medium. At the right is IBM's 7-nm node transistor. The dark regions are Si trenches, while the light gray region and the white region are the oxide coating and the insulator. The dark gray region is the gating medium.

Thus, provided herein are global templates (e.g., nucleic acid templates) that direct and scale the alignment of moieties regardless of their symmetry and local interparticle interactions. For example, one-dimensional nanoparticle chains, two-dimensional arrays with alternative chains and three-dimensional parallel chains are provided herein and can be constructed from both homogenous and heterogeneous particle components, demonstrating a wide versatility for components. Architecture lacking displacement symmetry can also be constructed on the DNA nanostructures/crystals. As another example, spatial confinement can be introduced to assist chemical recognition for precise orientation control in scalable carbon nanotube (CNT) alignment. As shown in the Example 1, 3D nanoscaled grooves with nanometer thicknesses were introduced to spatially confine CNT rotation on the template, ensuring CNTs, captured by the binding sites embedded at the groove bottom, can only adopt the prescribed orientations (FIGS. 3A-B).

Figure 2A:
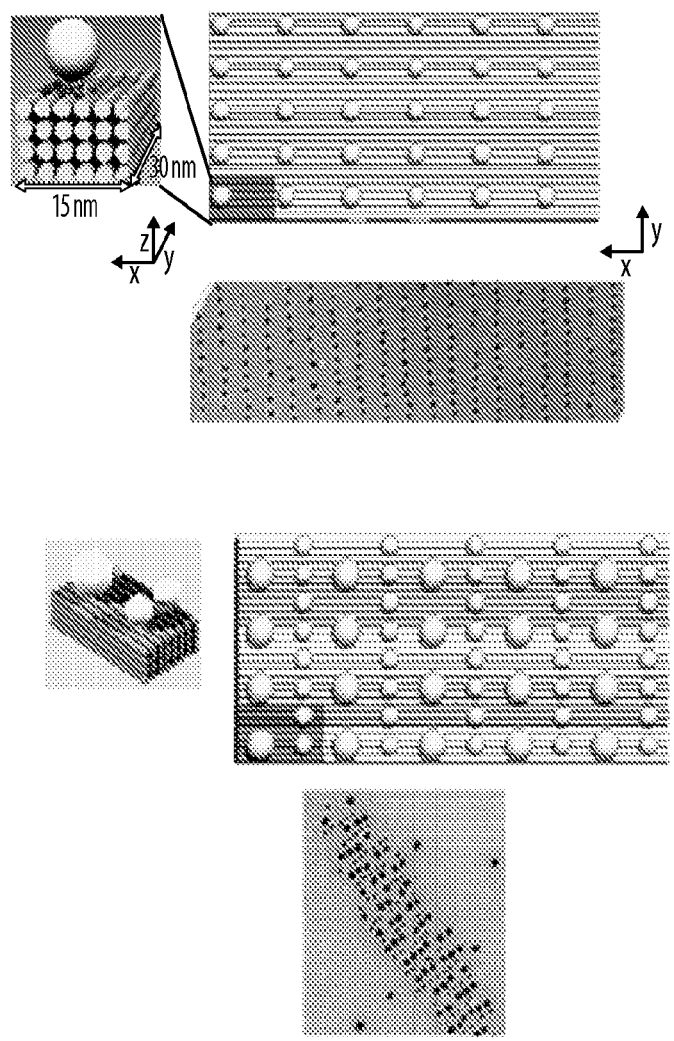
FIGS. 2A-2C show nanoparticles aligned on DNA crystals. Light gray spheres represent gold nanoparticle (small for 8 nm; large for 13 nm) assembled on top of a DNA crystal. Small dark gray spheres represent 13-nm gold nanoparticles decorated beneath a DNA crystal. Large dark gray spheres represent 40-nm fluorescent nanobeads.
Figure 2B:
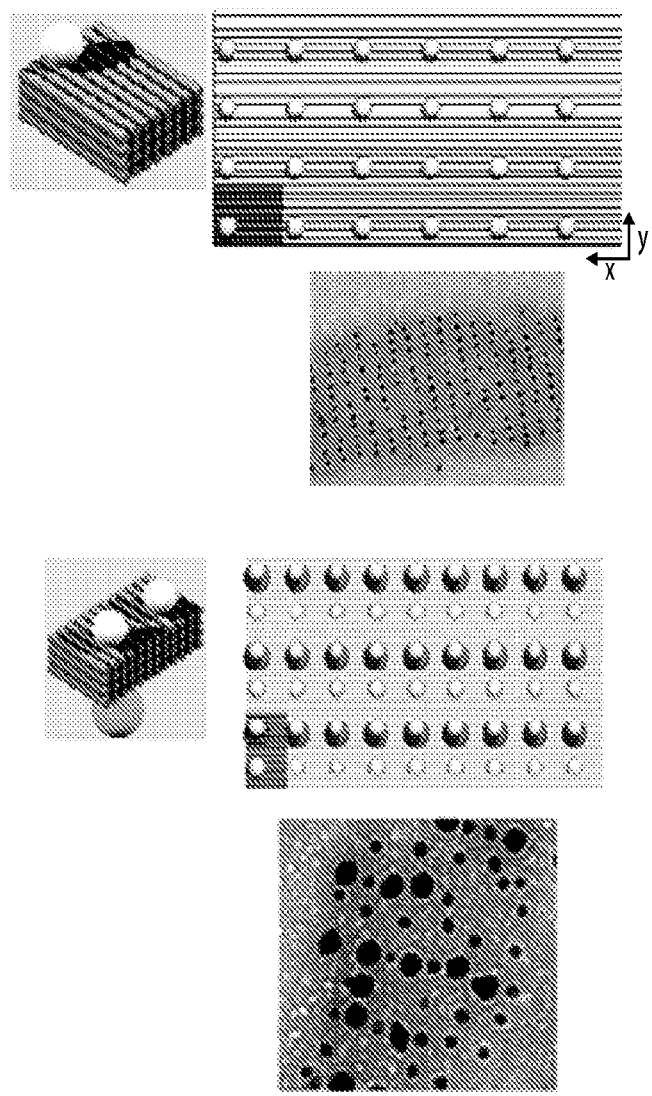
Figure 2C:
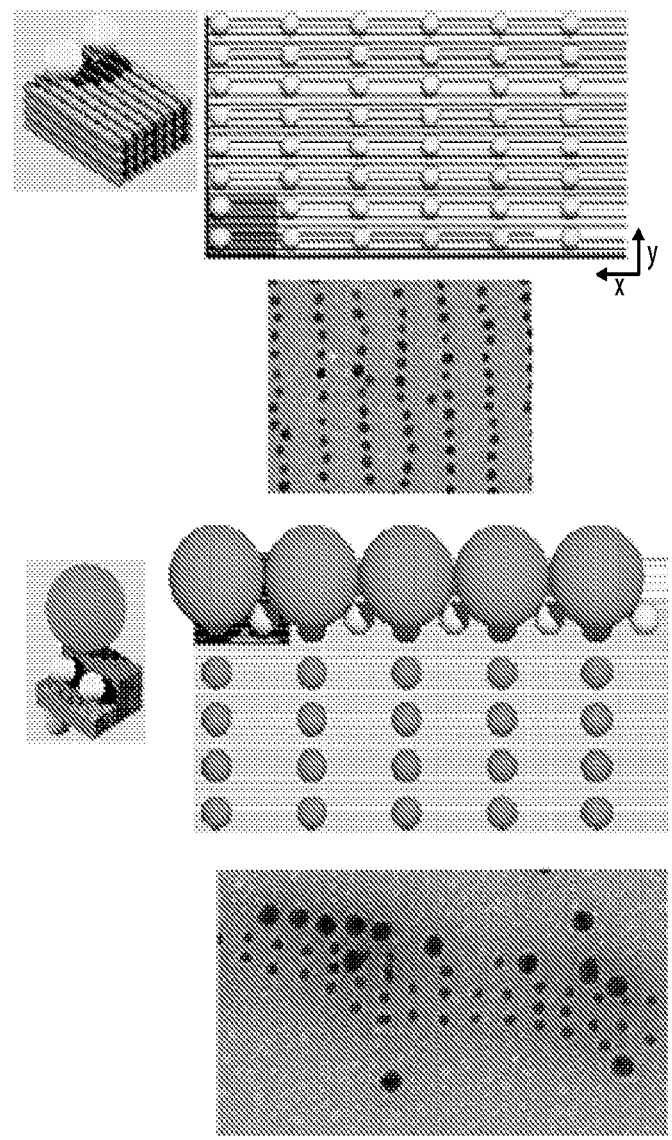
Figure 2D:
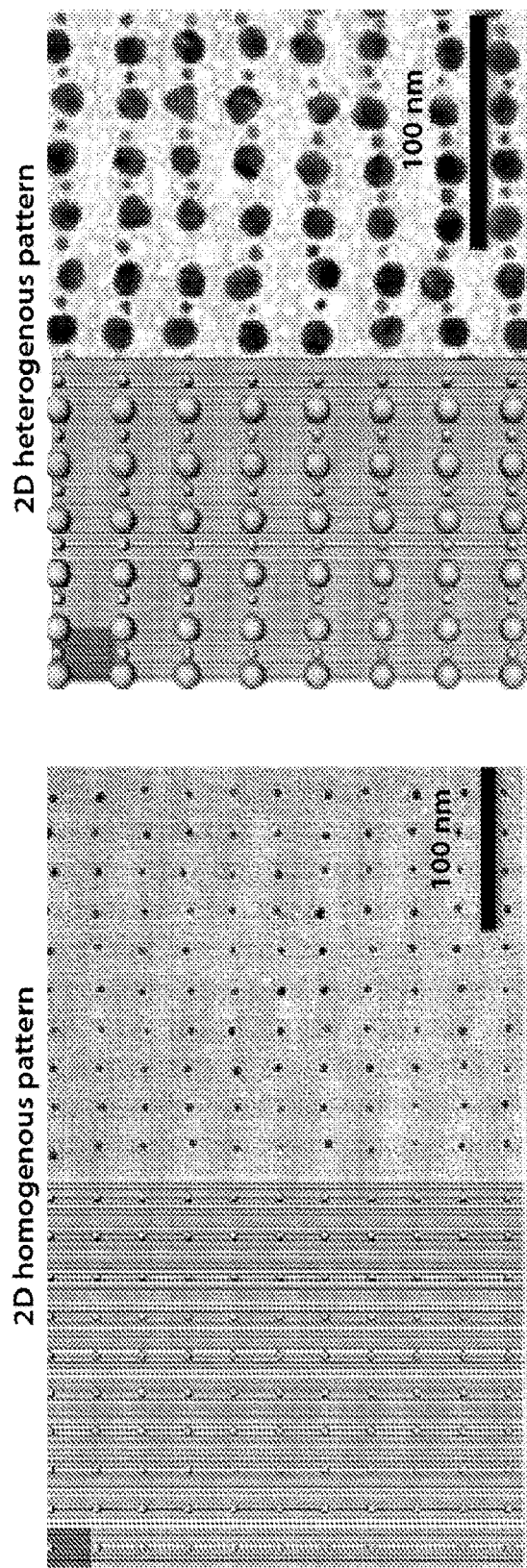
FIG. 2D shows 2D homogeneous (left) and heterogeneous (right) metallic nanoparticles arranged on DNA brick crystals. The 2D homogenous pattern, left panel, shows the pattern designed from 5 nm gold nanoparticles (small light gray spheres). The large dark region shows the repeating unit of the DNA crystal. The light gray region beneath the nanoparticle arrays is the DNA crystal template. The right panel shows the TEM image of the nanoparticles patterned on the template. The small dark spheres represents the 5 nm gold nanoparticles. The light gray region beneath is the DNA crystal template. Scale bar is 100 nm. In the 2D heterogeneous pattern, left panel, shows the pattern designed from 5 nm gold nanoparticles (small light gray spheres) and 13 nm gold nanoparticles (large light gray spheres). The large dark region shows the repeating unit of the DNA crystal. The light gray region beneath the nanoparticle arrays is the DNA crystal template. The right panel shows the TEM image of the nanoparticles patterned on the template. The small dark spheres represent the 5 nm gold nanoparticles. The large dark spheres represent the 13 nm gold nanoparticles. The light gray region beneath is the DNA crystal template. Scale bar is 100 nm.
Figure 2E:
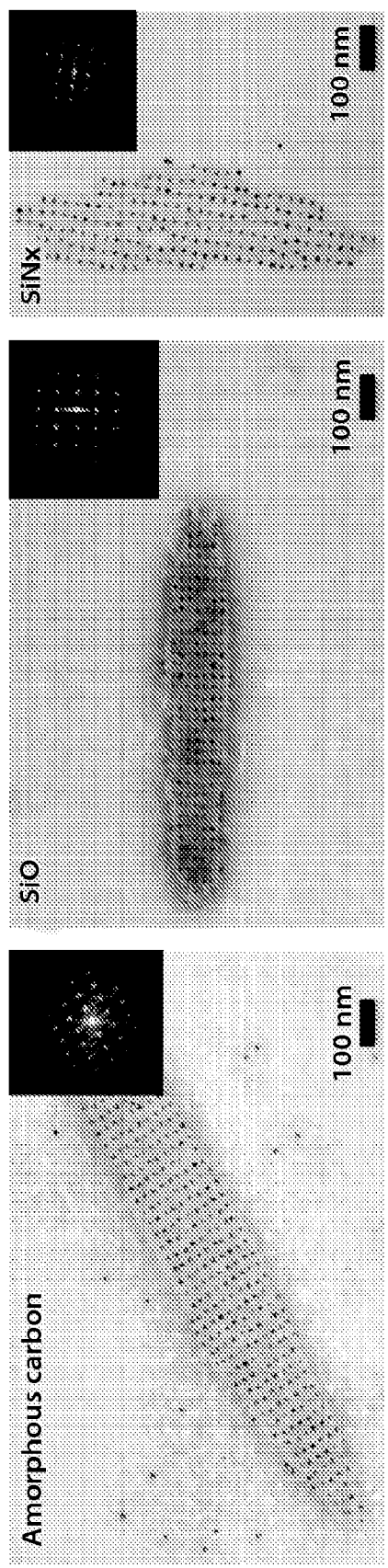
FIG. 2E shows an example of surface-independent patterning using a DNA crystal template. From left to right are TEM images for gold nanoparticles on amorphous carbon, silicon monoxide, and silicon nitride. Within each panel, the dark spheres are 8 nm gold nanoparticles. The gray region beneath the gold nanoparticles is the DNA crystal template. The upper right region of each panel is the Fast Fourier transform for each gold nanoparticle pattern. The scale bar is 100 nm.
Figure 2F:
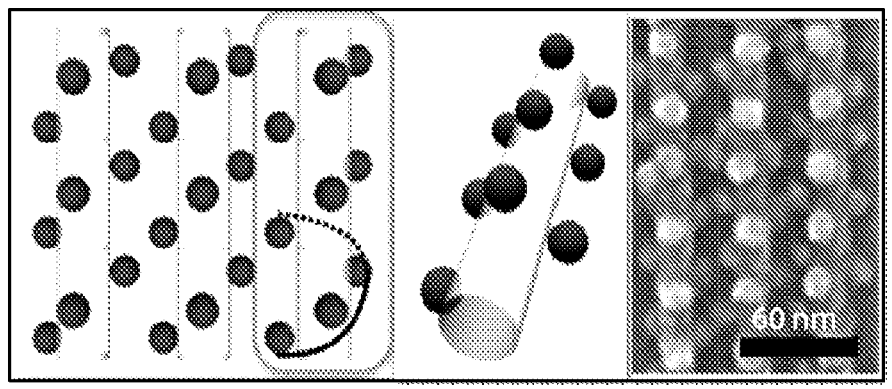
FIG. 2F shows the construction of a chiral nanoparticle surface using DNA template (top) and an example of "printing" a nano-moiety to a silicon wafer (bottom). The top left panel shows the designed chiral nanoparticle surface. Each dark sphere represents a 10 nm gold nanoparticle. The white column represents a DNA ridge on the DNA crystal template. The dark curve line shows the chiral orientation for the nanoparticles on each ridge. The top middle panel shows the chiral nanoparticle chain that composes the 2D chiral surface. Each dark sphere represents a 10 nm gold nanoparticle. The white column represents a DNA ridge on the DNA crystal template. The top right panel shows the SEM image of the assembled chiral nanoparticle surface on a DNA template. Each white sphere is a 10 nm gold nanoparticle on top of the ridge. Each dark sphere is a 10 nm gold nanoparticles attached to the side of the ridge. The dark rectangular column is the DNA ridge on the DNA template. The scale bar is 60 nm. The bottom panel represents an example of "printing" a nano-moiety (e.g., 10-nm gold nanoparticles) to silicon wafer. The gray sphere represents a 10 nm gold nanoparticle that has been "printed" onto the Si surface from a DNA template. The dark surface beneath the nanoparticle is the Si wafer.
Figure 2F:
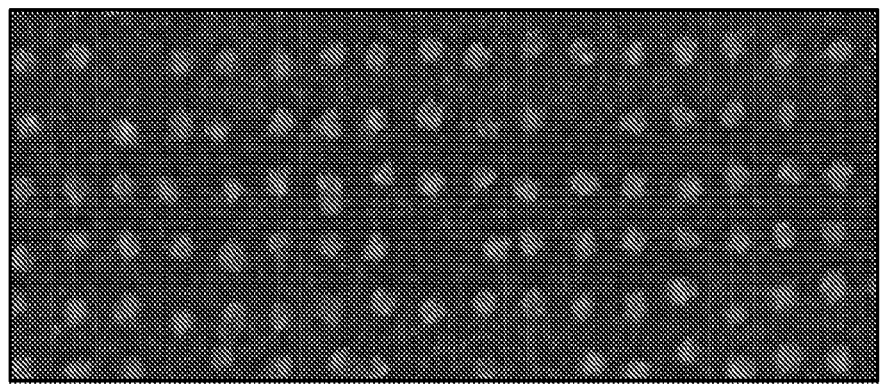

In some embodiments, a DNA nanostructure (i.e., crystal) template is assembled with prescribed 3D binding capability and surface features to moieties, followed by the "printing"

of moieties at specific binding positions on the DNA nanostructure template (FIG. 2F). Complex 2D and/or 3D architectures are thus fabricated by selecting DNA nanostructures having different spatial binding features. Self-assembly of DNA nanostructures ensures the comparable pattern complexity with e-beam lithography but with much higher resolution in three dimensions, for example.

The present disclosure also provides a versatile strategy toward high-resolution fabrication of 3D photonic and electronic architectures that, in some instances, can be easily programmed via computer-aided software.

Also provided herein, in some embodiments, are lithographic methods that use programmable self-assembled bare nucleic acid (e.g., DNA) nanostructures with complex dimensionality as masks for dry etching of substrates into two- and three-dimensional objects. Methods of the present disclosure permit the use of a variety of organic and inorganic substrates that can be shaped into two- and three-dimensional patterns with, for example, 1 nanometer (nm) to 2 nm resolution. Unlike existing nucleic acid lithography techniques, methods of the present disclosure, surprisingly, do not require the use of conformal-growth metal or oxide mask coatings, which decrease lithographic resolution. Further, in some aspects, use of the bare nucleic acid nanostructures as provided herein permit direct "one-step" fabrication of two- and three-dimensional objects.

A non-limiting exemplary method of the present disclosure follows. A solution (e.g., 0.5×Tris-ethylenediaminetetraacetic acid (TE) buffer, 40 mM $Mg^{2+}$; or, 100 mM-1 M $NaNO_3$) comprising a bare three-dimensional DNA nanostructure (e.g., 10 pM-1 μM nanostructure concentration, at least 32 base pairs in length) with a depth of 2 nm is adsorbed onto a substrate (e.g., 1 μl-10 μl or 1-100 μl solution per $cm^2$ substrate), and the solution is permitted to incubate on the substrate (e.g., for 30 minutes to 4 hours) at room temperature with 50-100% humidity in a sealed container. In some embodiments, the solution is permitted to incubate on the substrate for 3 minutes to 4 hours at a temperature of about 4-25° C., optionally with 50-100% humidity for deposition of the DNA nanostructure. Following incubation (or deposition), the solution is removed (or dried) (e.g., spontaneously or by forced air flow or by wiping). The substrate is then washed to remove residual salt from the TE buffer. This process may be regarded as a desalting process intended to remove inorganic salt from the adsorbed DNA nanostructure prior to the final drying step. For hydrophobic substrates, the substrate is incubated in an ethanol/water mixture (e.g., 50-90% ethanol volume) for 1-4 hours.

The diverse surface properties (e.g., hydrophilicity or hydrophobicity) of different substrates, the varying salt concentration in buffer, and the dimensions of DNA nanostructures will dictate whether the desalting process should be carried out in a proper liquid or a combination of several liquids, including DI water, diluted $Mg^{2+}$ solution, anhydrous methanol, anhydrous ethanol, anhydrous isopropyl alcohol and diluted methanol/ethanol/isopropyl alcohol (30-95% volume concentration). The duration of desalting process in a certain liquid can be varied from several seconds (by fast dip-draw) to hours (by quiet incubation or by shaker incubation), in order to balance the trade-off between salt extraction and DNA nanostructure desorption. Finally, the substrate with DNA nanostructure (i.e., following deposition) may be dried by drinking paper wiping, or by forced air flow, or by spontaneous evaporation, according to the nature of the last-step desalting liquid. Additionally or optionally, trace amount of stabilizer agents may be introduced into the deposition step and/or desalting process to further enhance mechanical and/or chemical stability of dried 3D DNA nanostructures. The typical dosage of stabilizer agents will be below 0.1 mM. The stabilizer categories can be metallic cations (including $Na^+$, $K^+$, $Mg^{2+}$, $Ca^{2+}$, $Cr^{3+}$, $Mn^{2+}$, $Fe^{2+}$, $Fe^{3+}$, $Co^{2+}$, $Co^{3+}$, $Ni^{2+}$, $Cu^{2+}$, $Zn^{2+}$, etc.), heavy metal staining agents (including ammonium molybdate, uranyl acetate, uranylformate, uranyl nitrate, phosphotungstic acid, osmium tetroxide, osmium ferricyanide, auroglucothionate, silver nitrate, ruthenium tetroxide and osmium tetroxide) and DNA inter-strand cross-linking agents (including psoralen, mitomycin-C, pyrrolobenzodiazepines, melphalan, cyclophosphamide, etc).

For hydrophilic substrates, the substrate is dipped in flowing water. Etching of the substrate containing the bare DNA nanostructure is performed under standard reactive ion etching conditions (Wu et al. *Journal of Applied Physics*, 10 8: 051101, 2010, incorporated by reference herein). The plasma source can include, for example, halogen, chalogenide, oxygen, fluorocarbon, hydrogen and/or inert gas. The reactive ion etching conditions (e.g., etchant type (e.g., plasma source), chamber pressure, gas flow rate, generator coil power, plate power and etching duration) can be optimized according to substrate composition and expected etching depth. In this example, to etch 40 nm vertically on a flat, polished silicon wafer (see, e.g., FIGS. 2A-C), $CHF_3$ gas (or $CF_4$ or $C_4F_8$ or $SF_6$) in 10 (or about 1 to about 100) standard cubic centimeters per min (SCCM) is used as the etchant source such as the plasma source, and the etching duration is 4 minutes (or about from 5 seconds to about 5 minutes). If more reactive etchant source (e.g., plasma) is used, such as, for example, $SF_6$, the etching duration may be shortened.

Further description of DNA nanostructure deposition on a wafer is provided in Example 3. One of ordinary skill in the art will recognize that such examples are provided as guidance and that other embodiments are therefore also contemplated.

Following deposition of the DNA nanostructures, a coating or film may be applied as described in greater detail in Example 4. One of ordinary skill in the art will recognize that the example is provided as guidance and that other embodiments are therefore also contemplated.

Etching can be carried out after deposition of the DNA nanostructure, with or without further functionalization. Example 5 provides a description of a typical etching process using a DNA nanostructure that carries Au nanoparticles. One of ordinary skill in the art will recognize that the example is provided as guidance and that other embodiments are therefore also contemplated.

Printing can also be carried out using DNA nanostructures, with or without functionalization. Example 6 provides a description of a typical printing process using a DNA nanostructure that carried Au nanoparticles. One of ordinary skill in the art will recognize that the example is provided as guidance and that other embodiments are therefore also contemplated.

Substrates

A substrate refers to a substance (e.g., a solid planar substance or a nucleic acid nanostructure/crystal) onto which another substance is applied. For example, moieties, such as nanoparticles, nanowires or nucleic acids, may be applied to a substrate (e.g., silicon wafer of nucleic acid nanostructure/crystal). Substrates used in accordance with the present disclosure may comprise, without limitation, nucleic acids, silicon, silicon dioxide (also referred to as silica), aluminum oxide, sapphire, germanium, gallium arsenide (GaAs), an alloy of silicon and germanium, or indium phosphide (InP). In some instances, the substrates may comprise silicon nitride, carbon, and/or polymer.

A substrate may be inorganic (e.g., do not contain carbon) or organic (e.g., contain carbon). In some instances, the substrate may comprise graphene and/or graphite.

In some embodiments, a substrate is a hybrid (e.g., comprises a mixture) of any two or more materials (e.g., a hybrid of an inorganic material and an organic material, or a hybrid of two or more different inorganic materials or organic materials), as provided herein. For example, a substrate may comprise a mixture of inorganic and organic materials, a mixture of two or more different inorganic materials, or a mixture of two or more different organic materials. The ratio of one material to another in a hybrid substrate may be, for example, 1:10, 1:20, 1:30, 1:40, 1:50, 1:60, 1:70, 1:80 or 1:90. Other proportions are contemplated herein. Any two or more different materials may be arranged in the substrate as layers, for example. Other configurations are also contemplated herein.

In some embodiments, a substrate comprises a semiconductor material or a mixture of semiconductor materials. Semiconductor materials include, without limitation, Group IV elemental semiconductors, Group IV compound semiconductors, Group VI elemental semiconductors, Group III-V semiconductors, Group II-VI semiconductors, Group I-VII semiconductors, Group IV-VI semiconductors, Group IV-VI semiconductors, Group V-VI semiconductors, Group II-V semiconductors, oxides, layered semiconductors, magnetic semiconductors, organic semiconductors, charge-transfer complexes and combinations thereof.

In some embodiments, a substrate comprises a Group IV semiconductor material. Examples of Group IV semiconductor materials for use in accordance with the present disclosure include, without limitation, diamond, silicon, germanium, gray tin, silicon carbide and combinations thereof.

In some embodiments, a substrate comprises a Group VI semiconductor material. Examples of Group VI semiconductor materials for use in accordance with the present disclosure include, without limitation, sulfur, gray selenium, tellurium and combinations thereof.

In some embodiments, a substrate comprises a Group III-V semiconductor material. Examples of Group III-V semiconductor materials for use in accordance with the present disclosure include, without limitation, boron nitride, cubic, boron nitride, hexagonal, boron phosphide, boron arsenide, boron arsenide, aluminium nitride, aluminium phosphide, aluminium arsenide, aluminium antimonide, gallium nitride, gallium phosphide, gallium arsenide, gallium antimonide, indium nitride, indium phosphide, indium arsenide, indium antimonide and combinations thereof.

In some embodiments, a substrate comprises a Group II-VI semiconductor material. Examples of Group II-VI semiconductor materials for use in accordance with the present disclosure include, without limitation, cadmium selenide, cadmium sulfide, cadmium telluride, zinc oxide, zinc selenide, zinc sulfide, zinc telluride, cuprous chloride, copper sulfide, lead selenide, lead(ii) sulfide, lead telluride, tin sulfide, tin sulfide, tin telluride, lead tin telluride, thallium tin telluride, thallium germanium telluride, bismuth telluride and combinations thereof.

In some embodiments, a substrate comprises a Group I-VII semiconductor material. Examples of Group I-VII semiconductor materials for use in accordance with the present disclosure include, without limitation, cuprous chloride, copper sulfide and a combination of cuprous chloride and copper sulfide.

In some embodiments, a substrate comprises a Group IV-VI semiconductor material. Examples of Group IV-VI semiconductor materials for use in accordance with the present disclosure include, without limitation, lead selenide, lead(ii) sulfide, lead telluride, tin sulfide, tin sulfide, tin telluride, lead tin telluride, thallium tin telluride, thallium germanium telluride and combinations thereof.

In some embodiments, a substrate comprises a Group V-VI semiconductor material. An example of a Group IV-VI semiconductor material for use in accordance with the present disclosure includes, without limitation, bismuth telluride.

In some embodiments, a substrate comprises a Group II-V semiconductor material. Examples of Group II-V semiconductor materials for use in accordance with the present disclosure include, without limitation, cadmium phosphide, cadmium arsenide, cadmium antimonide, zinc phosphide, zinc arsenide, zinc antimonide and combinations thereof.

In some embodiments, a substrate comprises an oxide. Examples of oxides for use in accordance with the present disclosure include, without limitation, titanium dioxide, anatase, titanium dioxide, rutile, titanium dioxide, brookite, copper(i) oxide, copper(ii) oxide, uranium dioxide, uranium trioxide, bismuth trioxide, tin dioxide, barium titanate, strontium titanate, lithium niobate, lanthanum copper oxide and combinations thereof.

In some embodiments, a substrate comprises a layered semiconductor. Examples of layered semiconductors for use in accordance with the present disclosure include, without limitation, lead(ii) iodide, molybdenum disulfide, gallium selenide, tin sulfide, bismuth sulfide and combinations thereof.

In some embodiments, a substrate comprises a magnetic semiconductor. Examples of magnetic semiconductors for use in accordance with the present disclosure include, without limitation, gallium manganese arsenide, indium manganese arsenide, cadmium manganese telluride, lead manganese telluride, lanthanum calcium manganate, iron(ii) oxide, nickel(ii) oxide, europium(ii) oxide, europium(ii) sulfide, chromium(iii) bromide and combinations thereof.

Other examples of semiconductor materials that may be used in accordance with the present disclosure include, without limitation, copper indium selenide, cis, silver gallium sulfide, zinc silicon phosphide, arsenic sulfide, platinum silicide, bismuth(iii) iodide, mercury(ii) iodide, thallium(i) bromide, silver sulfide, iron disulfide, copper zinc tin sulfide, copper zinc antimony sulfide and combinations thereof.

In some embodiments, a substrate comprises a chalcogenide. A chalcogenide is a chemical compound that includes at least one chalcogen anion and at least one more electropositive element. In some embodiments, the chalcogenide is a sulfide, selenide or a telluride.

In some embodiments, a substrate comprises an electrical insulator. An electric insulator is a material with internal electric charges that do not flow freely, and therefore make it difficult to conduct an electric current under the influence of an electric field.

In some embodiments, a substrate comprises a metal. Examples of metals that may be used in accordance with the present disclosure include, without limitation, aluminium, chromium, titanium, tungsten, tantalum, niobium, platinum, zinc and combinations thereof.

In some embodiments, a substrate comprises carbon, SiC, $LiNbO_3$, $PbZrTiO_3$, $HfO_2$, $TiO_2$, $V_2O_5$, $Al_2O_3$, $Ta_2O_3$ or combinations thereof.

In some embodiments, a substrate comprises a polymer. Examples of polymers that may be used in accordance with the present disclosure include, without limitation, polydimethylsiloxane (PDMS), poly(methyl methacrylate) (PMMA) (e.g., PMMA resin), and self-assembling polymers. In some embodiments, the substrate comprises poly(methyl methacrylatemethacrylic acid) (e.g., copolymer P(MMA-MAA)). In some embodiments, the substrate comprises self-assembling block-copolymers.

In some embodiments, a substrate comprises a film such as, for example, a photoresist film, a chemical vapor deposition (CVD) film, a semiconductor film, graphene and/or other single-layer atomic films. In some embodiments, the substrate comprises a physical vapor deposition (PVD) film, an atomic layer deposition (ALD) film and/or an ion implantation film.

In some embodiments, a substrate is a polished silicon wafer such as, for example, a plasma treated, or a hot piranha solution treated, silicon wafer (e.g., 7:3 concentrated $H_2SO_4$: 35% $H_2O_2$).

In some embodiments, a moiety is coupled to a surface of a substrate. In some embodiments, a substrate is a substantially planar substance having a top surface onto which moieties are coupled. Substrates may be single-layered or multi-layered (e.g., multi-layered grapheme/BN/$MoS_2$, such as ribbon or mesh).

In some embodiments, a substrate has a (e.g., at least one) layer comprising or consisting of biomolecules. Biomolecules include proteins and nucleic acids, for example. Other biomolecules are contemplated herein, such as polysaccharides and lipids. A substrate, in some embodiments, may contain only proteins (a homogeneous or heterogeneous population), only nucleic acids (a homogeneous or heterogeneous population), or a mixture of proteins and nucleic acids (or other biomolecules). A biomolecular layer of a substrate may be an internal layer (e.g., sandwiched between two layers) and/or an external layer (e.g., surface exposed to the surrounding environment).

Nucleic Acid Nanostructures, also Referred to as "Crystals"

Aspects of the present disclosure relate to two-dimensional or three-dimensional nucleic acid nanostructures for patterning of substrates. A "nucleic acid nanostructure" is a rationally-designed, artificial (e.g., non-naturally occurring) structure self-assembled from individual nucleic acids. In some embodiments, a self-assembled one-, two- or three-dimensional nucleic acid structure, referred to herein as a "crystal," may be a substrate. It should be understood that the terms "nucleic acid nanostructure" and "nucleic acid crystal" (or simply "crystal") may be used herein interchangeably.

A "bare nucleic acid nanostructure" is a nucleic acid nanostructure without a surface coating. Prior to the present disclosure, nucleic acid nanostructures (e.g., DNA nanostructures) were coated with, for example, a metal coating (see, e.g., Jin Z. et al. *Nature Communications,* 4: 1663, 2013, incorporated by reference herein) or an oxide coating (see, e.g., Surwade S. P. et al. *J. Am. Chem. Soc.* 133: 11868, 2011, incorporated by reference herein) so that the nucleic acid nanostructures could withstand etching conditions. However, metal or oxide coatings, for example, decrease lithographic resolution, and use of such coatings imposes resolution limits on the substrate being etched. The nucleic acid nanostructures (e.g., DNA nanostructures) of the present disclosure, surprisingly, do not require such surface coatings. Multilayered nucleic acid nanostructures (e.g., three-dimensional DNA nanostructures), for example, are robust and able to withstand etching (e.g., plasma etching). Thus, in some embodiments, a bare nucleic acid nanostructure is a nucleic acid nanostructure, such as, for example, a multi-layered nucleic acid nanostructure, without a metal coating and without an oxide coating.

It should be understood, however, that while bare nucleic acid nanostructures of the present disclosure do not contain coatings, they may, in some embodiments, be pre-treated (e.g., denatured or modified) prior to etching. For example, a bare nucleic acid nanostructure may be subjected to pretreatment with ultraviolet crosslinking (Ravanat, J. L. et al. *Journal of Photochemistry and Photobiology B: Biology* 63: 88-102, 2001, incorporated by reference herein) or ozonolysis (Cataldo, F. *International Journal of Biological Macromolecules* 38: 248-254, 2006, incorporated by reference herein), dye/ion staining, carbonization (Rajesh, B. et al. *J. Phys. Chem. B* 107(12): 2701-2708, 2003, incorporated by reference herein), metal cation doping (Petty, J. T. et al *J. Am. Chem. Soc.* 126: 5207-5212, 2004, incorporated by reference herein) or capillary wetting (Piner, R. D. *Science* 283: 661, 1999, incorporated by reference herein).

A bare nucleic acid nanostructure of the present disclosure may be used as a mask to cover a region of a substrate intended for patterning (e.g., protect the region from etching). Thus, in some embodiments, a bare nucleic acid nanostructure is referred to as a "bare nucleic acid nanostructure mask."

Nucleic acid nanostructures (i.e., crystals) are typically nanometer-scale or micrometer-scale structures (e.g., having a length scale of 1 to 1000 nanometers (nm), or 1 to 10 micrometers (μm)). In some instances, a micrometer-scale structures is assembled from more than one nanometer-scale or micrometer-scale structure. In some embodiments, a nucleic acid nanostructure (and, thus, a crystal) has a length scale of 1 to 1000 nm, 1 to 900 nm, 1 to 800 nm, 1 to 700 nm, 1 to 600 nm, 1 to 500 nm, 1 to 400 nm, 1 to 300 nm, 1 to 200 nm, 1 to 100 nm or 1 to 50 nm. In some embodiments, a nucleic acid nanostructure has a length scale of 1, 2, 3, 4, 5, 6, 7, 8, 9 or 10 μm. In some embodiments, a nucleic acid nanostructure has a length scale of greater than 1000 nm. In some embodiments, a nucleic acid nanostructure has a length scale of 1 μm to 2 μm. In some embodiments, a nucleic acid nanostructure has a length scale of 200 nm to 2 μm, or more.

In some embodiments, a nucleic acid nanostructure (i.e., crystal) assembles from a plurality of different nucleic acids (e.g., single-stranded nucleic acids). For example, a nucleic acid nanostructure may assemble from at least 10, at least 20, at least 30, at least 40, at least 50, at least 60, at least 70, at least 80, at least 90 or at least 100 nucleic acids. In some embodiments, a nucleic acid nanostructure assembles from at least 100, at least 200, at least 300, at least 400, at least 500, or more, nucleic acids. The term "nucleic acid" encompasses "oligonucleotides," which are short, single-stranded nucleic acids (e.g., DNA) having a length of 10 nucleotides to 100 nucleotides. In some embodiments, an oligonucleotide has a length of 10 to 20 nucleotides, 10 to 30 nucleotides, 10 to 40 nucleotides, 10 to 50 nucleotides, 10 to 60 nucleotides, 10 to 70 nucleotides, 10 to 80 nucleotides or 10 to 90 nucleotides. In some embodiments, an oligonucleotide has a length of 20 to 50, 20 to 75 or 20 to 100 nucleotides. In some embodiments, an oligonucleotide has a length of 30, 31, 32, 33, 34, 35, 36, 37, 38, 39, 40, 41, 42, 43, 44, 45, 46, 47, 48, 49 or 50 nucleotides.

In some embodiments, a nucleic acid nanostructure (i.e., crystal) is assembled from single-stranded nucleic acids, double-stranded nucleic acids, or a combination of single-stranded and double-stranded nucleic acids.

Nucleic acid nanostructures (i.e., crystals) may assemble, in some embodiments, from a plurality of heterogeneous nucleic acids (e.g., oligonucleotides). "Heterogeneous" nucleic acids may differ from each other with respect to nucleotide sequence. For example, in a heterogeneous plurality that includes nucleic acids A, B and C, the nucleotide sequence of nucleic acid A differs from the nucleotide sequence of nucleic acid B, which differs from the nucleotide sequence of nucleic acid C. Heterogeneous nucleic acids may also differ with respect to length and chemical compositions (e.g., isolated v. synthetic).

The fundamental principle for designing self-assembled nucleic acid nanostructures (i.e., crystals) is that sequence complementarity in nucleic acid strands is encoded such that, by pairing up complementary segments, the nucleic acid strands self-organize into a predefined nanostructure under appropriate physical conditions. From this basic principle (see, e.g., Seeman N. C. *J. Theor. Biol.* 99: 237, 1982, incorporated by reference herein), researchers have created diverse synthetic nucleic acid nanostructures (see, e.g., Seeman N. C. *Nature* 421: 427, 2003; Shih W. M. et al. *Curr. Opin. Struct. Biol.* 20: 276, 2010, each of which is incorporated by reference herein). Examples of nucleic acid (e.g., DNA) nanostructures, and methods of producing such structures, that may be used in accordance with the present disclosure are known and include, without limitation, lattices (see, e.g., Winfree E. et al. *Nature* 394: 539, 1998; Yan H. et al. *Science* 301: 1882, 2003; Yan H. et al. *Proc. Natl. Acad. of Sci. USA* 100; 8103, 2003; Liu D. et al. *J. Am. Chem. Soc.* 126: 2324, 2004; Rothemund P. W. K. et al. *PLoS Biology* 2: 2041, 2004, each of which is incorporated by reference herein), ribbons (see, e.g., Park S. H. et al. *Nano Lett.* 5: 729, 2005; Yin P. et al. *Science* 321: 824, 2008, each of which is incorporated by reference herein), tubes (see, e.g., Yan H. *Science,* 2003; P. Yin, 2008, each of which is incorporated by reference herein), finite two-dimensional and three dimensional objects with defined shapes (see, e.g., Chen J. et al. *Nature* 350: 631, 1991; Rothemund P. W. K., *Nature,* 2006; He Y. et al. *Nature* 452: 198, 2008; Ke Y. et al. *Nano. Lett.* 9: 2445, 2009; Douglas S. M. et al. *Nature* 459: 414, 2009; Dietz H. et al. *Science* 325: 725, 2009; Andersen E. S. et al. *Nature* 459: 73, 2009; Liedl T. et al. *Nature Nanotech.* 5: 520, 2010; Han D. et al. *Science* 332: 342, 2011, each of which is incorporated by reference herein), and macroscopic crystals (see, e.g., Meng J. P. et al. *Nature* 461: 74, 2009, incorporated by reference herein).

Figure 4A:
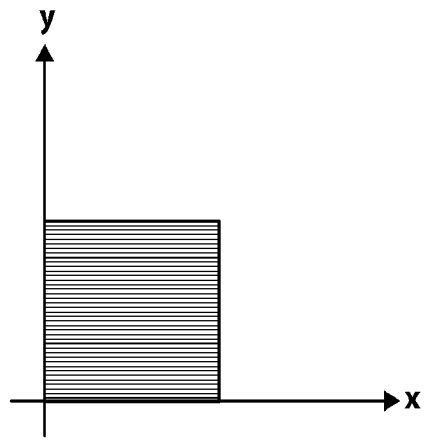
FIG. 4A shows a schematic of an example of a two-dimensional nucleic acid nanostructure having a first dimension along the x-axis and a second dimension along the y-axis.

Nucleic acid nanostructures (i.e., crystals) of the present disclosure may be two-dimensional or three-dimensional. Two-dimensional nucleic acid nanostructures are single-layer planar structures that can be measured along an x-axis and a y-axis (FIG. 4A). A "layer" of a nucleic acid nanostructure refers to a planar arrangement of nucleic acids that is uniform in height. "Height" refers to a measurement of the vertical distance (e.g., along the y-axis) of a structure. "Maximum height" refers to a measurement of the greatest vertical distance of a structure (e.g., distance between the highest point of the structure and the lowest point of the structure). Generally, a nucleic acid layer has a maximum height less than 3 nm (e.g., 1 nm, 1.5 nm, 2 nm, 2.5 nm). A two-dimensional nucleic acid nanostructure is a single-layer structure, thus, a two-dimensional nucleic acid nanostructure has a planar arrangement of nucleic acids that is uniform in height and has a maximum height less than 3 nm. In some embodiments, a two-dimensional nucleic acid nanostructure has a maximum height of less than 2.5 nm. In some embodiments, a two-dimensional nucleic acid nanostructure has a maximum height of 1 nm to 2.9 nm, or 1 nm to 2.5 nm. In some embodiments, a two-dimensional nucleic acid nanostructure has a maximum height of 1 nm, 1.5 nm, 2 nm or 2.5 nm. Non-limiting examples of two-dimensional nucleic acid nanostructures include nucleic acid lattices, tiles and nanoribbons (see, e.g., Rothemund P. W. K., *Nature* 440: 297, 2006; and Jungmann R. et al., *Nanotechnology* 22(27): 275301, 2011, each of which is incorporated by reference herein).

Figure 4B:
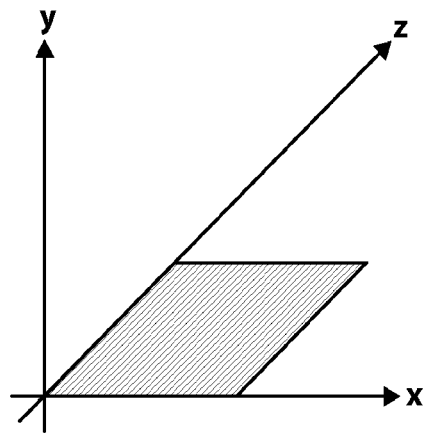
FIG. 4B shows a schematic of an example of a two-dimensional nucleic acid nanostructure having a first dimension along the x-axis and a second dimension along the z-axis.
Figure 4C:
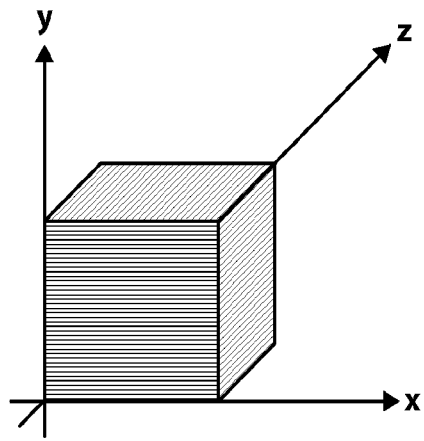
FIG. 4C shows a schematic of an example of a three-dimensional nucleic acid nanostructure having a first dimension along the x-axis, a second dimension along the y-axis, and a third dimension along the z-axis.
Figure 5:
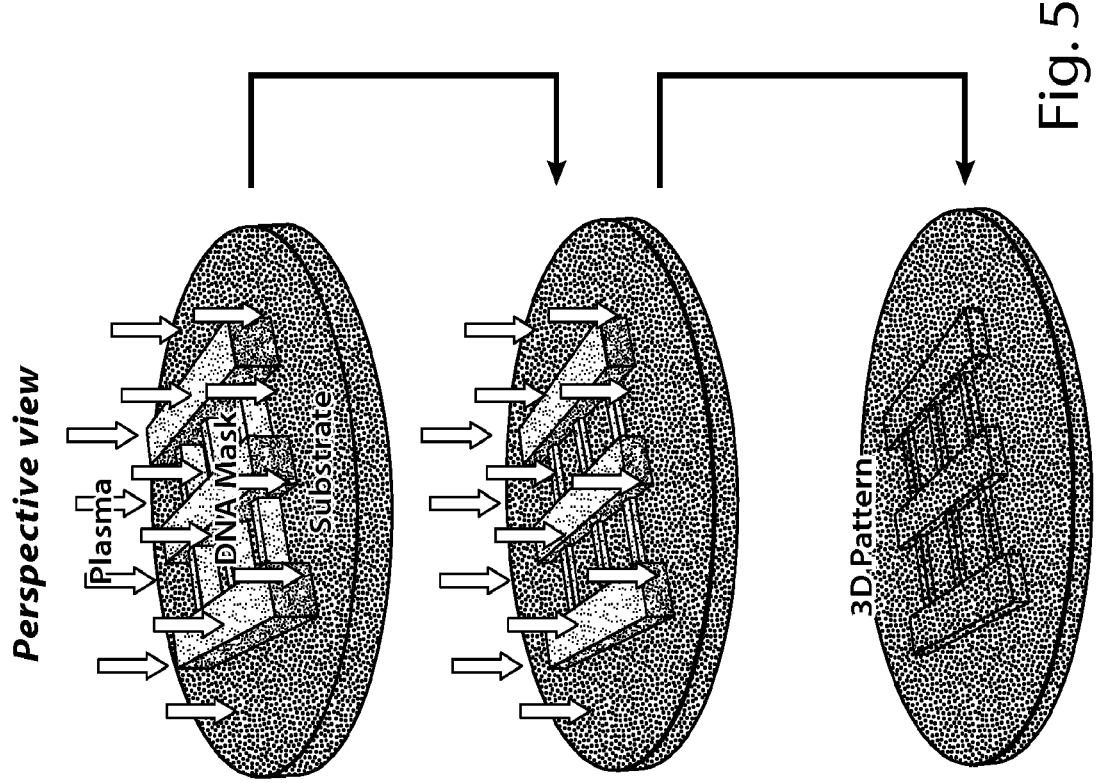
FIG. 5 shows a side view schematic (left) and a perspective view schematic (right) of one embodiment of a DNA lithography method of the present disclosure. Bare DNA nanostructure is adsorbed onto a substrate, and then the substrate onto which the bare DNA nanostructure is adsorbed is etched under reactive ion etching conditions, thereby producing a patterned substrate.
Figure 5:
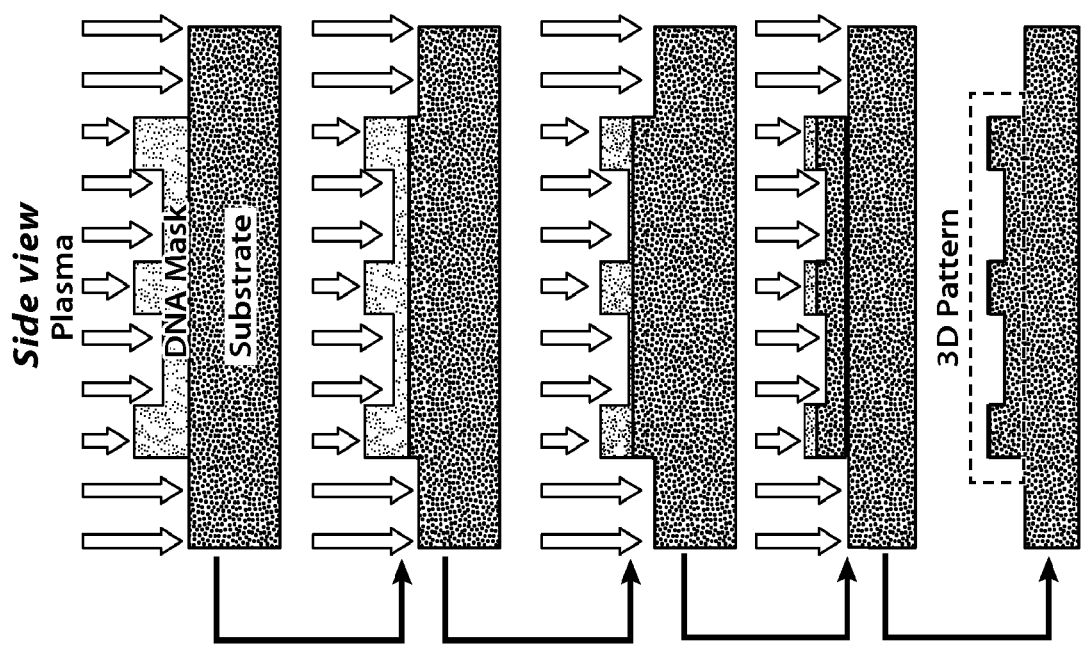
Figure 7A:
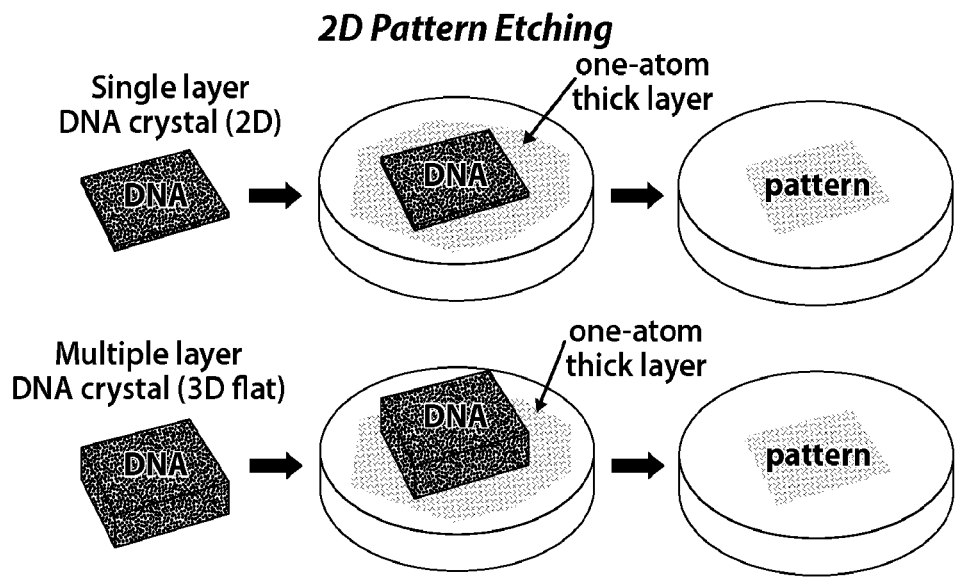
FIG. 7A shows a schematic comparing lithographic patterning of two-dimensional films using a two-dimensional DNA nanostructure (top) or a three-dimensional DNA nanostructure (bottom).
Figure 7B:
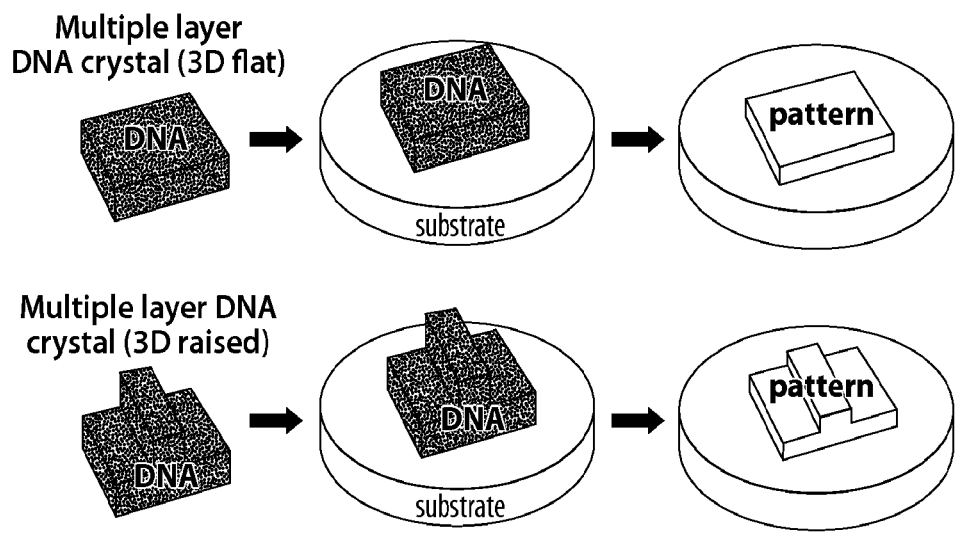
FIG. 7B shows a schematic of one embodiment of a DNA lithography method of the present disclosure in which a three-dimensional DNA nanostructure mask is used to pattern a substrate into a three-dimensional object. A three-dimensional DNA nanostructure mask can be used to pattern a two-dimensional substrate or a three-dimensional substrate, whereas a two-dimensional DNA nanostructure mask can be used to pattern only a two-dimensional substrate.

Three-dimensional nucleic acid nanostructures (i.e., crystals) can be measured along an x-axis, a y-axis and a z-axis (FIG. 4B). A three-dimensional nucleic acid nanostructure has a maximum height equal to or greater than 3 nm. In some embodiments, a three-dimensional nucleic acid nanostructure has a maximum height of greater than 4 nm, greater than 5 nm, greater than 6 nm, greater than 7 nm, greater than 8 nm, greater than 9 nm or greater than 10 nm. In some embodiments, a three-dimensional nucleic acid nanostructure has a maximum height of 3 nm to 50 nm, 3 nm to 100 nm, 3 nm to 250 nm or 3 nm to 500 nm. In some embodiments, a three-dimensional nanostructure may be a multi-layer structure. In some embodiments, a three-dimensional nucleic acid nanostructure comprises 2 to 200, or more, nucleic acid layers. In some embodiments, a three-dimensional nucleic acid nanostructure includes greater than 2, greater than 3, greater than 4, or greater than 5 nucleic acid layers. In some embodiments, a three-dimensional nucleic acid nanostructure comprises 2, 3, 4, 5, 6, 7, 8, 9, 10, 15, 20, 30, 35, 40, 45 or 50 or more nucleic acid layers. A three-dimensional nanostructure may be uniform in height or it may be non-uniform in height. For example, the schematic DNA nanostructure in FIG. 7B, top, represents a three-dimensional nanostructure that is uniform in height (e.g., a planar/flat structure), and the schematic DNA nanostructure in FIG. 7B, bottom, represents a three-dimensional nanostructure that is non-uniform in height—the center area is higher than the adjacent areas of the structure. The vertical distance of the center area of the nanostructure in FIG. 7B, bottom, represents the maximum height of the nanostructure. Non-limiting examples of three-dimensional nucleic acid nanostructures include nucleic acid cubes and other abstract and/or irregular three-dimensional shapes (see, e.g., Douglas S. M, et al. *Nature* 459: 414, 2009; Andersen E. D. et al. *Nature* 459: 73, 2009; Han D. et al. *Science* 332: 342, 2011; Ke Y. et al., 2011; Wei B., 2012, each of which is incorporated by reference herein).

Conceptually, a single-layer two-dimensional nucleic acid nanostructure (i.e., crystal), in some embodiments, can be constructed by "extraction" of a layer from a three-dimensional nucleic acid nanostructure (see, e.g., Ke Y. et al., 2012; see also Wei B., et al. *Nature* 485: 623, 2012, each of which is incorporated by reference herein). A three-dimensional nucleic acid nanostructure, in some embodiments, may be assembled from more than one two-dimensional nucleic acid nanostructure (e.g., more than one layer of nucleic acids) or more than one three-dimensional nucleic acid nanostructure (e.g., more than one "pre-assembled" nucleic acid nanostructure that is linked to one or more other "pre-assembled" nucleic acid nanostructure).

Thus, contemplated herein are composite nucleic acid nanostructures (i.e., crystals). In some embodiments, a composite nucleic acid nanostructure comprises nucleic acid nanostructures linked to each other using linkers. The linkers are typically not integral to the nucleic acid nanostructures, although they may be attached to the nanostructures through suitable functional groups. The ability to attach two or more nucleic acid nanostructures together allows structures of greater size (e.g., micrometer size) and complexity to be made. The dimensions of these composite structures may range, for example, from 500 nm to 100 µm, 1 µm to 1000 µm, 1 µm to 5 µm, 1 µm to 10 µm, 1 µm to 20 µm, or more. Thus, in some embodiments, composite nanostructures encompass microstructures. Examples of linkers for use in accordance with the present disclosure include, without limitation, chemical crosslinkers (e.g., glutaraldehyde), biomolecules (e.g., avidin-biotin), and ligand-functionalized nanoparticles/moieties (e.g., single-stranded-nucleic acid-functionalized nanoparticles). In some instances, the linkers may involve click chemistry or coordinating interaction (Ni2+/polyhistidine).

In some embodiments, a nucleic acid nanostructure (i.e., crystal) (e.g., a bare nucleic acid nanostructure mask) is assembled using a nucleic acid (e.g., DNA) origami approach. With a DNA origami approach, for example, a long "scaffold" nucleic acid strand is folded to a predesigned shape through interactions with relatively shorter "staple" strands. Thus, in some embodiments, a single-stranded nucleic acid for assembly of a nucleic acid nanostructure has a length of at least 500 base pairs, at least 1 kilobase, at least 2 kilobases, at least 3 kilobases, at least 4 kilobases, at least 5 kilobases, at least 6 kilobases, at least 7 kilobases, at least 8 kilobases, at least 9 kilobases, or at least 10 kilobases. In some embodiments, a single-stranded nucleic acid for assembly of a nucleic acid nanostructure has a length of 500 base pairs to 10 kilobases, or more. In some embodiments, a single-stranded nucleic acid for assembly of a nucleic acid nanostructure has a length of 7 to 8 kilobases. In some embodiments, a single-stranded nucleic acid for assembly of a nucleic acid nanostructure comprises the M13 viral genome.

In some embodiments, a nucleic acid nanostructure (i.e., crystal) (e.g., a bare nucleic acid nanostructure mask) is assembled from single-stranded tiles (SSTs) (see, e.g., Wei B. et al. *Nature* 485: 626, 2012, incorporated by reference herein) or nucleic acid "bricks" (see, e.g., Ke Y. et al. *Science* 388:1177, 2012; International Publication Number WO 2014/018675 A1, published Jan. 30, 2014, each of which is incorporated by reference herein). For example, single-stranded 2- or 4-domain oligonucleotides self-assemble, through sequence-specific annealing, into two- and/or three-dimensional nanostructures in a predetermined (e.g., predicted) manner. As a result, the position of each oligonucleotide in the nanostructure is known. In this way, a nucleic acid nanostructure may be modified, for example, by adding, removing or replacing oligonucleotides at particular positions. The nanostructure may also be modified, for example, by attachment of moieties, at particular positions. This may be accomplished by using a modified oligonucleotide as a starting material or by modifying a particular oligonucleotide after the nanostructure is formed. Therefore, knowing the position of each of the starting oligonucleotides in the resultant nanostructure provides addressability to the nanostructure.

"Self-assembly" refers to the ability of nucleic acids (and, in some instances, pre-formed nucleic acid nanostructures (i.e., crystals)) to anneal to each other, in a sequence-specific manner, in a predicted manner and without external control. In some embodiments, nucleic acid nanostructure self-assembly methods include combining nucleic acids (e.g., single-stranded nucleic acids, or oligonucleotides) in a single vessel and allowing the nucleic acids to anneal to each other, based on sequence complementarity. In some embodiments, this annealing process involves placing the nucleic acids at an elevated temperature and then reducing the temperature gradually in order to favor sequence-specific binding. Various nucleic acid nanostructures or self-assembly methods are known and described herein.

Nucleic acids of the present disclosure include DNA such as D-form DNA and L-form DNA and RNA, as well as various modifications thereof. Nucleic acid modifications include base modifications, sugar modifications, and backbone modifications. Non-limiting examples of such modifications are provided below.

Examples of modified DNA nucleic acids (e.g., DNA variants) that may be used in accordance with the present disclosure include, without limitation, L-DNA (the backbone enantiomer of DNA, known in the literature), peptide nucleic acids (PNA) bisPNA clamp, a pseudocomplementary PNA, locked nucleic acid (LNA), and co-nucleic acids of the above such as DNA-LNA co-nucleic acids. Thus, the present disclosure contemplates nanostructures that comprise DNA, RNA, LNA, PNA or combinations thereof. It is to be understood that the nucleic acids used in methods and compositions of the present disclosure may be homogeneous or heterogeneous in nature. As an example, nucleic acids may be completely DNA in nature or they may be comprised of DNA and non-DNA (e.g., LNA) monomers or sequences. Thus, any combination of nucleic acid elements may be used. The nucleic acid modification may render the nucleic acid more stable and/or less susceptible to degradation under certain conditions. For example, in some embodiments, nucleic acids are nuclease-resistant.

Nucleic acids of the present disclosure, in some embodiments, have a homogenous backbone (e.g., entirely phosphodiester or entirely phosphorothioate) or a heterogeneous (or chimeric) backbone. Phosphorothioate backbone modifications may render an oligonucleotide less susceptible to nucleases and thus more stable (as compared to a native phosphodiester backbone nucleic acid) under certain conditions. Other linkages that may provide more stability to a nucleic acid of the present disclosure include, without limitation, phosphorodithioate linkages, methylphosphonate linkages, methylphosphorothioate linkages, boranophosphonate linkages, peptide linkages, alkyl linkages and dephospho-type linkages. Thus, in some embodiments, nucleic acids have non-naturally occurring backbones.

In some embodiments, nucleic acids of the present disclosure do not encode a product (e.g., a protein).

Nucleic acids of the present disclosure, in some embodiments, additionally or alternatively comprise modifications in their sugars. For example, a (β-ribose unit or a (β-D-2'-deoxyribose unit can be replaced by a modified sugar unit, wherein the modified sugar unit is, for example, selected from β-D-ribose, α-D-2'-deoxyribose, L-2'-deoxyribose, 2'-F-2'-deoxyribose, arabinose, 2'-F-arabinose, 2'-O—($C_1$-$C_6$)alkyl-ribose, preferably 2'-O—($C_1$-$C_6$)alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'-$NH_2$-2'-deoxyribose, β-D-xylo-furanose, α-arabinofuranose, 2,4-dideoxy-(β-D-erythro-hexo-pyranose, and carbocyclic (see, e.g., Froehler J. *Am. Chem. Soc.* 114:8320, 1992, incorporated by reference herein) and/or open-chain sugar analogs (see, e.g., Vandendriessche et al. *Tetrahedron* 49:7223, 1993, incorporated by reference herein) and/or bicyclosugar analogs (see, e.g., Tarkov M. et al. *Helv. Chim. Acta.* 76:481, 1993, incorporated by reference herein).

Nucleic acids of the present disclosure, in some embodiments, comprise modifications in their bases. Modified bases include, without limitation, modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7-deazaguanine, 7-deaza-7-substituted guanine (such as 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

Nucleic acids of the present disclosure, in some embodiments, are synthesized in vitro. Thus, in some embodiments, nucleic acids are synthetic (e.g., not naturally-occurring). Methods for synthesizing nucleic acids, including automated nucleic acid synthesis, are known. For example, nucleic acids having modified backbones, such as backbones comprising phosphorothioate linkages, and including those comprising chimeric modified backbones, may be synthesized using automated techniques employing either phosphoramidate or H-phosphonate chemistries (see, e.g., F. E. Eckstein, "Oligonucleotides and Analogues—A Practical Approach" IRL Press, Oxford, UK, 1991; and Matteucci M. D. et al. *Tetrahedron Lett.* 21: 719, 1980). Synthesis of nucleic acids with aryl- and alkyl-phosphonate linkages are also contemplated (see, e.g., U.S. Pat. No. 4,469,863). In some embodiments, nucleic acids with alkylphosphotriester linkages (in which the charged oxygen moiety is alkylated, e.g., as described in U.S. Pat. No. 5,023,243 and European Patent No. 092,574) are prepared by automated solid phase synthesis using commercially available reagents. Methods for making other DNA backbone modifications and substitutions have been described (see, e.g., Uhlmann E. et al. *Chem. Rev.* 90:544, 1990; Goodchild J. *Bioconjugate Chem.* 1:165, 1990; Crooke S. T. et al. *Annu. Rev. Pharmacol. Toxicol.* 36:107, 1996; and Hunziker J. et al. *Mod Synth Methods* 7:331, 1995, each of which is incorporated by reference) and may be used in accordance with the present disclosure.

Some aspects of the present disclosure are directed to assembling nucleic acid nanostructures using annealing processes. In some embodiments, nucleic acids are combined, in a single vessel such as, but not limited to, a tube, a well or a vial. The molar amounts of nucleic acids that are used may depend on the frequency of each nucleic acid in the nanostructure desired and the amount of nanostructure desired. In some embodiments, the nucleic acids may be present in equimolar concentrations. In some embodiments, each nucleic acid (e.g., oligonucleotide) may be present at a concentration of about 200 nM. In some embodiments, the nucleic acids are placed in a solution. The solution may be buffered, although the annealing reaction can also occur in the absence of buffer. The solution may further comprise divalent cations such as, but not limited, to $Mg^{2+}$. The cation or salt concentration may vary. An exemplary concentration is about 490 mM. The solution may also comprise EDTA or other nuclease inhibitors in order to prevent degradation of the nucleic acids.

An annealing reaction is carried out, in some embodiments, by heating the solution containing nucleic acids and then allowing the solution to slowly cool down (e.g., heated and then placed in a room temperature environment). The temperature of the reaction should be sufficiently high to melt any undesirable secondary structure such as hairpin structures and to ensure that the nucleic acids are not bound incorrectly to other non-complementary nucleic acids. The temperature, therefore, may be initially raised to any temperature below or equal to 100° C. For example, the temperature may be initially raised to 100° C., 95° C., 90° C., 85° C., 80° C., 75° C., 70° C., 65° C. or 60° C. The temperature may be raised by placing the vessel in a hot water bath, heating block or a device capable of temperature control, such as a thermal cycler (e.g., polymerase chain reaction (PCR) machine). The vessel may be kept in that environment for seconds or minutes. In some embodiments, an incubation time of about 1-10 minutes is sufficient.

Once nucleic acid incubation at an elevated temperature is complete, the temperature may be dropped in a number of ways. The temperature may be dropped, for example, in an automated manner using a computer algorithm that drops the temperature by a certain amount and maintains that temperature for a certain period of time before dropping the temperature again. Such automated methods may involve dropping the temperature by a degree in each step or by a number of degrees at each step. The vessel may thus be heated and cooled in the same device. As another example, the heated solution may be placed at room temperature to cool. An exemplary process for dropping temperature is as follows. To effect a drop in temperature from about 80° C. to about 24° C., the temperature is changed from 80° C. to 61° C. in one degree increments at a rate of 3 minutes per degree (e.g., 80° C. for 3 minutes, 79° C. for 3 minutes, etc.). The temperature is then changed from 60° C. to 24° C. in one degree increments and at a rate of about 120 minutes per degree (e.g., 60° C. for 120 minutes, 59° C. for 210 minutes, etc.). The total annealing time for this process is about 17 hours. In accordance with the present disclosure, under these conditions, nucleic acids (e.g., oligonucleotides) self-assemble into a nanostructure (i.e., crystal) of predetermined and desired shape and size.

An example of a specific annealing process uses one hundred different 200 nM oligonucleotides in solution (e.g., 5 mM Tris-1 mM EDTA (TE), 40 mM $MgCl_2$) and the solution is heated to about 90° C. and then cooled to about 24° C. over a period of about 73 hours, as described above with a 3 minute per degree drop between 80° C. and 61° C., and a 120 minute per degree drop between 60° C. and 24° C. It should be understood that the foregoing annealing process is exemplary and that other annealing processes may be used in accordance with the present disclosure.

The disclosure provides nucleic acid nanostructures generated using epitaxial growth processes. Epitaxial-grown nucleic acid nanostructures (to be used as DNA templates, for example) may be formed through a seed-mediated nucleic acid (e.g., DNA) growth process starting from a pre-formed nucleic acid (e.g., DNA) seed. The seed may comprise one or more single-stranded DNAs with longer binding domains (such as 16 nucleotides compared with a typical 8 nucleotides per domain) or it may be a pre-formed DNA structure, without limitation. Epitaxial growth creates a single-crystalline interface between the seed and the resulting grown structure. In contrast to existing seed-mediated DNA growth, epitaxial growth does not require sequence design for specific growth pathway, and can be used for 3D structures. Additionally, using epitaxial growth, the seed-mediated DNA formation can start either along π-π stacking direction (helical direction) or perpendicular to the helical direction.

Figure 14:
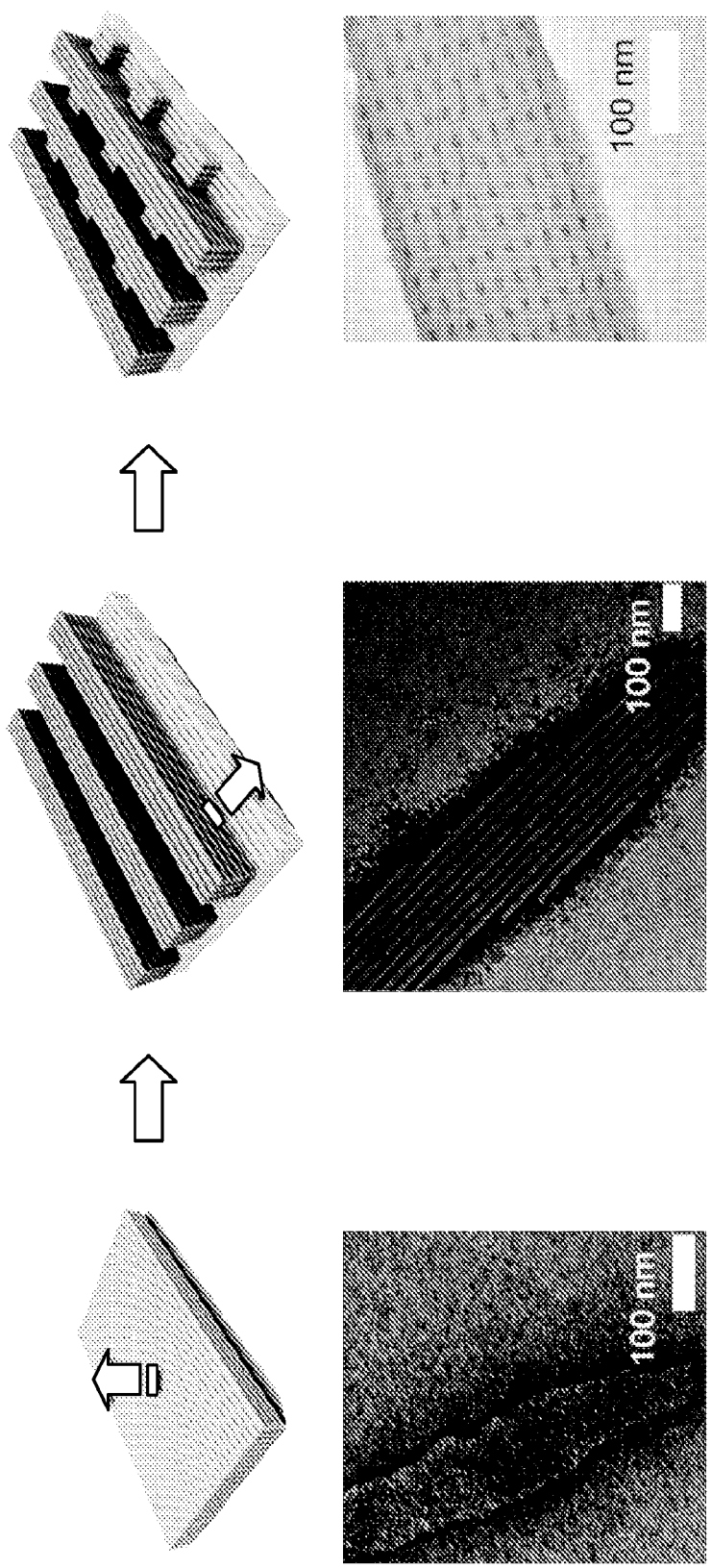
FIG. 14 shows the 3D epitaxial growth of a DNA template. The top panel is the design schematic. Starting from a 2D DNA seed (left, bright white rectangular cuboid, arrow indicates the growth direction), the first growth stage produces vertically aligned trenches (middle, dark rectangular cuboid) onto the seed (middle, bright white rectangular cuboid). The second continuous growth stage further produces laterally aligned ridges (right, light gray cuboid) connecting the vertically aligned trenches (right, dark rectangular cuboid). The bottom panel is the TEM images for each growth stage. Left is the TEM image for the seed (gray region with irregular edges). Middle is the TEM image after the first growth stage (gray parallel lines are the parallel trenches). Right is the TEM image after the secondgrowth stage (gray grids are the surface morphology, while the dark spots are the cavity surrounded by the DNA structures). The scale bar is 100 nm.

And exemplary non-limiting process of epitaxial growth is illustrated in FIG. 14 and described in greater detail in Example 6. One of ordinary skill in the art will recognize that the example is provided as guidance.

Moieties

Substrates (e.g., nucleic acid nanostructure/crystals) of the present disclosure may be coupled to moieties. Examples of moieties used include, without limitation, semiconductor particles, metal particles, carbon nanotubes, polymeric wires, Si nanowires, ceramic nanoparticles, metal oxide nanoparticles, fluoride nanoparticles, single-stranded or double-stranded nucleic acid (e.g., DNA, RNA, LNA, PNA), including self-assembled nucleic acid structures. Moieties used for coupling may also include, without limitation, plasmonic nanomaterials, fluorescent/luminescent nanomaterials, ferromagnetic nanomaterials, paramagnetic nanomaterials, antiferromagnetics nanomaterials, superparamagnetic nanomaterials, semiconductor nanomaterials, conductor nanomaterials or insulator nanomaterials.

In some embodiments, a nanostructure (i.e., crystal) is coupled with nanoparticles (e.g., gold, silver, copper, and/or nickel nanoparticles) or other components (e.g., metal clusters, oxides (e.g., $SiO_2$, $TiO_2$), chalcogenides (e.g., CuS, $Ag_2S$), nanowires (e.g., CNT, Si nanowires), polymers (e.g., PS, PMMA) and/or biomolecules (e.g., proteins, peptides, actin filaments)).

In some embodiments, a moiety comprises a semiconductor material. Semiconductor materials include, without limitation, Group IV elemental semiconductors, Group IV compound semiconductors, Group VI elemental semiconductors, Group III-V semiconductors, Group II-VI semiconductors, Group I-VII semiconductors, Group IV-VI semiconductors, Group IV-VI semiconductors, Group V-VI semiconductors, Group II-V semiconductors, oxides, layered semiconductors, magnetic semiconductors, organic semiconductors, charge-transfer complexes and combinations thereof.

In some embodiments, a moiety comprises a Group IV semiconductor material. Examples of Group IV semiconductor materials for use in accordance with the present disclosure include, without limitation, diamond, silicon, germanium, gray tin, silicon carbide and combinations thereof.

In some embodiments, a moiety comprises a Group VI semiconductor material. Examples of Group VI semiconductor materials for use in accordance with the present disclosure include, without limitation, sulfur, gray selenium, tellurium and combinations thereof.

In some embodiments, a moiety comprises a Group III-V semiconductor material. Examples of Group III-V semiconductor materials for use in accordance with the present disclosure include, without limitation, boron nitride, cubic, boron nitride, hexagonal, boron phosphide, boron arsenide, boron arsenide, aluminium nitride, aluminium phosphide, aluminium arsenide, aluminium antimonide, gallium nitride, gallium phosphide, gallium arsenide, gallium antimonide, indium nitride, indium phosphide, indium arsenide, indium antimonide and combinations thereof.

In some embodiments, a moiety comprises a Group II-VI semiconductor material. Examples of Group II-VI semiconductor materials for use in accordance with the present disclosure include, without limitation, cadmium selenide, cadmium sulfide, cadmium telluride, zinc oxide, zinc selenide, zinc sulfide, zinc telluride, cuprous chloride, copper sulfide, lead selenide, lead(ii) sulfide, lead telluride, tin sulfide, tin sulfide, tin telluride, lead tin telluride, thallium tin telluride, thallium germanium telluride, bismuth telluride and combinations thereof.

In some embodiments, a moiety comprises a Group I-VII semiconductor material. Examples of Group I-VII semiconductor materials for use in accordance with the present disclosure include, without limitation, cuprous chloride, copper sulfide and a combination of cuprous chloride and copper sulfide.

In some embodiments, a moiety comprises a Group IV-VI semiconductor material. Examples of Group IV-VI semiconductor materials for use in accordance with the present disclosure include, without limitation, lead selenide, lead(ii) sulfide, lead telluride, tin sulfide, tin sulfide, tin telluride, lead tin telluride, thallium tin telluride, thallium germanium telluride and combinations thereof.

In some embodiments, a moiety comprises a Group V-VI semiconductor material. An example of a Group IV-VI semiconductor material for use in accordance with the present disclosure includes, without limitation, bismuth telluride.

In some embodiments, a moiety comprises a Group II-V semiconductor material. Examples of Group II-V semiconductor materials for use in accordance with the present disclosure include, without limitation, cadmium phosphide, cadmium arsenide, cadmium antimonide, zinc phosphide, zinc arsenide, zinc antimonide and combinations thereof.

In some embodiments, a moiety comprises an oxide. Examples of oxides for use in accordance with the present disclosure include, without limitation, titanium dioxide, anatase, titanium dioxide, rutile, titanium dioxide, brookite, copper(i) oxide, copper(ii) oxide, uranium dioxide, uranium trioxide, bismuth trioxide, tin dioxide, barium titanate, strontium titanate, lithium niobate, lanthanum copper oxide and combinations thereof.

In some embodiments, a moiety comprises a layered semiconductor. Examples of layered semiconductors for use in accordance with the present disclosure include, without limitation, lead(ii) iodide, molybdenum disulfide, gallium selenide, tin sulfide, bismuth sulfide and combinations thereof.

In some embodiments, a moiety comprises a magnetic semiconductor. Examples of magnetic semiconductors for use in accordance with the present disclosure include, without limitation, gallium manganese arsenide, indium manganese arsenide, cadmium manganese telluride, lead manganese telluride, lanthanum calcium manganate, iron(ii) oxide, nickel(ii) oxide, europium(ii) oxide, europium(ii) sulfide, chromium(iii) bromide and combinations thereof.

Other examples of semiconductor materials that may be used in accordance with the present disclosure include, without limitation, copper indium selenide, cis, silver gallium sulfide, zinc silicon phosphide, arsenic sulfide, platinum silicide, bismuth(iii) iodide, mercury(ii) iodide, thallium(i) bromide, silver sulfide, iron disulfide, copper zinc tin sulfide, copper zinc antimony sulfide and combinations thereof.

In some embodiments, a moiety comprises a chalcogenide. A chalcogenide is a chemical compound that includes at least one chalcogen anion and at least one more electropositive element. In some embodiments, the chalcogenide is a sulfide, selenide or a telluride.

In some embodiments, a moiety comprises an electrical insulator. An electric insulator is a material with internal electric charges that do not flow freely, and therefore make it difficult to conduct an electric current under the influence of an electric field.

In some embodiments, a moiety comprises a metal. Examples of metals that may be used in accordance with the present disclosure include, without limitation, gold, aluminium, chromium, titanium, tungsten, tantalum, niobium, platinum, zinc and combinations thereof.

In some embodiments, a moiety comprises carbon, SiC, $LiNbO_3$, $PbZrTiO_3$, $HfO_2$, $TiO_2$, $V_2O_5$, $Al_2O_3$, $Ta_2O_3$ or combinations thereof.

In some embodiments, a moiety comprises a polymer. Examples of polymers that may be used in accordance with the present disclosure include, without limitation, polydimethylsiloxane (PDMS), poly(methyl methacrylate) (PMMA) (e.g., PMMA resin), and self-assembling polymers. Other polymer examples are provided herein including copolymer P(MMA-MAA) and self-assembling block copolymers.

In some embodiments, the diameter (or dimension, including longest or average dimension) of the moieties is 1 nm to 100 nm (e.g., 1 to 75 nm, 1 to 50 nm, 1 to 25 nm).

In some embodiments, the moieties are comprised of a heterogeneous mixture of moieties. For example, a substrate may comprise a mixture of different semiconductor moieties, a mixture of nanoparticles of different sizes, or a mixture of nanoparticles and nanowires.

Coupling of Moieties to Substrates

Substrates (e.g., nucleic acid nanostructures/crystals) of the present disclosure may be coupled, in a prescribed manner, to moieties, such as nanoparticles (e.g., gold nanoparticles) and/or nanowires (e.g., carbon nanotubes). "Coupling" herein refers to the confinement of a moiety to a location of a substrate. A moiety may be coupled covalently or non-covalently to a substrate. In some embodiments, moieties (e.g., nanoparticles) are coupled to a substrate via complementary partially or wholly single-stranded nucleic acids (e.g., DNA or RNA), referred to as handles and anti-handles. In some embodiments, a handle (or anti-handle) is coupled covalently or non-covalently to a substrate. In some embodiments, a handle (or anti-handle) is coupled to a nucleic acid nanostructure (i.e., crystal) substrate by hybridization. In some embodiments, a handle (or anti-handle) is coupled to a substrate through a binding pair. In some instances, the binding pair is biotin and streptavidin.

Similarly, in some embodiments, a handle (or anti-handle) is coupled covalently or non-covalently to moiety (e.g., nanoparticle, such as a gold nanoparticle, or a nanowire such as a carbon nanotube). In some embodiments, a handle (or anti-handle) is coupled to a moiety through a binding pair.

In some embodiments, each anti-handle is coupled to an individual moiety. For example, each anti-handle may be coupled to only one moiety. In some embodiments, a single anti-handle is coupled to more than one (e.g., 2, 3 or 4) moiety.

In some embodiments, a subset of anti-handles is coupled to the same moiety. Thus, a single moiety (e.g., a nanowire) may be coupled to multiple anti-handles.

In some embodiments, substrates are coupled to handles and/or moieties are coupled to an anti-handle through —SH groups (e.g., for metal and semiconducting moieties), click chemistry, —$NH_2$ groups, —COOH groups (e.g., for silica or polymer coated moieties), π-π stacking (e.g., to wrap single-stranded DNAs onto carbon nanotubes), coordinating interation (Ni2+/polyhistidine), or through electrostatic interactions (e.g., for charged nanoparticles or molecules).

It should be understood that with a handle/anti-handle configuration, the handle is coupled to the nucleic acid nanostructure (i.e., crystal) and the complementary anti-handle is coupled to the moiety, or alternatively, the handle is coupled to the moiety and the complementary anti-handle is coupled to the nucleic acid nanostructure such that hybridization of the handle and anti-handle pair results in coupling of the moiety to the nucleic acid nanostructure.

A handle (or anti-handle) may be coupled to a substrate (e.g., nucleic acid nanostructure (i.e., crystal)) or a moiety in a covalent or non-covalent manner. As a non-limiting example, it may be coupled non-covalently to a substrate using a binding pair such as a biotin and avidin/streptavidin binding pair. Other binding pairs will be apparent to those of ordinary skill in the art and may be used for coupling, including high affinity protein/protein binding pairs such as antibody/antigen and ligand/receptor binding pairs, hydrophobic interactions, π-π stacking or electrostatic interactions. In some embodiments, moieties are coupled to a substrate through spatial confinement.

The length of a nucleic acid handle (or anti-handle) may vary. In some embodiments, In some embodiments, a moiety can be coupled to a substrate without being conjugated to an intermediate nucleic acid (e.g., a nucleic acid, such as a handle/anti-handle, that is not contributing to the structural integrity of the nanostructure (i.e., crystal)). In such embodiments, the moiety can be coupled to the substrate via a binding pair such as a biotin and avidin/streptavidin binding pair.

A handle (or at least the single-stranded region of the handle) may be about 15 to about 50 nucleotides in length. In some embodiments, a handle (or anti-handle) may be about 15, about 20, about 25, about 30, about 35, about 40, or about 50 nucleotides in length. Depending on the application, a nucleic acid handle (or anti-handle) may be greater than 50 nucleotides in length.

In some embodiments, coupling of moieties to a substrate (e.g., a nucleic acid nanostructure/crystal) does not require an intermediate molecular interaction (e.g., nucleic acid hybridization or protein-protein interactions). In some embodiments, moieties are "confined" to a substrate such that the moieties are held in close proximity within a channel (or trough, reservoir, groove or other recessed feature relative to the surface) of the substrate due to the relative shape and/or size of the channel and the moiety. This confinement may be achieved by designing/providing a substrate containing a channel that conforms to the shape of the moiety being confined and has a diameter no greater than the diameter of the moiety being confined. For example, with reference to FIG. 3A, nanowires may be confined within a channel of a substrate with handles and anti-handles (as shown) or without (not shown). In some embodiments, a channel has a diameter that is equal to the diameter of the moiety being confined. In some embodiments, a channel has a diameter that is slightly less than the diameter of the moiety being confined.

Figure 1A:
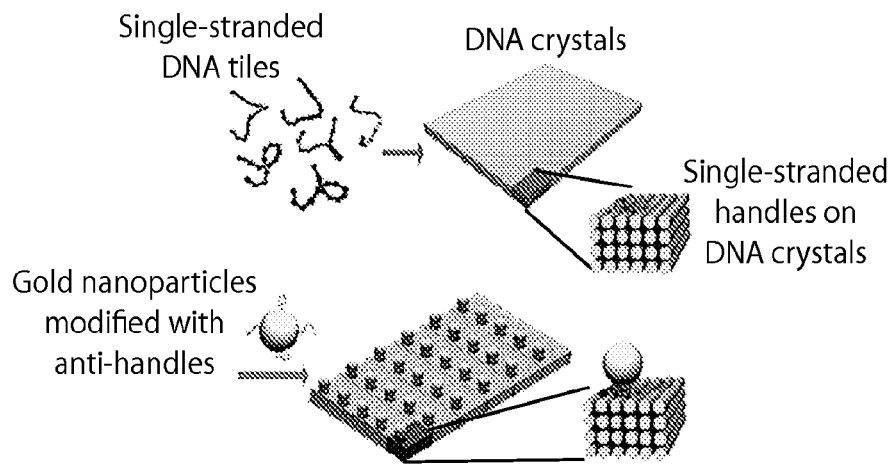
FIGS. 1A-1B show the alignment of nanoparticles into prescribed architectures on three-dimensional (3D) DNA crystals.
Figure 1B:
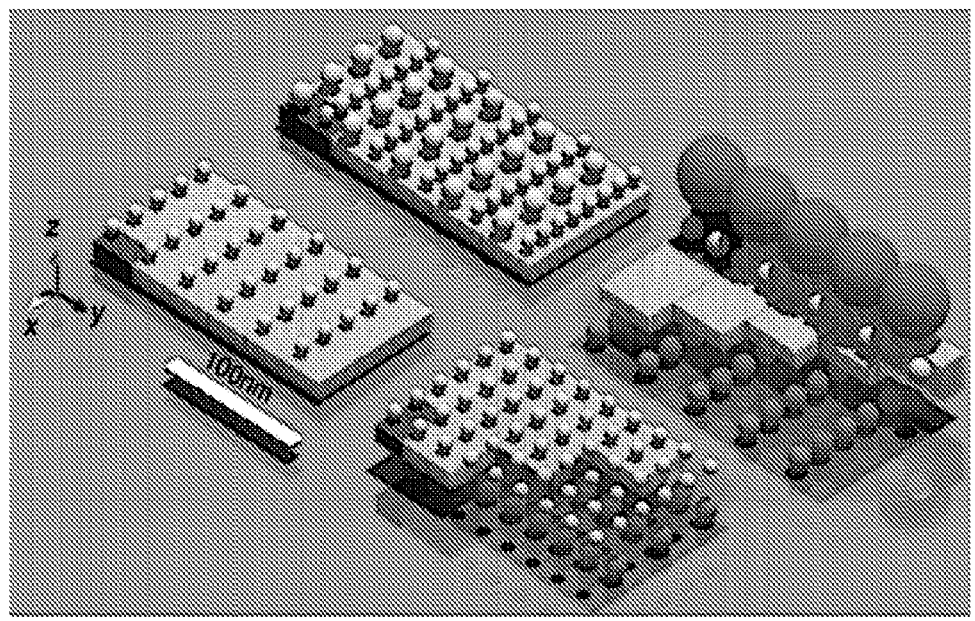

Moieties may be arranged on or within a substrate to form a particular configuration or shape. In some embodiments, moieties may be arranged on or within a substrate to form a crossbar configuration, a chiral configuration or parallel rows. An example of a configuration of parallel rows is shown in FIGS. 1A-1B. Particular configurations may be prescribed, for example, by positioning handles or other coupling molecules at prescribed positions on or in the substrate. As shown in FIG. 1A, subsets of nucleic acid handles may be aligned such that when bound to complementary anti-handles that are attached to moieties, the resulting configuration contains parallel rows of moieties. Particular configurations may be prescribed, for example, by providing a pre-formed or pre-assembled substrate containing channels or other recessed features arranged in a particular manner. As shown in FIG. 3B, the DNA crystal substrate contains channels configured in a parallel arrangement, and nanowires are then coupled or confined to those channels, resulting in a substrate having parallel (or substantially parallel) rows of coupled or confined moieties.

In some embodiments, nucleic acid handles are coupled to channels formed in the substrate. A substrate may comprise, for example, 1, 2, 3, 4, 5, 6, 7, 8, 9, 10 or more channels, each having the same width or different widths relative to one another.

A single substrate may contain a homogeneous population or a heterogeneous population of moieties. For example, a population of moieties of a substrate may contain a subpopulation of moieties of one material, another population of moieties of another material, and so on. In some embodiments, a population of moieties of a substrate may contain moieties of different sizes and/or materials. Other mixed populations are contemplated herein.

The number and/or heterogeneity of moieties on a substrate, in some embodiments, is prescribed by size of the substrate, dimension of the substrate and steric hindrance of the moieties. For example, a 1 μm×1 μm×1 μm 3D substrate may contain as many as 3000 moieties (a homogeneous or heterogeneous population). As another example, a 100 μm×100 μm×100 μm 3D substrate may contain as many as a million moieties (a homogeneous or heterogeneous population).

Substrates coupled to moieties as provided herein, in some embodiments, have spatial resolutions of 1 nm to 1 μm. For example, substrates (e.g., nucleic acid nanostructure (i.e., crystals)) may have a feature resolution of 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm or 1000 nm. In some embodiments, substrates have a feature resolution of 1 nm to 100 nm, 1 nm to 50 nm, or 1 nm to 10 nm, 1 nm to 5 nm, or 1 nm to 2 nm. In some embodiments, substrates have a feature resolution of less than 50 nm, less than 25 nm, less than 10 nm, or less than 5 nm. In some embodiments, substrates have a feature resolution of 1 nm to less than 10 nm, 2 nm to 10 nm or 2 nm to 5 nm.

"Spatial resolution" refers to distinguishable details of a substrate, such as a nucleic acid nanostructure (e.g., in the context of nucleic acid self-assembly). The terms "spatial resolution" and "feature resolution" may be used herein interchangeably. This resolution is determined by the spatial accuracy and precision of each nucleic acid strand in a nucleic acid crystals, which can be validated on the synthesized nucleic acid nanostructures (i.e., crystals) by, for example, transmission electron microscopy (TEM) and atomic force microscopy (AFM). For two-dimensional nucleic acid nanostructures (i.e., crystals), spatial/feature resolution describes the spatial distinguishability in two-dimensional aspects (e.g., in the X and Y planes). For three-dimensional nucleic acid nanostructures (i.e., crystals), the spatial/feature resolution divides into horizontal and vertical aspects, describing the spatial distinguishability for X/Y plane and Z direction, respectively.

Pattern Transfer Processes

Some aspects of the present disclosure relate to pattern transfer processes, such as lithography, that utilize etching, which is based on the concept of masking, in which a "mask" protects a substrate from reacting with a harsh etchant. "Etching" refers to a process by which material is removed from a substrate (e.g., using an etchant) resulting in patterning of the substrate. Etching may be considered "wet" or "dry." Wet etching refers to an etching process that utilizes liquid chemicals (also referred to as wet etchants) to remove materials from a substrate, usually in specific patterns defined by a photoresist mask on the substrate. The present disclosure contemplates the use of bare three-dimensional nucleic acid nanostructures as masks on a substrate. Material not covered by the mask is "etched away" by the chemicals, while material covered by the mask is left almost intact. By comparison, dry etching refers to an etching process that does not utilize liquid chemicals to remove material from a substrate. In some embodiments, methods of the present disclosure include dry etching conditions. Dry etching may be accomplished, in some embodiments, through chemical reactions that consume the material (e.g., using chemically reactive gases, radicals or plasma), through physical removal of the material (e.g., by momentum transfer from inert gases or inert ion beam), or through a combination of both physical removal and chemical reactions.

Examples of dry etching pattern transfer processes include, without limitation, ion beam etching, electron beam etching and X-ray etching.

In some embodiments of the present disclosure, ion beam etching (see, e.g., Matsui S. et al. *Nanotechology*, 7(3): 247, 1996, incorporated by reference herein) is used to pattern a substrate. Ion beam etching may include bombarding the material to be etched with highly energetic chemically reactive ions. Such bombardment with energetic ions dislodges atoms from the material, in effect achieving material removal by sputtering. In some embodiments, reactive ion etching is used to pattern a substrate. Reactive ion etching (see, e.g., Wu B. et al. J. of App. Phys. 108(5): 051101, 2010, incorporated by reference herein) uses chemically reactive ion and neutral beam (e.g., plasma) to remove material from a substrate. In some embodiments of the present disclosure, reactive ion etching may include the following steps: (1) generation of reactive species (ions and/or radicals) in a plasma; (2) diffusion of these species to the surface of the material being etched; (3) adsorption of these species on the surface; (4) occurrence of chemical reactions between the species and the material being etched, forming volatile byproducts; (5) desorption of the byproducts from the surface; and (6) diffusion of the desorbed byproducts into the bulk of the gas.

In some embodiments of the present disclosure, electron beam etching (Randolph S. J. et al. *Critical Reviews in Solid State and Materials Sciences* 31(3): 55, 2006, incorporated by reference herein) is used to pattern a substrate. Electron beam etching involves the adsorption of a gas phase precursor on the surface of a substrate. During exposure of the surface by the electron beam, there is a probability that primary electrons or secondary electrons will cause the otherwise stable, physisorbed precursor to dissociate and react with surface atoms. The product of the reaction, typically a volatile species, desorb from the surface, and new bulk material is revealed as surface, providing new adsorption sites for precursor gas molecules to repeat the process and etch the material.

In some embodiments of the present disclosure, X-ray etching (Dimitrakakis C., et al. *Chem. Commun.* 48: 7483, 2012, incorporated by reference herein) is used to pattern a substrate. X-ray etching involves the use of x-rays to transfer a pattern from a mask to a substrate.

Some aspects of the present disclosure relate to two- or three-dimensional patterning of substrates. For example, a bare nucleic acid (e.g., DNA) nanostructure mask of the present disclosure may be applied to a substrate (e.g., silicon wafer) and, in some instances, may adhere to the substrate. Substrates used in accordance with the present disclosure may comprise, without limitation, silicon, silicon dioxide (also referred to as silica), aluminum oxide, sapphire, germanium, gallium arsenide (GaAs), an alloy of silicon and germanium, or indium phosphide (InP).

A substrate may be inorganic or organic.

In some embodiments, a substrate comprises a semiconductor material, as described elsewhere herein.

In some embodiments, a bare nucleic acid nanostructure is adsorbed onto a surface of a substrate. Typically, but not always, a substrate, as described herein, is a planar substance having a top surface (see, e.g., FIGS. 2A-C) onto which the bare nucleic acid nanostructure is deposited/adsorbed. Nucleic acid adsorption can be achieved by, for example, physisorption, electrostatic absorption or chemical absorption.

In some embodiments, adsorption of a bare nucleic acid nanostructure onto a surface of a substrate is driven by physisorption. For example, an intact substrate may be used for incubation of a bare nucleic acid nanostructure in solution. In some embodiments, a flat substrate is carved to form grooves. These grooves trap nucleic acid nanostructures and increase the deposition yield.

In some embodiments, adsorption of a bare nucleic acid nanostructure onto a surface of a substrate is driven by electrostatic absorption. For example, a substrate may be incubated initially with $Mg^{2+}$ solution to produce an $Mg^{2+}$ saturated substrate. The $Mg^{2+}$ saturated substrate is then used for bare nucleic acid nanostructure deposition.

In some embodiments, adsorption of a bare nucleic acid nanostructure onto a surface of a substrate is driven by chemical absorption. For example, a substrate may be modified with an amino-containing reagent, such as, for example, polylysine, amino silane or polyethylenimine poly(allylamine hydrochloride) to produce a chemically-modified substrate. The chemically-modified substrate is then used for bare nucleic acid nanostructure adsorption.

In some embodiments, adsorption of a bare nucleic acid nanostructure onto a surface of a substrate is driven by bimolecular binding. For example, a substrate may be modified with streptavidin, which can bind biotin-labeled bare nucleic acid nanostructures.

In some embodiments, nucleic acid nanostructures (e.g., bare nucleic acid nanostructures) of the present disclosure are assembled in or transferred to a solution (e.g., water). In some embodiments, the concentration of the bare nucleic acid nanostructure in solution is 10 pM-1 µM. For example, the concentration of the bare nucleic acid nanostructure in solution may be 10 pM to 1 nM, 10 pM to 500 pM, 500 pM to 1 nM, 1 nM to 500 nM, or 500 nM to 1 µM. In some embodiments, the concentration of the bare nucleic acid nanostructure in solution is 10 pM, 50 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, 1 nM, 10 nM, 50 nM, 100 nM, 150 nM, 200 nM, 250 nM, 300 nM, 350 nM, 400 nM, 450 nM, 500 nM, 550 nM, 600 nM, 650 nM, 600 nM, 750 nM, 800 nM, 850 nM, 900 nM, 950 nM or 1 µM, or more. The foregoing concentrations, in some embodiments, are appropriate for nucleic acid nanostructures that are at least 30 nucleotides in length.

In some embodiments, a solution that includes bare nucleic acid nanostructures is permitted to incubate on a substrate during an adsorption step for 5 minutes (min) to 10 hours (hrs). For example, a solution that includes bare nucleic acid nanostructures may be permitted to incubate on a substrate during an adsorption step for 5 min, 10 min, 15 min, 20 min, 30 min, 45 min, 60 min, 2 hrs, 2.5 hrs, 3 hrs, 3.5 hrs, 4 hrs, 4.5 hrs, 6 hrs, 6.5 hrs, 7 hrs, 7.5 hrs, 8 hrs, 8.5 hrs, 9 hrs, 9.5 hrs or 10 hrs, or more. In some embodiments, a solution that includes bare nucleic acid nanostructures is permitted to incubate on a substrate during an adsorption step for 30 minutes to 4 hours.

In some embodiments, 1 µl-10 µl or about 1-100 µl of solution per $cm^2$ substrate is/are adsorbed on a substrate during an adsorption step. For example, the volume of solution deposited per $cm^2$ substrate may be 1 µl, 2 µl, 3 µl, 4 µl, 5 µl, 6 µl, 7 µl, 8 µl, 9 µl, 10 µl, or 100 µl or more.

In some embodiments, 1 µl-10 µl of a solution containing a concentration of bare nucleic acid nanostructure of 10 pM-1 µM is adsorbed on a substrate for 15 minutes to 4 hours.

Figure 8:
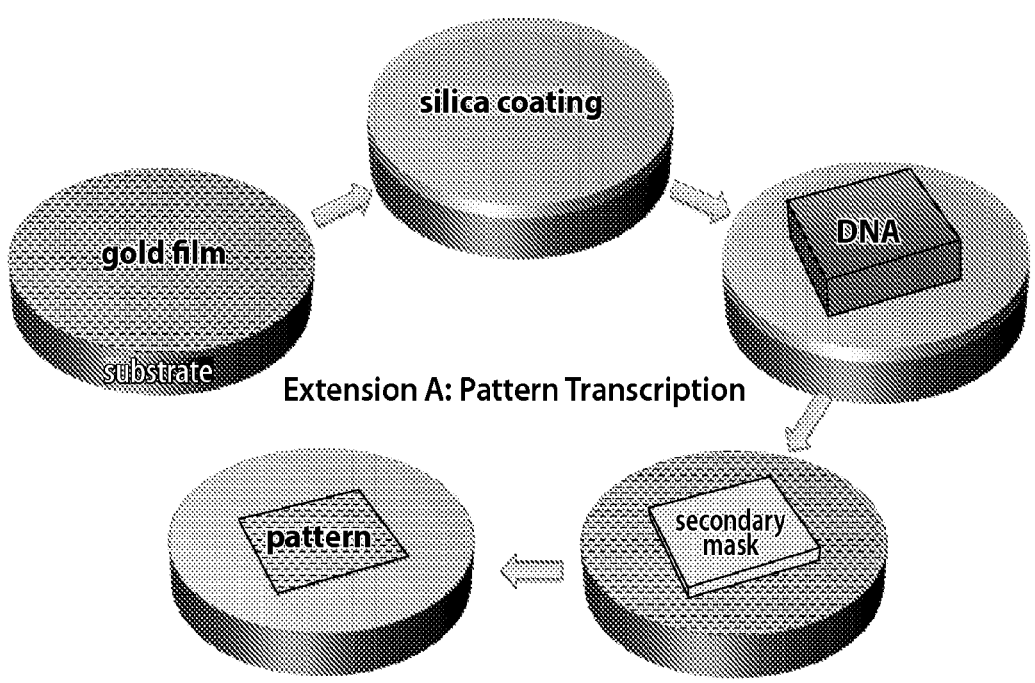
FIG. 8 shows a schematic of one embodiment of a DNA lithography method of the present disclosure. A bare DNA nanostructure mask functionalized with gold nanoparticles is adsorbed onto a substrate, and then the substrate onto which the bare DNA nanostructure mask was adsorbed is etched under reactive ion etching conditions, thereby producing a pattered substrate functionalized with gold nanoparticles. Alternatively, the method may involve coating a substrate with a thin layer of $SiO_2$ which serves as a hard mask layer. Then a bare nanostructure is adsorbed onto the SiO2 layer, followed by reactive ion etching to fabricate a $SiO_2$ hard mask with a prescribed pattern. Then the substrate with its $SiO_2$ hard mask can be treated by dry/wet etching protocol to obtain the prescribed metallic nanopattern.

Substrates of the present disclosure may contain a single layer of material or may contain multiple layers (e.g., 2, 3, 4 or 5 layers) of different materials (FIG. 8). For example, some aspects of the present disclosure contemplate adsorbing a bare nucleic acid nanostructure onto a first substrate layer that is positioned above a second substrate layer, etching the surface of the first substrate layer containing the bare nucleic acid nanostructure using dry etching, thereby producing a secondary mask that is positioned above the second substrate layer, and etching the second substrate layer containing the secondary mask using dry etching or wet etching, thereby producing a patterned substrate. As shown in FIG. 8, for example, a substrate with a gold film layer is coated with a layer of silica ("silica coating"). A bare nucleic acid nanostructure mask (cube nanostructure shown) is then adsorbed onto the silica coating layer, followed by dry etching. The remaining patterned silica serves the function of a secondary mask for further etching, resulting in a patterned gold film. Each layer of a multiple layered substrate may be a substrate material selected from any of those provided herein (e.g., silicon, silica, an oxide, a nitride, a metal, a non-metal, a semiconductor, and/or a polymer).

Patterned Substrates and Devices

Use of nucleic acid nanostructure masks with, for example, metal coatings leads to a significant loss of resolution. Advantageously, the bare nucleic acid nanostructure masks provided herein, do not have such coatings, and, thus, high feature resolution is achieved, in some embodiments of the present disclosure. Methods provided herein permit the patterning of substrates into two- and three-dimensional shapes with feature resolutions of 1 nm to 1 µm. For example, patterned substrates may have a feature resolution of 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm or 1000 nm. In some embodiments, patterned substrates have a feature resolution of 1 nm to 100 nm, or 1 nm to 10 nm. In some embodiments, patterned substrates have a feature resolution of less than 10 nm, or less than 5 nm. In some embodiments, patterned substrates have a feature resolution of 1 nm to 2 nm.

In some embodiments, pattered substrates having a feature resolution of less than 10 nm, or less than 5 nm. In some embodiments, a patterned substrate has a feature resolution of 1 nm to 1 µm. In some embodiments, a patterned substrate has a feature resolution of 5 nm to 1 µm. In some embodiments, a patterned substrate has a feature resolution of 1 nm to 2 nm.

As described above, "feature resolution" of a nucleic acid nanostructure refers to resolution in the context of nucleic acid nanostructure self-assembly—that is, the term refers to distinguishable details of a nucleic acid nanostructure. For three-dimensional nucleic acid nanostructures, the feature resolution divides into horizontal and vertical aspects, describing the spatial distinguishability for X/Y plane and Z direction, respectively.

In some embodiments, methods provided herein permit the patterning of substrates into two- and three-dimensional shapes with etching resolutions of 1 nm to 1 µm. For example, patterned substrates may have an etching resolution of 1 nm, 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm or 1000 nm. In some embodiments, patterned substrates have an etching resolution of 1 nm to 100 nm, or 1 nm to 10 nm. In some embodiments, patterned substrates have an etching resolution of less than 10 nm, or less than 5 nm. In some embodiments, patterned substrates have an etching resolution of 1 nm to 2 nm.

"Etching resolution" of a nucleic acid nanostructure refers to resolution in the context of transcribing structural details from a nucleic acid nanostructure to a substrate in the event of etching a prescribed pattern. This resolution is determined by the spatial accuracy and precision of chemical/physical etching on a substrate in the presence of a nucleic acid nanostructure, which could be validated on a patterned substrate by scanning electron microscopy (SEM) and AFM. Similar to the feature resolution of a nucleic acid nanostructure, etching resolution can be divided into two-dimensional and three-dimensional aspects, according to the nucleic acid nanostructure characteristics and etching demands. In some embodiments, etching resolution matches the feature resolution, showing the same distinguishable scale. In some embodiments, due to, for example, potential distortion and defect problem, etching resolution of a nucleic acid nanostructure may be lower than the feature resolution of the nucleic acid nanostructure.

Patterned substrates with such feature resolutions are particularly useful for the production of, for example, modern electronic devices, plasmonic devices, photonic devices, photovoltaic devices and hybrid devices. Examples of such devices include, without limitation, circuits (Gudiksen, M. S. et al. *Nature* 415: 617-620, 2002, incorporated by reference herein), integrated circuits (McAlpine, M. C. et al. *Nature Materials* 6: 379-384, 2007, incorporated by reference herein), capacitance (Yu, C. et al. *Adv. Mater.* 21: 4793-4797, 2009, incorporated by reference herein), transistor (e.g., electrical or optical modulated) (Dattoli, E. N., et al. *Nano Letters* 7: 2463-2469, 2007, incorporated by reference herein), waveguide (Pavesi, L. et al. *Nature* 408: 440-444, 2000, incorporated by reference herein), laser resonance cavities (Noda, S. et al. *Nature Photonics* 1: 449-458, 2007, incorporated by reference herein), FANO substrate (Luk'yanchuk, B. et al. *Nature Materials* 9: 707-715, 2010, incorporated by reference herein) and meta-materials (Schnell, M. et al. *Nature Photonics* 3: 287-291, 2009, incorporated by reference herein). Particular patterns of substrates are not limited. Recent advances in nucleic acid nanotechnology make it possible to construct arbitrary-shaped nucleic acid nanostructures at a theoretical precision down to 2 nm. Thus, bare nucleic acid nanostructure masks of the present disclosure can be created based, for example, on the particular end product device of interest (e.g., in the shape of a particular electronic device).

In some embodiments, patterned substrates of the present disclosure are "functionalized." A patterned substrate is considered functionalized if it contains a moiety that permits attachment of other substances to the substrate. Examples of moieties used for functionalizing a substrate include, without limitation, semiconductor particles, metal particles, carbon nanotubes, ceramic nanoparticles, metal oxide nanoparticles or fluoride nanoparticles. Moieties used for functionalizing a substrate may also include, without limitation, plasmonic nanomaterials, fluorescent/luminescent nanomaterials, ferromagnetic nanomaterials, paramagnetic nanomaterials, antiferromagnetics nanomaterials, superparamagnetic nanomaterials, semiconductor nanomaterials, conductor nanomaterials or insulator nanomaterials.

Figure 9A:
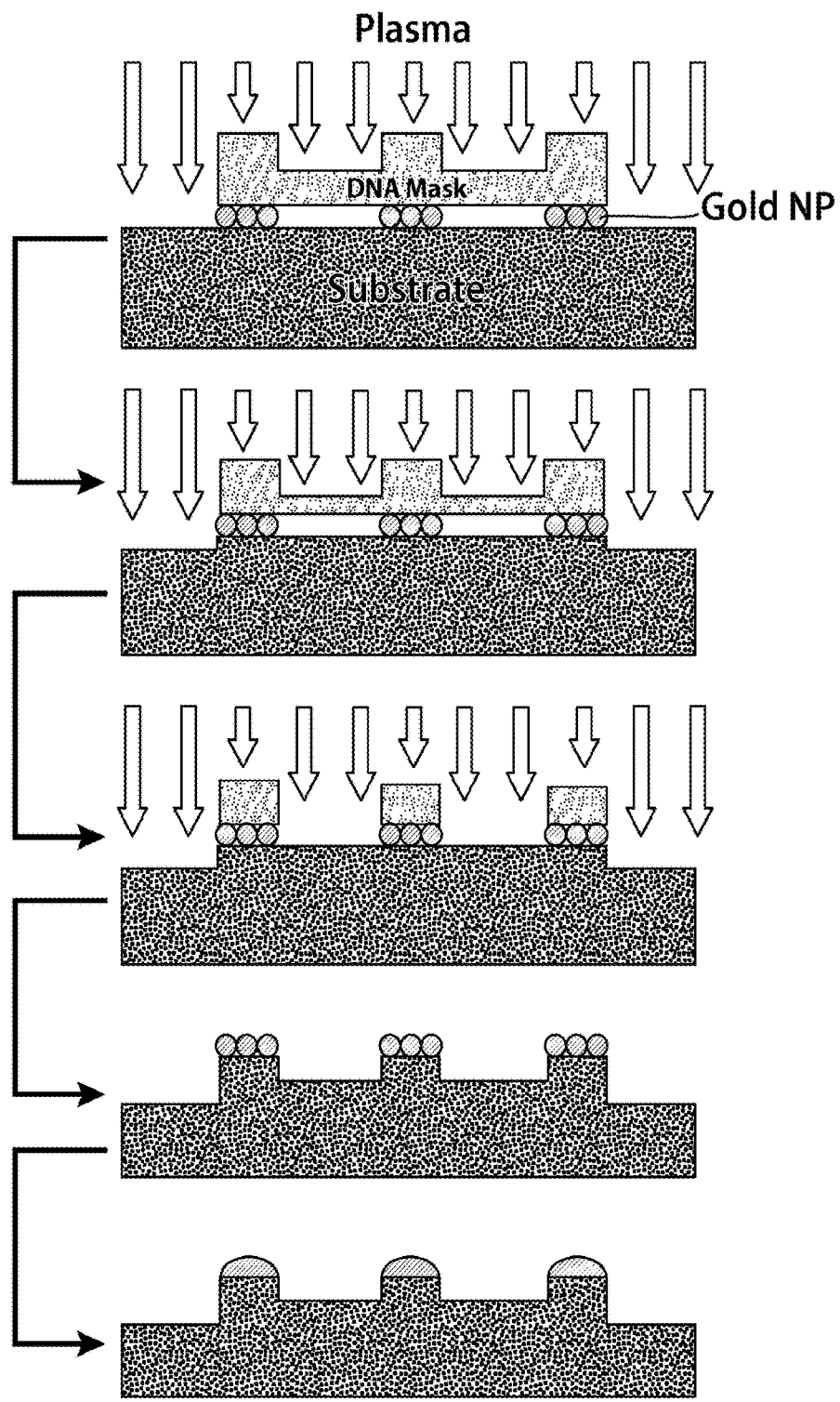
FIG. 9A shows a schematic of one embodiment of a DNA lithography method of the present disclosure. Gold nanoparticles are used to functionalize a bare DNA nanostructure mask for three-dimensional lithography. Gold nanoparticles remain on the three-dimensional patterned substrate after etching. Through, for example, epitaxial growth, the gold-patterned substrate can be further engineered for functions, such as, for example, electrode connections, waveguide construction, or other plasmonic or photovoltaic structures.
Figure 9B:
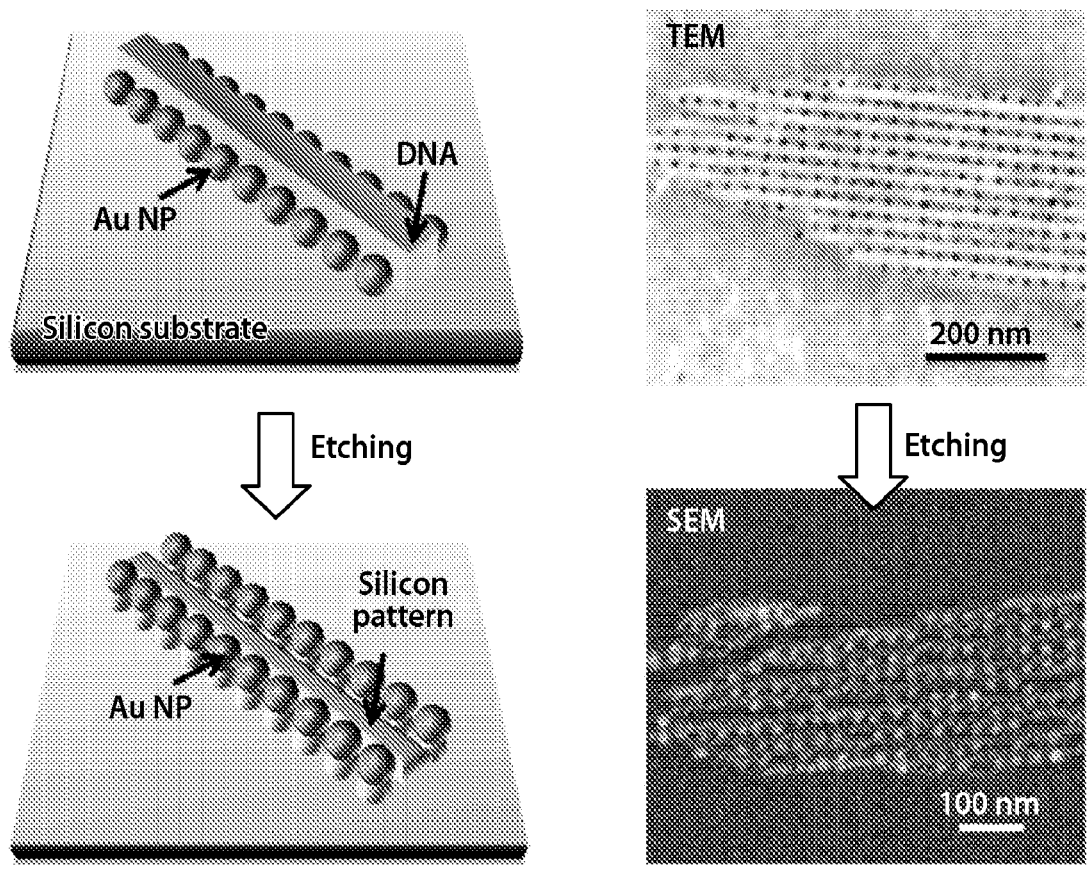
FIG. 9B shows an embodiment of etching a DNA template with an Au nanoparticle (NP) pattern. Au NPs are patterned in the grooves of a DNA brick crystal. After deposition, desalting, and drying, the silicon wafer carrying the DNA template-Au NPs composite was treated by reactive ion etching. Post-etching, Au NPs still preserved the original pattern, while the DNA ridges of the template generated silicon ridge patterns.
Figure 10A:
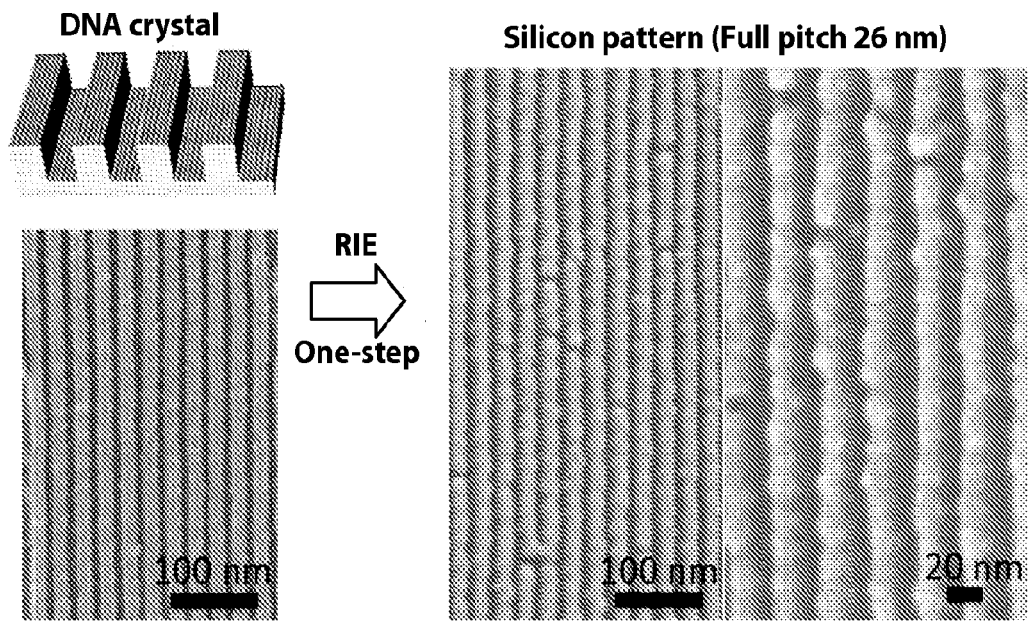
FIGS. 10A-10B show examples of various silicon patterns having different pitches (e.g., 26 nm, 16 nm and 10 nm).
Figure 10B:
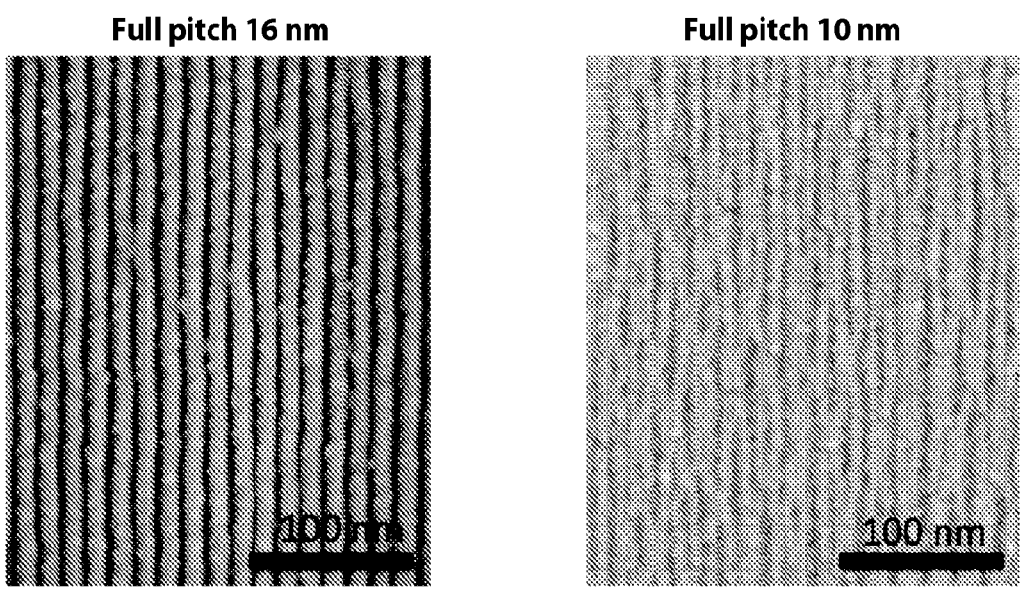
Figure 11:
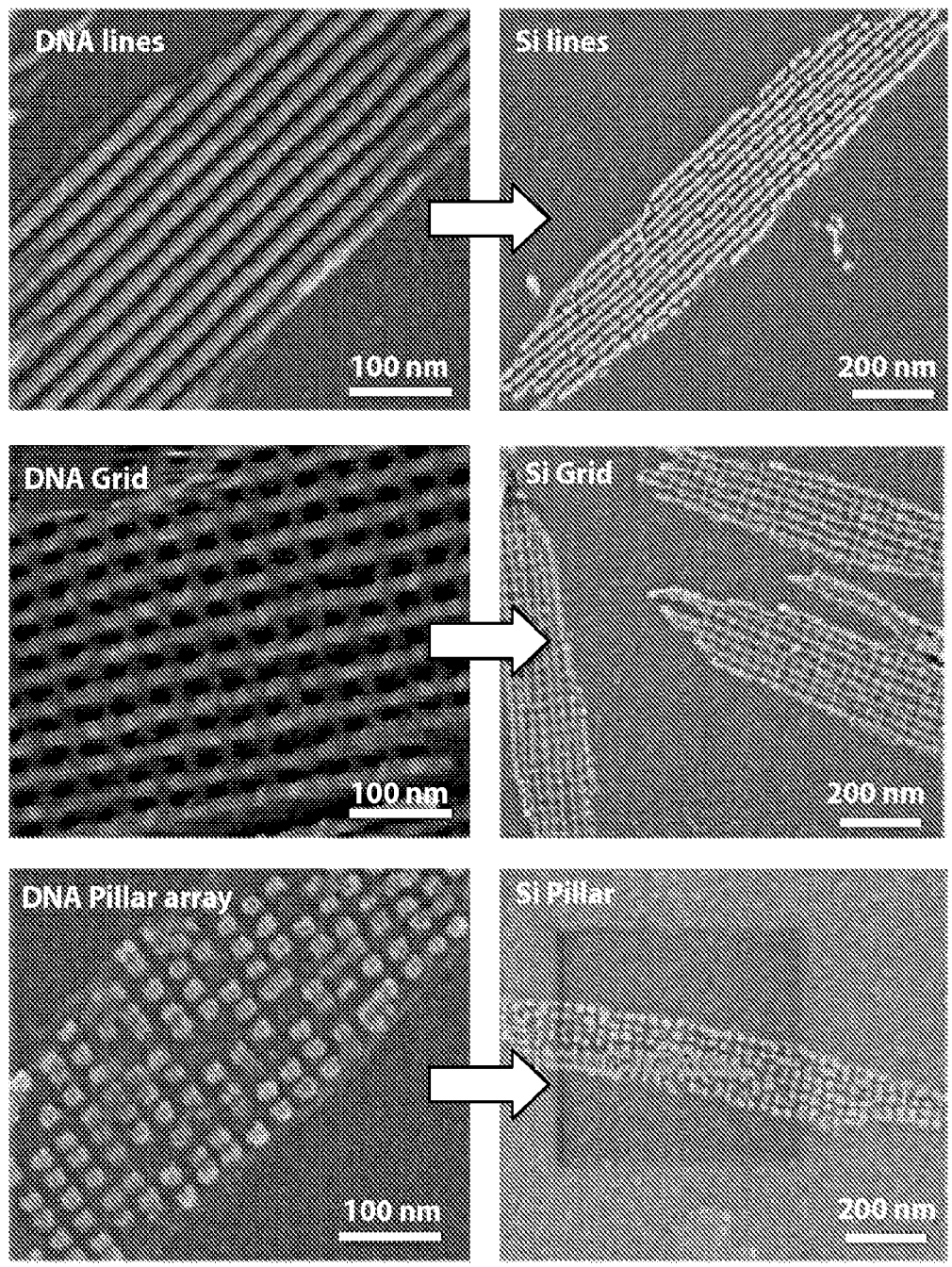
FIG. 11 shows images of DNA lines and Si lines, a DNA grid and a Si grid, and a DNA pillar array and a Si pillar array, generated according to the methods described herein.

In some embodiments, a bare nucleic acid nanostructure is functionalized with nanoparticles (e.g., gold, silver, copper, and/or nickel nanoparticles) or other components (e.g., metal clusters, oxides (e.g., $SiO_2$, $TiO_2$), chalcogenides (e.g., CuS, $Ag_2S$), nanowires (e.g., CNT, Si nanowires), polymers (e.g., PS, PMMA) and/or biomolecules (e.g., proteins, peptides, actin filaments)), for example, as shown in FIGS. 9A-B. It should be understood that nanoparticles or other components used to functionalize a bare nucleic acid nanostructure are not used to assist with etching of the bare nucleic acid nanostructure. Rather, the nanoparticles (e.g., gold nanoparticles or other metal nanoparticles) or other components become functional components of the patterned substrate (e.g., patterned substrate produced by a method of the present disclosure). In some embodiments, the nanoparticles or other components are "sandwiched" between the bare nucleic acid nanostructure and the surface of the substrate (see, e.g., FIG. 8).

Substrates, such as patterned substrates, coupled to moieties (e.g., nanoparticles and/or nanowires) and having such spatial resolutions are particularly useful for the production of, for example, modern electronic devices, plasmonic devices, photonic devices, photovoltaic devices and hybrid devices. Examples of such devices include, without limitation, circuits (Gudiksen, M. S. et al. *Nature* 415: 617-620, 2002, incorporated by reference herein), integrated circuits (McAlpine, M. C. et al. *Nature Materials* 6: 379-384, 2007, incorporated by reference herein), capacitance (Yu, C. et al. *Adv. Mater.* 21: 4793-4797, 2009, incorporated by reference herein), transistor (e.g., electrical or optical modulated) (Dattoli, E. N., et al. *Nano Letters* 7: 2463-2469, 2007, incorporated by reference herein), waveguide (Pavesi, L. et al. *Nature* 408: 440-444, 2000, incorporated by reference herein), laser resonance cavities (Noda, S. et al. *Nature Photonics* 1: 449-458, 2007, incorporated by reference herein), FANO substrate (Luk'yanchuk, B. et al. *Nature Materials* 9: 707-715, 2010, incorporated by reference herein) and meta-materials (Schnell, M. et al. *Nature Photonics* 3: 287-291, 2009, incorporated by reference herein). Particular designs of nanostructures (i.e., crystals) are not limited. Recent advances in nucleic acid nanotechnology make it possible to construct arbitrary-shaped nucleic acid nanostructures at a theoretical precision down to 2 nm. Thus, nucleic acid nanostructures of the present disclosure can be created based, for example, on the particular end product device of interest (e.g., in the shape of a particular electronic device).

In some embodiments, devices are produced by adsorbing/depositing onto a substrate (e.g., a planar substance having a top surface) a nucleic acid nanostructure (i.e., crystal) (or other 2D or 3D substrate) having a spatial resolution of 50 nm or less and containing at prescribed locations nucleic acid handles hybridized to complementary nucleic acid anti-handles that are coupled to moieties. "Adsorption" refers to a process by which atoms, ions or molecules adhere to surface. Nucleic acid adsorption can be achieved, for example, by physisorption, electrostatic absorption or chemical absorption. The moieties may be coupled to the nucleic acid nanostructure before or after the nanostructure is adsorbed onto the substrate.

In some embodiments, adsorption of a nucleic acid nanostructure, optionally having functionalized moieties, onto a surface of a substrate is driven by physisorption. For example, an intact substrate may be used for incubation of a nucleic acid nanostructure (i.e., crystal), optionally with functionalized moieties, in solution. In some embodiments, a flat substrate is carved to form grooves. These grooves trap nucleic acid nanostructure and increase the deposition yield.

In some embodiments, adsorption of a nucleic acid nanostructure (i.e., crystal) onto a surface of a substrate is driven by electrostatic absorption. For example, a substrate may be incubated initially with $Mg^{2+}$ solution to produce an $Mg^{2+}$ saturated substrate. The $Mg^{2+}$ saturated substrate is then used for nucleic acid nanostructure deposition.

In some embodiments, adsorption of a nucleic acid nanostructure (i.e., crystal), optionally with functionalized moieties, onto a surface of a substrate is driven by chemical absorption. For example, a substrate may be modified with an amino-containing reagent, such as, for example, polylysine, amino silane or polyethylenimine poly(allylamine hydrochloride) to produce a chemically-modified substrate. The chemically-modified substrate is then used for nucleic acid nanostructure adsorption.

In some embodiments, adsorption of a nucleic acid nanostructure (i.e., crystal) onto a surface of a substrate is driven by bimolecular binding. For example, a substrate may be modified with streptavidin, which can bind biotin-labeled nucleic acid nanostructures.

In some embodiments, nucleic acid nanostructures (i.e., crystals) of the present disclosure are assembled in or transferred to a solution (e.g., water). In some embodiments, the concentration of the nucleic acid nanostructure in solution is 10 pM-1 µM. For example, the concentration of the nucleic acid nanostructure in solution may be 10 pM to 1 nM, 10 pM to 500 pM, 500 pM to 1 nM, 1 nM to 500 nM, or 500 nM to 1 µM. In some embodiments, the concentration of the nucleic acid crystal in solution is 10 pM, 50 pM, 100 pM, 150 pM, 200 pM, 250 pM, 300 pM, 350 pM, 400 pM, 450 pM, 500 pM, 550 pM, 600 pM, 650 pM, 700 pM, 750 pM, 800 pM, 850 pM, 900 pM, 950 pM, 1 nM, 10 nM, 50 nM, 100 nM, 150 nM, 200 nM, 250 nM, 300 nM, 350 nM, 400 nM, 450 nM, 500 nM, 550 nM, 600 nM, 650 nM, 600 nM, 750 nM, 800 nM, 850 nM, 900 nM, 950 nM or 1 µM, or more.

In some embodiments, a solution that includes nucleic acid nanostructures (i.e., crystals) is permitted to incubate on a substrate during an adsorption step for 5 minutes (min) to 10 hours (hrs). For example, a solution that includes nucleic acid nanostructures may be permitted to incubate on a substrate during an adsorption step for 5 min, 10 min, 15 min, 20 min, 30 min, 45 min, 60 min, 2 hrs, 2.5 hrs, 3 hrs, 3.5 hrs, 4 hrs, 4.5 hrs, 6 hrs, 6.5 hrs, 7 hrs, 7.5 hrs, 8 hrs, 8.5 hrs, 9 hrs, 9.5 hrs or 10 hrs, or more. In some embodiments, a solution that includes nucleic acid nanostructures is permitted to incubate on a substrate during an adsorption step for 30 minutes to 4 hours.

In some embodiments, about 1-100 µl including 1 µl-10 µl of solution per $cm^2$ substrate is/are adsorbed on a substrate during an adsorption step. For example, the volume of solution deposited per $cm^2$ substrate may be 1 µl, 2 µl, 3 µl, 4 µl, 5, µl, 6 µl, 7 µl, 8 µl, 9 µl, 10 µl, or 100 µl or more.

In some embodiments, about 1-100 µl including 1 µl-10 µl of a solution containing a concentration of nucleic acid nanostructures (i.e., crystals) of 10 pM-1 µM is adsorbed on a substrate for 15 minutes to 4 hours.

Sub-Wavelength Waveguide

In some embodiments, moieties (e.g., metal nanoparticles) are aligned into three-dimensional architectures with controllable intra-chain and inter-chain spacings. Notably, intra-chain spacing around 5 nm (e.g., 4 nm, 5 nm, 6 nm) exhibits strong near-field coupling among moieties, which favors photon propagation along the extension direction of nanoparticle. Further stacking multiple chains of different orientations into three-dimensional space accomplishes the three-dimensional guiding of light propagation. Particularly, these moiety waveguides can direct light at sub-optical wavelength range, as each moiety chain is much smaller than the visible light wavelength (400-700 nm).

High-Density Information Storage

In some embodiments, moieties (e.g., nanoparticles) are aligned with strong coupling in the thickness (e.g., diameter or shortest length) direction while un-coupled in the lateral (e.g., longest length) direction. Such architecture can be further used to store information at different charging conditions. At optimal spacing conditions, the strongly-coupled moieties display multiple charging states, each with a unique bit for information storage; whereas lateral density can be maximized with the minimized lateral spacing to retain uncoupled system. Thus, in some embodiments, high-density information storage is achieved with both multi-bits at single position and high lateral density.

Integrated Circuits with 1-nm Fin-FET

In some embodiments, nanowires, such as carbon nanotubes (CNT), are used to construct a Fin-FET design with 1 nm (or 0.5 nm, 1.5 nm, 2.0 nm, 2.5 nm or 3 nm) fin width. Such feature is useful, for example, for miniaturizing current electronic units down to atomic level. Use of substrates (e.g., DNA crystals) to integrate billions of CNT into prescribed architectures may be applied, in some embodiments, to construct integrated circuits, such as central processing units (CPUs), at much smaller dimensions relative to existing technologies. Additionally, because DNA-directed CNT patterning can, in some embodiments, be achieved in aqueous solution and on flexible surface, such solution-processible fabrication may be used to manufacture flexible electronics for wearable devices, such as GOOGLE® Glass, and APPLE® Watch, with low energy consumption and high processing power.

Additional Embodiments

The present disclosure further provide embodiments described in the following numbered paragraphs:
1. A nucleic acid lithography method comprising:
   (a) adsorption a bare nucleic acid nanostructure onto a surface of a substrate; and (b) dry etching the surface of the substrate onto which the bare nucleic acid nanostructure is adsorbed, thereby producing a patterned substrate.

2. The method of paragraph 1, wherein the bare nucleic acid nanostructure is a bare deoxyribonucleic acid (DNA) nanostructure.

3. The method of paragraph 1, wherein the bare nucleic acid nanostructure is a bare ribonucleic acid (RNA) nanostructure.

4. The method of paragraph 1, wherein the bare nucleic acid nanostructure is a bare locked nucleic acid (LNA) nanostructure.

5. The method of paragraph 1, wherein the bare nucleic acid nanostructure is a bare protein nucleic acid (PNA) nanostructure.

6. The method of any one of paragraphs 1-5, wherein the dry etching is selected from plasma etching, ion beam etching, electron beam etching and X-ray etching.

7. The method of any one of paragraphs 1-6, wherein the bare nucleic nanostructure is a bare two-dimensional nucleic acid nanostructure.

8. The method of any one of paragraphs 1-6, wherein the bare nucleic nanostructure is a bare three-dimensional nucleic acid nanostructure.

9. The method of any one of paragraphs 1-8, wherein the substrate comprises an inorganic material.

10. The method of any one of paragraphs 1-9, wherein the substrate comprises an organic material.

11. The method of any one of paragraphs 1-8, wherein the substrate comprises silicon, silica, an oxide, a nitride, a metal or a non-metal.

12. The method of any one of paragraphs 1-8, wherein the substrate comprises a semiconductor or a combination of semiconductors.

13. The method of paragraph 12, wherein the semiconductor is a Group III-V semiconductor or a Group II-VI semiconductor.

14. The method of any one of paragraphs 1-8, wherein the substrate comprises a polymeric film.

15. The method of paragraph 14, wherein the polymeric film comprises polydimethylsiloxane (PDMS) or poly(methyl methacrylate) (PMMA).

16. The method of any one of paragraphs 1-15, wherein the bare nucleic acid nanostructure is a bare DNA nanostructure that is assembled from single-stranded DNA.

17. The method of paragraph 16, wherein the bare DNA nanostructure is assembled from synthetic single-stranded oligonucleotides.

18. The method of paragraph 17, wherein the bare DNA nanostructure is assembled from at least 50 synthetic single-stranded heterogeneous oligonucleotides.

19. The method of any one of paragraphs 16-18, wherein the bare DNA nanostructure is assembled from a single-stranded DNA with a length of at least 1 kilobase.

20. The method of any one of paragraphs 1-20, wherein the method does not include a metal, a metal oxide, or an oxide growth step.

21. The method of any one of paragraphs 1-20, wherein the adsorption step of (a) comprises contacting the surface of the substrate with a solution that comprises the bare nucleic acid nanostructure.

22. The method of paragraph 21, wherein the adsorption step of (a) includes physisorption, electrostatic absorption, or chemical absorption.

23. The method of any one of paragraphs 1-22, wherein the bare nucleic acid nanostructure is functionalized with metal nanoparticles, metal clusters, oxides, chalcogenides, nanowires, polymers and/or biomolecules.

24. A patterned substrate produced by the method of any one of paragraphs 1-23 having a feature resolution of less than 10 nm.

25. The patterned substrate of paragraph 24, wherein the patterned substrate has a feature resolution of 1 nm to 1 µm.

26. The patterned substrate of paragraph 25, wherein the patterned substrate has a feature resolution of 5 nm to 1 µm.

27. The patterned substrate of paragraph 25, wherein the patterned substrate has a feature resolution of 1 nm to 2 nm.

28. A device comprising the patterned substrate of any one of paragraphs 24-27.

29. The device of paragraph 28, wherein the device is an electronic device, a plasmonic device, a photonic device, a photovoltaic device or a hybrid device.

30. A nucleic acid lithography method comprising:
 (a) adsorbing a bare nucleic acid nanostructure onto a first substrate layer that is positioned above a second substrate layer;
 (b) dry etching or wet etching the surface of the first substrate layer onto which the bare nucleic acid nanostructure is adsorbed, thereby producing a secondary mask that is positioned above the second substrate layer; and
 (c) dry etching the second substrate layer onto which the secondary mask is adsorbed, thereby producing a patterned substrate.

31. The method of paragraph 30, wherein the bare nucleic acid nanostructure is a bare deoxyribonucleic acid (DNA) nanostructure.

32. The method of paragraph 30, wherein the bare nucleic acid nanostructure is a bare ribonucleic acid (RNA) nanostructure.

33. The method of paragraph 30, wherein the bare nucleic acid nanostructure is a bare locked nucleic acid (LNA) nanostructure.

34. The method of paragraph 30, wherein the bare nucleic acid nanostructure is a bare protein nucleic acid (PNA) nanostructure.

35. The method of any one of paragraphs 30-34, wherein the dry etching of step (b) and/or step (c) is selected from plasma etching, ion beam etching, electron beam etching and X-ray etching.

36. The method of any one of paragraphs 30-35, wherein the bare nucleic nano structure is a bare two-dimensional nucleic acid nanostructure.

37. The method of any one of paragraphs 30-36, wherein the bare nucleic nano structure is a bare three-dimensional nucleic acid nanostructure.

38. The method of any one of paragraphs 30-37, wherein the first substrate and/or the second substrate comprise an inorganic material.

39. The method of any one of paragraphs 30-37, wherein the first substrate and/or the second substrate comprise an organic material.

40. The method of any one of paragraphs 30-37, wherein the first substrate and/or the second substrate comprises silicon, silica, an oxide, a nitride, a metal or a non-metal.

41. The method of any one of paragraphs 30-37, wherein the first substrate and/or the second substrate comprise a semiconductor or a combination of semiconductors.

42. The method of paragraph 41, wherein the semiconductor is a Group III-V semiconductor or a Group II-VI semiconductor.
43. The method of any one of paragraphs 30-37, wherein the first substrate and/or the second substrate comprises a polymeric film.
44. The method of paragraph 43, wherein the polymeric film comprises polydimethylsiloxane (PDMS) or poly(methyl methacrylate) (PMMA).
45. The method of any one of paragraphs 30-44, wherein the bare nucleic acid nanostructure is a bare DNA nanostructure that is assembled from single-stranded DNA.
46. The method of paragraph 45, wherein the bare DNA nanostructure is assembled from synthetic single-stranded oligonucleotides.
47. The method of paragraph 46, wherein the bare DNA nanostructure is assembled from at least 50 synthetic single-stranded heterogeneous oligonucleotides.
48. The method of any one of paragraphs 45-47, wherein the bare DNA nanostructure is assembled from a single-stranded DNA with a length of at least 1 kilobase.
49. The method of any one of paragraphs 30-48, wherein the method does not include a metal, metal oxide, or an oxide growth step.
50. The method of any one of paragraphs 30-49, wherein the adsorption step of (a) comprises contacting the surface of the substrate with a solution that comprises the bare nucleic acid nanostructure.
51. The method of paragraph 50, wherein the adsorption step of (a) includes physisorption, electrostatic absorption, or chemical absorption.
52. The method of any one of paragraphs 1-22, wherein the bare nucleic acid nanostructure is functionalized with metal nanoparticles, metal clusters, oxides, chalcogenides, nanowires, polymers and/or biomolecules.
53. A patterned substrate produced by the method of any one of paragraphs 30-52 having a feature resolution of less than 10 nm.
54. The patterned substrate of paragraph 53, wherein the patterned substrate has a feature resolution of 1 nm to 1 µm.
55. The patterned substrate of paragraph 54, wherein the patterned substrate has a feature resolution of 5 nm to 1 µm.
56. The patterned substrate of paragraph 54, wherein the patterned substrate has a feature resolution of 1 nm to 2 nm.
57. A device comprising the patterned substrate of any one of paragraphs 53-56.
58. The device of paragraph 57, wherein the device is an electronic device, a plasmonic device, a photonic device, a photovoltaic device or a hybrid device.
59. A device comprising
a substrate having a spatial resolution of 50 nm or less and containing at prescribed locations nucleic acid handles hybridized to complementary nucleic acid anti-handles that are coupled to moieties.
60. The device of paragraph 59, wherein the substrate has a spatial resolution of 10 nm or less.
61. The device of paragraph 59, wherein the substrate has a spatial resolution of 1 nm to 50 nm.
62. The device of paragraph 61, wherein the substrate has a spatial resolution of 1 nm to 25 nm.
63. The device of paragraph 62, wherein the substrate has a spatial resolution of 2 nm to 5 nm.
64. The device of any one of paragraphs 59-63, wherein the substrate is an inorganic material.
65. The device of any one of paragraphs 59-63, wherein the substrate is an organic material.
66. The device of any one of paragraphs 59-63, wherein the substrate is a nucleic acid crystal.
67. The device of any one of paragraphs 59-63, wherein the substrate is a hybrid of two or more different materials.
68. The device of any one of paragraphs 59-63, wherein the substrate comprises a protein layer or a nucleic acid layer.
69. The device of any one of paragraphs 59-68, wherein the substrate is two-dimensional or three-dimensional.
70. The device of any one of paragraphs 59-69, wherein subsets of the nucleic acid handles are arranged on the substrate to form a crossbar configuration, a chiral configuration or parallel rows.
71. The device of any one of paragraphs 59-70, wherein the moieties are nanoparticles, nanowires, or nucleic acids.
72. The device of any one of paragraphs 59-70, wherein the moieties are semiconductor nanoparticles or metal nanoparticles.
73. The device of any one of paragraphs 59-70, wherein the moieties are gold nanoparticles.
74. The device of any one of paragraphs 59-70, wherein the moieties are carbon nanotubes.
75. The device of any one of paragraphs 59-70, wherein the moieties are single-stranded nucleic acids, double-stranded nucleic acids, or self-assembled one-, two- or three-dimensional nucleic acid nanostructures.
76. The device of any one of paragraphs 59-75, wherein the diameter of the moieties is 1 nm to 100 nm.
77. The device of any one of paragraphs 59-76, wherein the moieties are comprised of a heterogeneous mixture of moieties.
78. The device of any one of paragraphs 59-77, wherein each anti-handle is coupled to an individual moiety.
79. The device of any one of paragraphs 59-78, wherein a subset of anti-handles is coupled to the same moiety.
80. The device of any one of paragraphs 59-79, wherein the nucleic acid handles are coupled to a surface of the substrate.
81. The device of any one of paragraphs 59-80, wherein the nucleic acid handles are coupled to a single layer of the substrate.
82. The device of any one of paragraphs 59-80, wherein the nucleic acid handles are coupled to multiple layers of the substrate.
83. The device of any one of paragraphs 59-80, wherein the nucleic acid handles are coupled to channels formed in the substrate.
84. A device comprising
a substrate having a spatial resolution of less than 50 nm and containing at prescribed locations a moiety, wherein the moiety is indirectly coupled to or confined to the substrate through a nucleic acid hybridization interaction, a protein-protein interaction, a hydrophobic interaction, an electrostatic interaction, $\pi$-$\pi$ stacking, spatial confinement or electrophoresis.
85. A device comprising
a substrate having a spatial resolution of less than 50 nm and at least one channel, wherein moieties are spatially confined to the at least one channel, and the diameter of the at least one channel is no wider than twice the average diameter of the moieties.
86. The device of paragraph 84 or 85, wherein the substrate is a nucleic acid crystal.
87. The device of paragraph 84 or 85, wherein the moieties are nanoparticles, nanowires, or nucleic acids.

88. The device of any one of paragraph 59-87, wherein the device is an electronic device, a plasmonic device, a photonic device, a photovoltaic device or a hybrid device.
89. The device of any one of paragraph 59-88, wherein the device comprises an integrated circuit.
90. A method of producing a device, comprising:
depositing a nucleic acid crystal on a surface of a substrate; and
coupling to the nucleic acid crystal at prescribed locations nucleic acid handles complementary to nucleic acid anti-handles that are coupled to moieties.
91. The method of paragraph 90, further comprising coupling the moieties to the nucleic acid crystal through hybridization of the nucleic acid handles to the complementary nucleic acid anti-handles.
92. The method of paragraph 91, wherein the moieties are coupled to the nucleic acid crystal after the nucleic acid crystal is deposited on the surface of the substrate.

The present invention is further illustrated by the following Examples, which in no way should be construed as further limiting. The entire contents of all of the references (including literature references, issued patents, published patent applications, and co pending patent applications) cited throughout this application are hereby expressly incorporated by reference, in particular for the teachings that are referenced herein.

EXAMPLES

Examples 1

FIG. 1A illustrates one embodiment of the present disclosure whereby gold nanoparticles chains are aligned in parallel on DNA crystals along the y direction (FIG. 1A). A basic DNA unit cell is designed with x-z cross section of 8 helices by 4 helices and a y-dimensional length of 96 base pairs. This provides a designed x-y periodicity of 15 nm×30 nm, assuming a 2.5 nm helix width and a 0.32 nm per base pair. The repetitive DNA unit cell grows along the x- and y-direction to form the domain composed of four homogeneous sequenced 12-nt single-stranded DNA (ssDNA) handles to capture one gold nanoparticle. Multiple 12-nt anti-handles (a ssDNA with sequence complementary to the handle) are also immobilized onto the gold nanoparticle surface. The hybridization between the handles and the anti-handles anchor the gold nanoparticles onto the prescribed position of DNA crystal. Each gold nanoparticle deviating from the designed position cannot bind to all four handles within a unit cell, which results in an energy penalty for minimizing unstable misaligned products.

In typical experiments, DNA crystals were folded by staged isothermal folding of the nucleic acid strand mixtures (500 nM of each unpurified DNA strand in 5 mM Tris, pH 7.9, 1 mM EDTA, 40 mM $MgCl_2$, without careful adjustment of strand stoichiometry). The reaction solution was first kept at 44° C. for 12 h, followed by incubation at 39° C. for another 12 h. To make the crystal grow large enough, fresh growth strands were added (500 nM of each unpurified DNA strand in 5 mM Tris, pH 7.9, 1 mM EDTA, 40 mM $MgCl_2$, without careful adjustment of strand stoichiometry) and elongated the reaction for another 12 h at 39° C. Without purification, the crude products were mixed with gold nanoparticles in the presence of 450 mM $NaNO_3$ at room temperature for three hours in the dark. The molar stoichiometry between gold nanoparticle and DNA crystals was adjusted based on maximizing surface aligning density and minimizing free gold nanoparticles in solution. After that, the gold-DNA conjugated were deposited onto copper grids and imaged by transmission electron microscopy (TEM).

TEM imaging confirmed the successful formation of designed extending arrays of 8-nm gold nanoparticle chains (FIGS. 2A-C). After gold nanoparticle alignment, arrays of gold nanoparticle chains along the y direction were observed on the crystal surface. More than 300 nanoparticles were successfully immobilized onto each DNA crystal. Five other architectures, ranging from one-dimensional chains to three-dimensional architectures, were also produced with 8-nm and 13-nm gold nanoparticles (FIGS. 2A-C).

FIGS. 3A and B depict a process for using 3D DNA crystals to spatially confine chemical-directed CNT patterning. A 3D DNA crystal with parallel grooves of 5 nm thickness was first designed (FIG. 3A), based on a modular DNA brick design. Specific single-stranded DNA recognition groups were then introduced to fully cover the CNT surface. Incubation of CNTs with preformed DNA crystals at mild conditions provided parallel CNT arrays (FIG. 3B). In a typical experiment, preformed DNA crystals (similar with above protocols) were mixed with single-stranded DNA wrapped CNTs in the presence of 7.5 mM $MgCl_2$ at 35° C. for nine hours in the dark, and then cooled at 4° C. The molar stoichiometry between gold nanoparticles and DNA crystals was adjusted based on maximizing surface aligning density and minimizing free gold nanoparticles in solution. After that, the CNT-DNA conjugated were deposited onto copper grids and imaged by transmission electron microscopy (TEM).

Examples 2

This Example describes the use of rod-shaped DNA nanostructures (10 nm in width and 2 μm in length) as masks to direct the reactive ion (plasma) etching of inorganic substrates into prescribed linear patterns.

DNA Self-Assembly to Form DNA Rod with 4×4 Helices

Figure 6A:
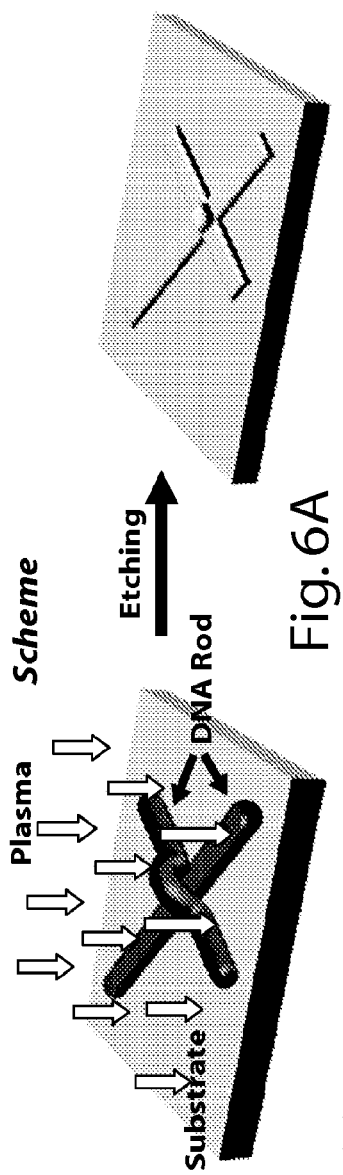
FIG. 6A shows a schematic of one embodiment of a DNA lithography method of the present disclosure. Overlapping bare DNA rods (used as a bare DNA nanostructure mask) were adsorbed onto a substrate, and then the substrate onto which the bare DNA rods were adsorbed was etched under reactive ion etching conditions, thereby producing a prescribed three-dimensional pattern of overlapping rod structures.
Figure 6B:
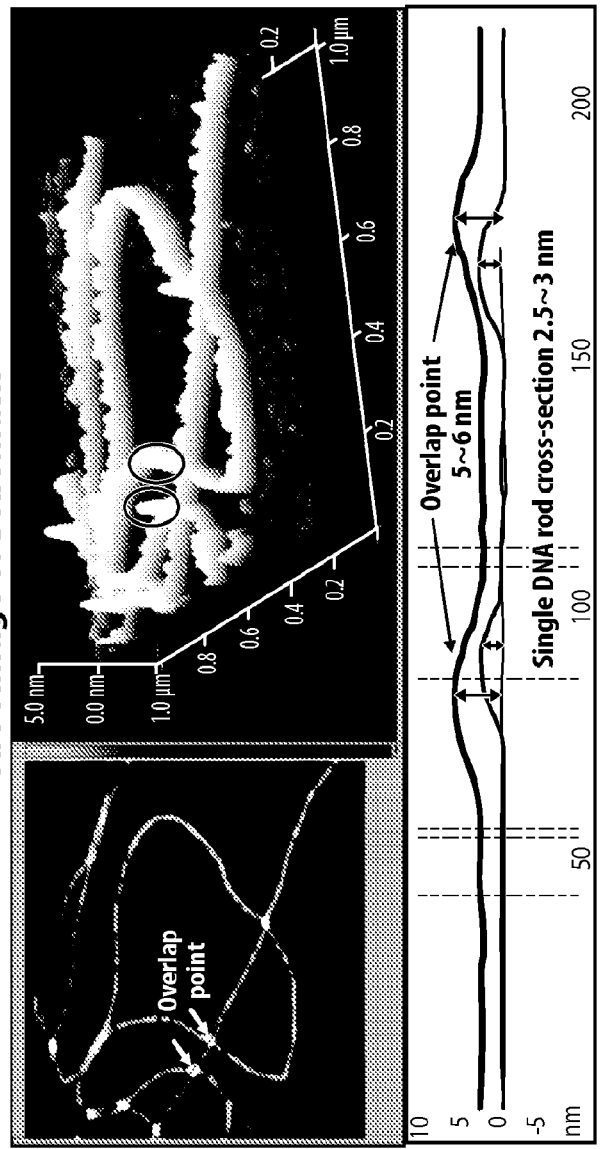
FIG. 6B shows an atomic force microscopy (AFM) image of the bare DNA nanostructure mask.
Figure 6C:
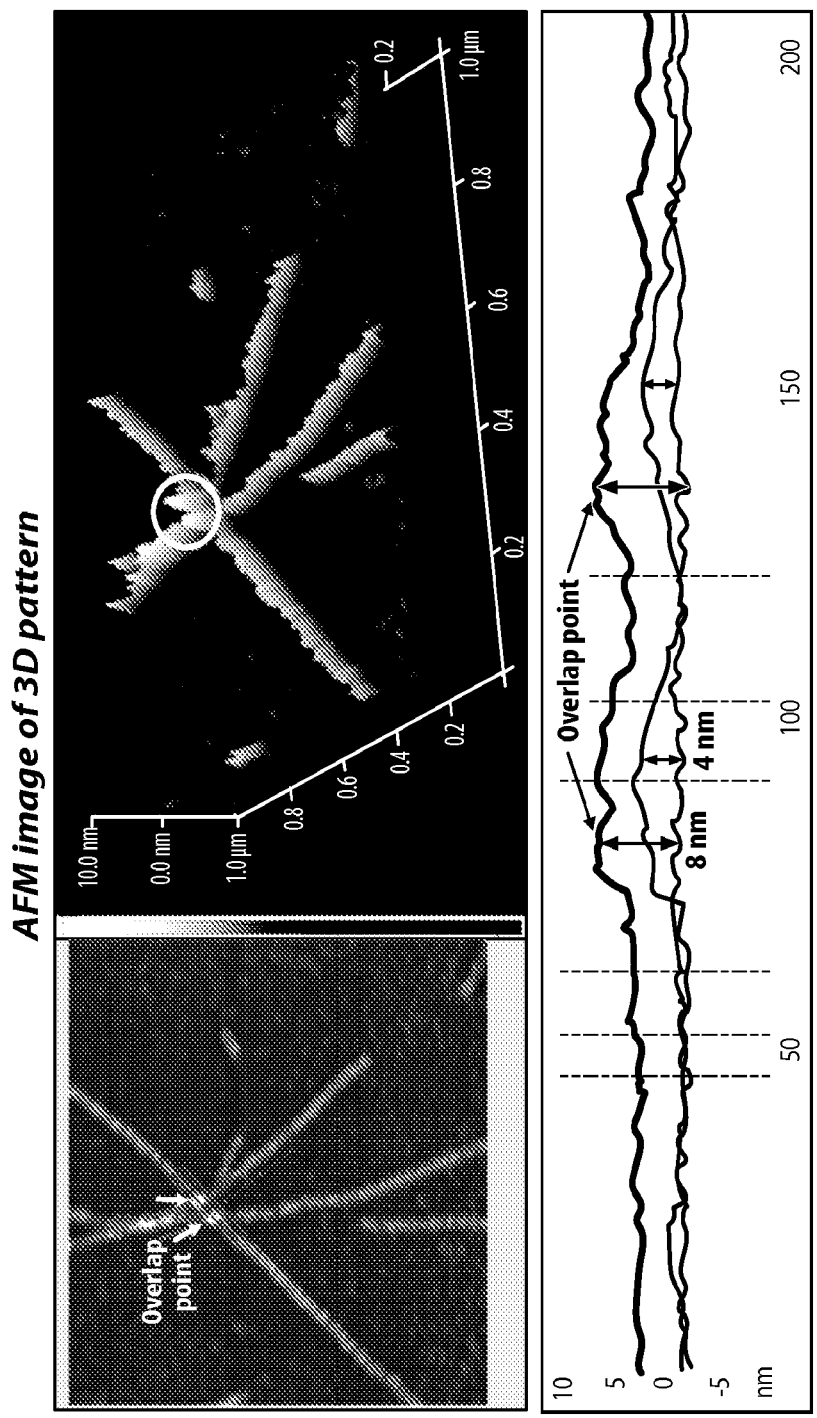
FIG. 6C shows an AFM image of the prescribed three-dimensional patterned substrate.

Single-stranded tile (SST) DNA strands were mixed in polymerase chain reaction (PCR) tubes to produce a solution having a final concentration of 1 μM for each strand of DNA. 9 μl of the solution (e.g., comprising or consisting of water) of DNA strands and 1 μl of the folding buffer were combined (final concentration: 0.9 μM SST strands, 5 mM Tris·Cl, pH=7.9 1 mM EDTA, and 40 mM $MgCl_2$). The combined solution was shaken gently to homogenize the solution. The DNA in the solution was annealed in a thermal cycler with a staged isothermal folding for 24 hours using the following the program: 80° C. for 15 minutes, 44° C. for 12 hours, and 39° C. for an additional 12 hours. The resulting DNA nanostructures were rod-shaped (FIGS. 6A-6C).

DNA Nanostructure Adsorption

1 μl of the solution containing rod-shaped DNA (0.5×TE buffer, 40 mM $Mg^{2+}$ 10 nM base pair) was transferred onto a clean silicon wafer (5 mm×5 mm in size), followed by 1 hour incubation in a sealed container under saturated humidity to facilitate the adsorption. The wafer was then wash with DI water to remove residual solution and dried by compressed air flow.

Reactive Ion Etching

Etching of the silicon substrate containing the 4×4 helical DNA rods was performed on an inductively coupled plasma (ICP) reactor equipped reactive ion etcher (Surface Technology Systems Co.) The etching parameters included chamber pressure 15 mbar, $CHF_3$ gas in 10 standard cubic centimeters per min (SCCM), ICP electrode power 300 W, RF biased electrode powered 12 W, and etching duration 2 minutes.

As shown in FIGS. 6A-6C, the thickness of the junction formed by two overlapping DNA rods and the three-dimensional features of the composite structure was retained on the etched silicon substrate.

Examples 3

Deposition of DNA Nanostructure to a Substrate Followed by Desalting and Drying:

The following example is non-limiting and it is to be understood that a range of nucleic acid nanostructures and substrates and conditions, such as described herein, can be used to effect a similarly desirable result.

A solution (e.g., 0.5×Tris-ethylenediaminetetraacetic acid (TE) buffer, 40 mM $Mg^{2+}$; or 100 mM-1 M $NaNO_3$) comprising a bare three-dimensional DNA nanostructure (e.g., 10 pM-1 µM nanostructure concentration, at least 32 base pairs in length) with a depth of 2 nm is adsorbed onto a substrate (e.g., 1 µl-100 µl solution per $cm^2$ substrate), and the solution is permitted to incubate on the substrate (e.g., for 3 minutes to 4 hours) at 4~25° C. with 50-100% humidity for deposition of DNA nanostructure. Following deposition, the solution is removed (e.g., by wiping and/or by forced air flow) for the subsequent desalting process. The desalting process is applied to remove residual inorganic salt from the DNA nanostructure and substrate before the final drying step.

Examples 4

Coating or PVD of Metallic Thin Layer on DNA Template, Followed by Lift-Off Process.

The following example is non-limiting and it is to be understood that a range of nucleic acid nanostructures, substrates, deposition materials or coats, and conditions, such as described herein, can be used to effect a similarly desirable result.

Figure 12:
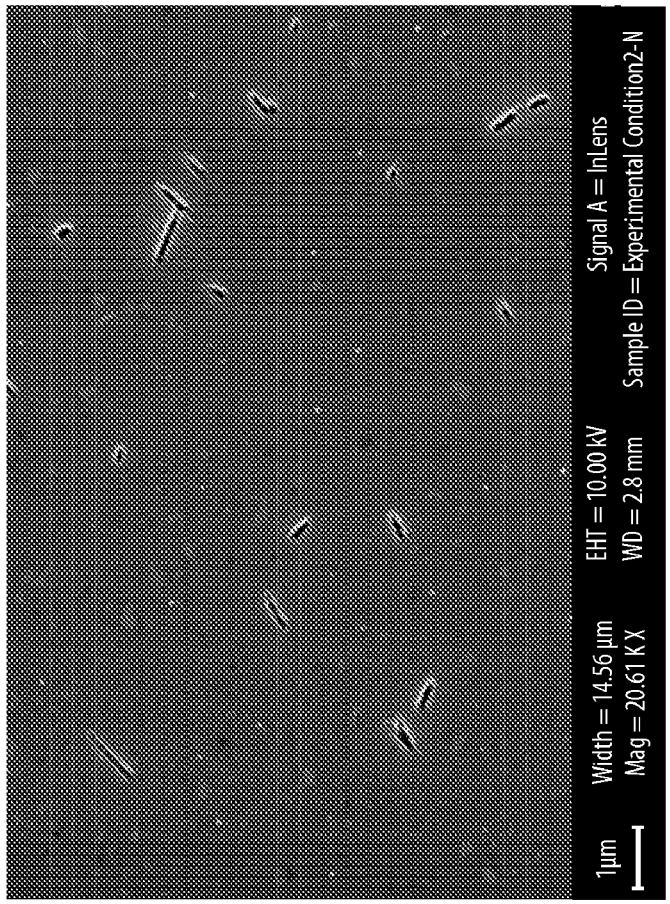
FIG. 12 shows a schematic (left) and experimental results (right) relating to coating a metallic thin layer on a DNA template, followed by a lift-off process.
Figure 12:
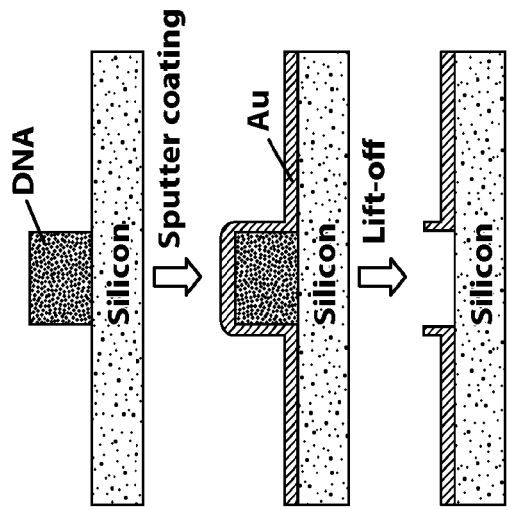

3D DNA brick crystals in rod shape (50 nm in width, 1 µm in length) were deposited on silicon substrate, followed by desalting and drying. Then, the dry substrate was coated by 5 nm of gold film on a sputter coating equipment. The Au coated substrate was then washed with pure water in an ultrasonication bath, in order to break down the 3D DNA brick crystal and lift off the Au shell on top of the crystal, as shown (FIG. 12). On the SEM image, the region that was covered by the DNA brick crystal has no Au deposition, so it looks darker than the background with Au deposition. Around the boundary of DNA brick crystal there will be a gold shell/sidewall having much stronger electron scattering effect. Thus, we can see a bright outline, indicating the former position of the DNA template.

Examples 5

Using 3D DNA Nanostructure as Template to Print Moieties to a Substrate.

The following example is non-limiting and it is to be understood that a range of nucleic acid nanostructures, moieties, and substrates and conditions, such as described herein, can be used to effect a similarly desirable result.

Figure 13A:
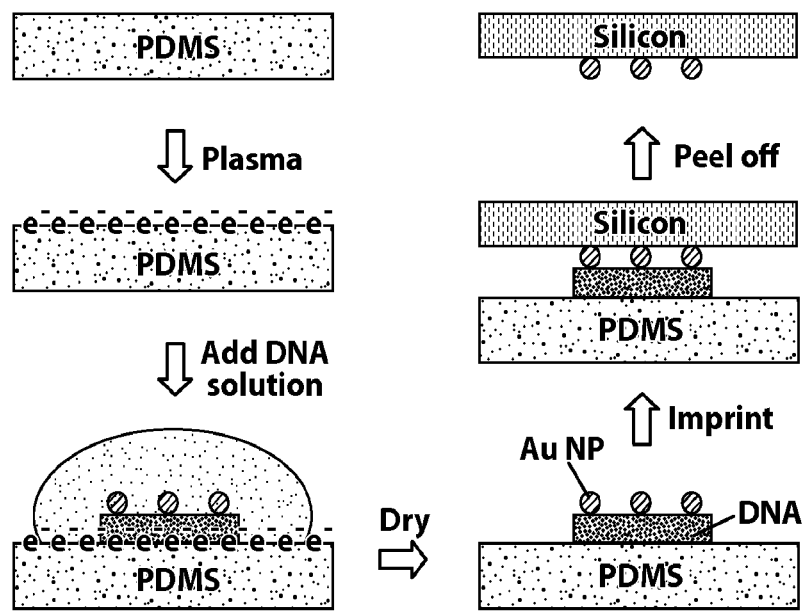
FIG. 13A is a schematic showing the use of a 3D DNA nanostructure as a template to print moieties to a substrate.
Figure 13B:
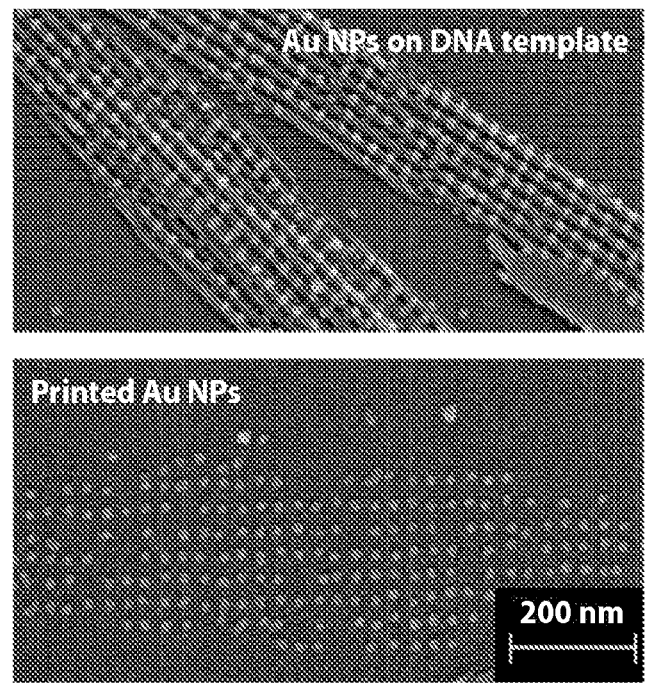
FIG. 13B is an image of Au nanoparticles on a DNA template as well as the printed patter of the Au nanoparticles on a silicon wafer, generated using the process of FIG. 13A.

A solution (e.g., 0.5×Tris-ethylenediaminetetraacetic acid (TE) buffer, 40 mM $Mg^{2+}$; or, 100 mM-1 M $NaNO_3$) comprising a three-dimensional DNA nanostructure (e.g., 10 pM-1 µM nanostructure concentration, at least 32 base pairs in length) functionalized with a gold nanoparticle pattern, was permitted to incubate on a plasma treated PDMS substrate (e.g., for 3 minutes to 4 hours) at 4~25° C. with 50-100% humidity for efficient deposition. Then, the solution was removed (e.g., by wiping and/or by forced air flow), and immediately the PDMS substrate was press onto a clean silicon substrate, with the DNA deposition side facing to the target substrate, by a pressure from 1 bar to 50 bar, for a duration from 5 min to 1 h. Finally, the PDMS substrate was peeled off to remove the DNA nanostructure, with the gold nanoparticle pattern remaining on the silicon wafer. This process and the experimental results are illustrated in FIG. 13.

Examples 6

Epitaxial Growth

The following example is non-limiting and it is to be understood that a range of seeds and conditions, such as described herein, can be used to effect a similarly desirable result.

A typical epitaxial growth is illustrated in FIG. 14 and may proceed as follows:

(1) Seed formation: A seed solution (e.g., 0.5×Tris-ethylenediaminetetraacetic acid (TE) buffer, 40 mM $Mg^{2+}$) with single-stranded DNA bricks (e.g., 100 nM-1 µM concentration for each brick, at least 32 base pairs in length) is first incubated at 80° C. for 15 min, followed by incubation at 44° C. for 12 hours, 39° C. for 24 hours, and 31° C. for 8 hours.

(2) Epitaxial growth: A growth solution (e.g., 0.5×Tris-ethylenediaminetetraacetic acid (TE) buffer, 40 mM $Mg^{2+}$) with single-stranded DNA bricks (e.g., 100 nM-1 µM concentration for each brick, at least 32 base pairs in length) is first incubated at 80° C. for 15 min, and then cooled to 38° C. Then pre-formed seed solution is added into the growth solution, followed by further incubation at 38° C. for 48 hours, 33° C. for 48 hours, and 31° C. for 8 hours.

For the epitaxial growth, the seed formation temperature ranges from 31° C. to 70° C., and the Mg concentration ranges from 5 mM to 60 mM. At each temperature, the incubation time can vary from 1 min to 1 week. Multiple (more than two) growth stages, each at identical or different temperatures may exist depending on the growth pathways.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03

What is claimed is:

1. A nucleic acid lithography method comprising:
   (a) adsorption a bare nucleic acid nanostructure onto a surface of a substrate; and
   (b) dry etching the surface of the substrate onto which the bare nucleic acid nanostructure is adsorbed, thereby producing a patterned substrate.

2. The method of claim 1, wherein the bare nucleic acid nanostructure is a bare deoxyribonucleic acid (DNA) nanostructure.

3. The method of claim 1, wherein the bare nucleic acid nanostructure is a bare ribonucleic acid (RNA) nanostructure, a bare locked nucleic acid (LNA) nanostructure, or is a bare protein nucleic acid (PNA) nanostructure.

4. The method of claim 1, wherein the dry etching is selected from plasma etching, ion beam etching, electron beam etching and X-ray etching.

5. The method of claim 1, wherein the bare nucleic nanostructure is a bare two-dimensional nucleic acid nanostructure.

6. The method of claim 1, wherein the bare nucleic nanostructure is a bare three-dimensional nucleic acid nanostructure.

7. The method of claim 1, wherein the substrate comprises an inorganic material or an organic material.

8. The method of claim 1, wherein the substrate comprises silicon, silica, an oxide, a nitride, a metal, a non-metal, or a polymeric film.

9. The method of claim 1, wherein the substrate comprises a semiconductor or a combination of semiconductors.

10. The method of claim 9, wherein the semiconductor is a Group III-V semiconductor or a Group II-VI semiconductor.

11. The method of claim 8, wherein the polymeric film comprises polydimethylsiloxane (PDMS) or poly(methyl methacrylate) (PMMA).

12. The method of claim 1, wherein the bare nucleic acid nanostructure is a bare DNA nanostructure that is assembled from single-stranded DNA.

13. The method of claim 12, wherein the bare DNA nanostructure is assembled from synthetic single-stranded oligonucleotides.

14. The method of claim 13, wherein the bare DNA nanostructure is assembled from at least 50 synthetic single-stranded heterogeneous oligonucleotides.

15. The method of claim 1, wherein the bare DNA nanostructure is assembled from a single-stranded DNA with a length of at least 1 kilobase.

16. The method of claim 1, wherein the adsorption step of (a) comprises contacting the surface of the substrate with a solution that comprises the bare nucleic acid nanostructure.

17. The method of claim 1, wherein the bare nucleic acid nanostructure is functionalized with metal nanoparticles, metal clusters, oxides, chalcogenides, nanowires, polymers and/or biomolecules.

18. A patterned substrate produced by the method of claim 1 having a feature resolution of 1 nm to 1 μm.

19. A device comprising the patterned substrate of claim 18.

20. The device of claim 19, wherein the device is an electronic device, a plasmonic device, a photonic device, a photovoltaic device or a hybrid device.

21. A nucleic acid lithography method comprising:
(a) adsorbing a bare nucleic acid nanostructure onto a first substrate layer that is positioned above a second substrate layer;
(b) dry etching or wet etching the surface of the first substrate layer onto which the bare nucleic acid nanostructure is adsorbed, thereby producing a secondary mask that is positioned above the second substrate layer; and
(c) dry etching the second substrate layer onto which the secondary mask is adsorbed, thereby producing a patterned substrate.

22. The method of claim 21, wherein the bare nucleic acid nanostructure is a bare deoxyribonucleic acid (DNA) nanostructure, a bare ribonucleic acid (RNA) nanostructure, a bare locked nucleic acid (LNA) nanostructure, or a bare protein nucleic acid (PNA) nanostructure.

23. The method of claim 21, wherein the dry etching of step (b) and/or step (c) is selected from plasma etching, ion beam etching, electron beam etching and X-ray etching.

24. The method of claim 21, wherein the bare nucleic nanostructure is a bare two-dimensional nucleic acid nanostructure or a bare three-dimensional nucleic acid nanostructure.

25. The method of claim 21, wherein the first substrate and/or the second substrate comprises silicon, silica, an oxide, a nitride, a metal, a non-metal, a semiconductor, or a polymeric film.

26. A patterned substrate produced by the method of claim 21 having a feature resolution of 1 nm to 1 μm.

27. A device comprising the patterned substrate of claim 26.

28. The device of claim 27, wherein the device is an electronic device, a plasmonic device, a photonic device, a photovoltaic device or a hybrid device.

29. A device comprising
a substrate having a spatial resolution of 50 nm or less and containing at prescribed locations nucleic acid handles hybridized to complementary nucleic acid anti-handles that are coupled to moieties.

30. The device of claim 29, wherein the substrate is an inorganic material, an organic material, a nucleic acid crystal, a hybrid of two or more different materials, or comprises a protein layer or a nucleic acid layer.

31. The device of claim 29, wherein the substrate is two-dimensional or three-dimensional.

32. The device of claim 29, wherein the moieties are nanoparticles, nanowires, or nucleic acids.

33. A device comprising
a substrate having a spatial resolution of less than 50 nm and containing at prescribed locations a moiety, wherein the moiety is indirectly coupled to or confined to the substrate through a nucleic acid hybridization interaction, a protein-protein interaction, a hydrophobic interaction, an electrostatic interaction, π-π stacking, spatial confinement or electrophoresis.

34. A device comprising
a substrate having a spatial resolution of less than 50 nm and at least one channel, wherein moieties are spatially confined to the at least one channel, and the diameter of the at least one channel is no wider than twice the average diameter of the moieties.

35. The device of claim 33, wherein the substrate is a nucleic acid crystal.

36. The device of claim 33, wherein the moieties are nanoparticles, nanowires, or nucleic acids.

37. The device of claim 29, wherein the device is an electronic device, a plasmonic device, a photonic device, a photovoltaic device or a hybrid device.

38. The device of claim 29, wherein the device comprises an integrated circuit.

* * * * *